United States Patent
Atanasio et al.

(10) Patent No.: US 11,897,945 B2
(45) Date of Patent: Feb. 13, 2024

(54) METHODS OF TREATING ALLERGY USING ANTI-BET V 1 ANTIBODIES

(71) Applicant: REGENERON PHARMACEUTICALS, INC., Tarrytown, NY (US)

(72) Inventors: Amanda Atanasio, Valhalla, NY (US); Gary Herman, Princeton, NJ (US); Meagan P. O'Brien, New York, NY (US); Jamie M. Orengo, Cortlandt Manor, NY (US); Lorah Perlee, Wilton, CT (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 0 days.

(21) Appl. No.: 17/364,299

(22) Filed: Jun. 30, 2021

(65) Prior Publication Data
US 2022/0002394 A1    Jan. 6, 2022

Related U.S. Application Data

(60) Provisional application No. 63/129,253, filed on Dec. 22, 2020, provisional application No. 63/047,126, filed on Jul. 1, 2020.

(51) Int. Cl.
| | | |
|---|---|---|
| *C07K 16/18* | (2006.01) | |
| *A61P 37/08* | (2006.01) | |
| *A61K 39/00* | (2006.01) | |
| *A61K 39/395* | (2006.01) | |

(52) U.S. Cl.
CPC ............ *C07K 16/18* (2013.01); *A61K 39/395* (2013.01); *A61P 37/08* (2018.01); *A61K 2039/505* (2013.01); *A61K 2039/545* (2013.01); *C07K 2317/565* (2013.01)

(58) Field of Classification Search
None
See application file for complete search history.

(56) References Cited

U.S. PATENT DOCUMENTS

| | | |
|---|---|---|
| 5,670,626 A | 9/1997 | Chang |
| 6,596,541 B2 | 7/2003 | Murphy et al. |
| 6,849,259 B2 | 2/2005 | Haurum et al. |
| 10,793,624 B2 | 10/2020 | Orengo et al. |
| 11,767,358 B2 | 9/2023 | Orengo et al. |
| 2003/0003133 A1 | 1/2003 | Schneider |
| 2004/0101920 A1 | 5/2004 | Radziejewski et al. |
| 2009/0304752 A1 | 12/2009 | Mistrello et al. |
| 2010/0034812 A1 | 2/2010 | Majdic et al. |
| 2016/0223563 A1 | 8/2016 | Yancopoulos et al. |
| 2018/0346555 A1* | 12/2018 | Orengo .................. C07K 16/16 |
| 2021/0054056 A1 | 2/2021 | Orengo et al. |

FOREIGN PATENT DOCUMENTS

| | | |
|---|---|---|
| EP | 0619323 | 10/1994 |
| WO | 1994/010194 | 5/1994 |
| WO | 1994/024164 | 10/1994 |
| WO | 2005/103081 | 11/2005 |
| WO | 2007/134350 | 11/2007 |
| WO | 2018/222854 | 12/2018 |
| WO | 2020/018820 | 1/2020 |

OTHER PUBLICATIONS

Calderon et al. 'Prolonged preseasonal treatment phase with Grazax sublingual immunotherapy increases clinical efficacy.' Allergy 62(8):958-961, 2007.*
Lombardi et al. 'Administration regimens for sublingual immunotherapy to pollen allergens: what do we know?' Allergy 64(6):849-54, 2009.*
Avarez-Cuesta et al. 'Standards for practical allergen-specific immunotherapy.' Allergy 61 Suppl 82:1-20, 2006.*
Atanasio, et al. (2021) "Targeting Immunodominant Bet v 1 Epitopes with Monoclonal Antibodies Prevents the Birch Allergic Response", Journal of Allergy and Clinical Immunology, 12 pages.
Gevaert, et al. (2021) "Novel Antibody Cocktail Targeting Bet v 1 Rapidly and Sustainability Treats Birch Allergy Symptoms in a Phase 1 Study", Journal of Allergy and Clinical Immunology, pp. 1-10.
Orengo, et al. (2018) "Treating Cat Allergy with Monoclonal IgG Antibodies that Bind Allergen and Prevent IgE Engagement", Nature Communications, 9(1):1-15.
PCT International Search Report and Written Opinion received for PCT/US2021/039945, dated Oct. 8, 2021, 15 pages.
Al-Lazikani et al (1997) "Standard Conformations for the Canonical Structures of Immunoglobulins", J. Mol. Biol. 273:927-948.
Allen (1999) The Art, Science and Technology of Pharmaceutical Compounding.
Altschul et al (1990) "Basic Local Alignment Search Tool", J. Mol. Biol. 215: 403-410.
Altschul et al (1997) "Grapped BLAST and PSI-BLAST: a New Generation of Protein Database Search Programs", Nucleic Acids Res. 25(17):3389-3402.
Angal et al. (1993) "A Single Amino Acid Substitution Abolishes the Heterogeneity of Chimeric Mouse/Human (IgG4) Antibody" Molecular Immunology 30:105-108.
Antibodies (2014) Harlow and Lane (Cold Spring Harbor Press, Cold Spring Harb., NY) "A Laboratory Manual".
Breiteneder et al. (1989) "The gene coding for the major birch pollen allergen Betvl, is highly homologous to a pea disease resistance response gene" EMBO J. 8(7):1935-1938.
Bucher et al (2004) "Effect of Tree Pollen Specific, Subcutaneous Immunotherapy on the Oral Allergy Syndrome to Apple and Hazelnut" Allergy 59(12):1272-1276.

(Continued)

*Primary Examiner* — Nora M Rooney
(74) *Attorney, Agent, or Firm* — FisherBroyles, LLP; Cara L. Crowley-Weber; Lisa Dornbach Flanagan

(57) ABSTRACT

The present disclosure provides methods for treating, preventing, or ameliorating one or more symptoms of birch allergy or allergic disease in a subject by administering to the subject an antibody or antigen-binding fragment thereof that binds Bet v 1, or a cocktail of antibodies or antigen-binding fragments thereof that bind Bet v 1.

37 Claims, 16 Drawing Sheets
Specification includes a Sequence Listing.

(56) References Cited

OTHER PUBLICATIONS

Buters et al. (2012) "Release of Bet v 1 from birch pollen from 5 European countries. Results from the HIALINE study" Atomospheric Environment 55:496-505.

Calderon et al (2014) "A Comparative Analysis of Symptom and Medication Scoring Methods Used in Clinical Trials of Sublingual Immunotherapy for Seasonal Allergic Rhinitis" Clin Exp Allergy 44(10):1228-39.

Carlson and Coop (2019) "Pollen Food Allergy Syndrome (PFAS): A Review of Current Available Literature", Annals of Allergy, Asthma & Immunology, 123:359-365.

De Pascalis et al. (2002) "Grafting of "Abbreviated" Complementarity-Determining Regions Containing Specificity—Determining Residues Essential for Ligand Contact to Engineer a Less Immunogenic Humanized Monoclonal Antibody" J. Immunol 169:3076-3084.

Denepoux et al. (2000) "Molecular Characterization of Human IgG Monoclonal Antibodies Specific for the Major Birch Pollen Allergen Bet v 1. Anti-allergen IgG Can Enhance the Anaphylactic Reaction" FEBS Lett 465(1):39-46.

Ehring (1999) "Hydrogen Exchange/Electrospray Ionization Mass Spectrometry Studies of Structural Features of Protein/Protein Interactions" Analytical Biochemistry 267(2):252-259.

Engen and Smith (2001) "The Basics of Ion Chromatography" Anal. Chem. 73:256A-265A.

Erler et al (2011) "Proteomic Profiling of Birch (Betula verrucosa) Pollen Extracts from Different Origins" Proteomics 11(8):1486-1498.

Focke et al. (2009) "Molecular Composition and Biological Activity of Commercial Birch Pollen Allergen Extracts" European Journal of Clinical Investigation 39(5):429-436.

Frew (2010) "Allergen Immunotherapy", Journal of Allergy and Clinical Immunology, 125:S306-313.

Gieras et al. (2011) "Mapping of Conformational IgE Epitopes with Peptide-Specific Monoclonal Antibodies Reveals Simultaneous Binding of Different IgE Entibodies to a Surface Patch on the Major Birch Pollen Allergen, Bet v 1" J. Immunol. 186(9):5333-5334.

Goel et al. (2004) "Plasticity within the Antigen-Combining Site May Manifest as Molecular Mimicry in the Humoral Immune Response" J. Immunol. 173(12):7358-7367.

Gonnet et al. (1992) "Exhaustive Matching of the Entire Protein Sequence Database" Science 256: 1443-45.

Hauser (2010) "Panallergens and their Impact on the Allergic Patient", Allergy, Asthma & Clinical Immunology 6:1.

Hauser et al. (2011) "Bet v 1-like pollen allergens of multiple Fagales species can sensitize atopic individuals" Clin Exp Allergy 41: 1804-14.

Hochleitner et al. (2000) "Characterization of a discontinuous epitope of the human immunodefiency virus (HIV) core protein p24 by eptiope excision and differential chemical modification followed by mass spectrometric peptide mapping analysis" Protein Science 9: 487-496.

Ito et al (2015) "The associations Between Daily Spring Pollen Counts, Over-the-Counter Allergy Medication Sales, and Asthma Syndrome Emergency Department Visits in New York City, 2002-2012", Environmental Health: A Global Access Science Source, 14:71.

Jakobsen et al. (2004) "Isolation of High-Affinity Human IgE and IgG Antibodies Recognising Bet v 1 and Humicola Lanuginosa Lipase from Combinatorial Phage Libraries" Molecular Immunology 41(10):941-953.

Jarolim et al. (1989) "Specificities of IgE and IgG antibodies in patients with birch pollen allergy" Int Arch Allergy Appl Immunol. 88(1-2): 180-182.

Kabat (1991) "Sequences of Proteins of Immunological Interest", National Institutes of Health, Bethesda, Md.

Kazane et al (2013) "Self-Assembled Antibody Multimers Through Peptide Nucleic Acid Conjugation", J. Am. Chem. Soc. [Epub: Dec. 4, 2012] 135:340-346.

Khan et al. (2014) "Adjustable Locks and Flexible Keys: Plasticity of Epitope-Paratope Interaction in Germline Antibodies" J. Immunol. 192:5398-5405.

Klein et al (2012) "Progress in Overcoming the Chain Association Issue in Bispecific Heterodimeric IgG Antibodies", mAbs 4(6):653-663.

Kofler et al (2012) "Crystallographically Mapped Ligand Binding Differs in High and Low IgE Binding Isoforms of Birch Pollen Allergen Bet v 1", J. Mol. Biol., 422(1): 109-123.

Laffer et al. (1996) "Molecular Characterization of Bip 1, a Monoclonal Antibody that Modulates IgE Binding to Birch Pollen Allergen, Bet v 1" J Immunol 157:4953-4962.

Langer (1990) "New Methods of Drug Delivery", Science 249:1527-1533.

Langer and Wise (eds.) (1984) "Medical Applications of Controlled Release" CRC Pres., Boca Raton, Florida, vol. 2, pp. 115-138.

Lebecque et al. (1997) "Immunological Characterization of Monoclonal Antibodies that Modulate Human IgE Binding to the Major Birch Pollen Allergen Bet v" Journal of Allergy and Clinical Immuno 99(3):374-384.

Levin et al. (2014) "Human IgE Against the Major Allergen Bet v 1—Defining an Epitope with Limited Cross-Reactivity Between Different PR-10 Family Proteins" Clinical & Experimental Allergy: Journal of the British Society for Allergy and Clinical Immunology 44(2):288-299.

"Liu et al. (2007) ""An essential role for RasGRP1 in mast cellfunction and IgE-mediated allergic response"" J Exp Med 204:93-103".

MacCllum et al. (1996) "Antibody-antigen Interactions: Contact Analysis and Binding Site Topography " J. Mol. Biol. 262:732-745.

Mariuzza et al. (1987) "The Structural Basis of Antigen-Antibody Recognition" Annu. Rev. Biophys. Chem. 16:139-159.

Markovic-Housley et al. (2003) "Crystal Structure of a Hypoallergenic Isoform of the Major Birch Pollen Allergen Bet v 1 and its Likely Biological Functions as a Plant Steroid Carrier" J Mol Biol. 325(1): 123-33.

Martin et al (1989) "Modeling Antibody Hypervariable Loops: A Combined Algorithm", Proc. Natl. Acad. Sci. USA 86:9268-9272.

Mordenti et al (1991) "Interspecies Scaling of Clearance and Volume of Distribution Data for Five Therapeutic Proteins", Pharmaceut. Res. 8(11):1351-1359.

Musidlowska-Persson et al. (2007) "Cloning and Sequencing of the Bet v 1—Homologous Allergen Fra a 1 in Strawberry (Fragaria ananassa) Shows the Presence of an Intron and Little Variability in Amino Acid Sequence" Molecular Immunology 44:1245-1252.

Nolte et al (2016) "Efficacy of House Dust Mite Sublingual Immunotherapy Tablet in North American Adolescents and Adults in a Randomized, Placebo-Controlled Trial", Journal of Allergy and Clinical Immunology, 138:1631-1638.

Pablos et al (2016) "Pollen Allergens for Molecular Diagnosis", Current Allergy and Asthma Reports, 16:31.

Padlan et al. (1995) "Identification of specificity-determining residues in antibodies" FASEB J. 9:133-139.

PCT International Search Report and Written Opinion received for PCT/US2018/035366, dated Oct. 22, 2018, 40pages.

Pearson(1994) "Using the FASTA Program to Search Protein and DNA Sequence Databases" Methods Mol. Biol. 24:307-331.

Pearson (2000) "Flexible Sequence Similarity Searching with the FASTA3 Program Package", Methods in Molecular Biology, 132:185-219.

Poosarla et al. (2017) "Computational De Novo Design of Antibodies Binding to a Peptide with High Affinity" Biotech. Bioeng. 114(6):1331-1342.

Powell et al. (1998) "Compendium of excipients for parenteral formulations" PDA J Pharm Sci Technol 52:238-311.

Reddy et al. (2000) "Elimination of Fc Receptor-Dependent Effector Functions of a Modified IgG4 Monocolonal Antibody to Human CD4" J. Immunol. 164: 1925-1933.

Reineke (2004) "Antibody Epitope Mapping Using Arrays of Synthetic Peptide" Methods Mol Biol 248:443-63.

Rosario and Bielory (2011) "Epidemiology of Allergic Conjunctivitis" Curr Opin Allergy Clin Immun 11(5):471-476.

(56) References Cited

OTHER PUBLICATIONS

Schenk et al (2011) "Proteomic Analysis of the Major Birch Allergen Bet v 1 Predicts Allergenicity for 15 Birch Species", Journal of Proteomics, 74:1290-1300.
Sefton (1987) "Implantable Pumps", CRC Crit. Rev. Biomed. Eng. 14(3):201-240.
Shield et al. (2002) "Lack of Fucose on Human IgG1 N-Linked Oligosaccharide Improves Binding to Human FcyRIII and Antibody-dependent Cellular Toxicity" JBC 277: 26733-26740.
Sinha (2013) "Current Overview of Allergens of Plant Pathogenesis Related Protein Families" The Scientific World Journal 2014:543195:1-19.
Spangfort et al. (2003) "Dominating IgE-Binding Epitope of Bet v 1, the Major Allergen of Birch Pollen, Characterized by X-ray Crystallography and Site-Directed Mutagenesis" J Immunol. 171(6): 3084-3090.
Taylor et al (1992) "A Transgenic Mouse That Expresses a Diversity of Human Sequence Heavy and Light Chain Immunoglobulins", Nucl. Acids Res. 20(23):6287-6295.
Taylor et al (2004) "Birch Pollen Rupture and the Release of Aerosols of Respirable Allergens" Clin Exp Allergy 34 (10):1591-1596.
Taylor et al (2007) "Links Between Pollen, Atopy and the Asthma Epidemic", International Archives of Allergy and Immunology, 144:162-170.
Vajdos et al. (2002) "Comprehensive Functional Maps of the Antigen-binding Site of an Anti-ErbB2 Antibody Obtained with Shotgun Scanning Mutagenesis" J Mol Biol 320:415-428.
Visco (1996) "Human IgG Monoclonal Antibodies that Modulate the Binding of Specific IgE to Birch Pollen Bet v 1" J Immunol 157(2):956-962.
Wallace and Dykewicz (2017) "Seasonal Allergic Rhinitis: A Focused Systematic Review and Practice Parameter Update" Curr Opin Allergy Clin Immun 17(4):286-294.
Wallace et al (2008) "The Diagnosis and Management of Rhinitis: An Updated Practice Parameter", Journal of Allergy and Clinical Immunology, 122:S1-84.
Wangorsch et al. (2015) "Identification of Sola l 4 as Bet v 1 Homologous Pathogenesis Related-10 Allergen in Tomato Fruits" Molecular Nutr. Food Res. 59:582-592.
Wei (2016) "The Efficacy and Safety of H1-Antihistamine versus Montelukast for Allergic Rhinitis: A Systematic Review and Meta-Analysis" Biomed Pharm 83:989-997.
Wu et al. (1987) "Receptor-Mediated in Vitro Gene Transformation by a Soluble DNA Carrier System*", J. Biol. Chem. 262(10):4429-4432.
Bostrom, et al. (2009) "Improving Antibody Binding Affinity and Specificity for Therapeutic Development", Methods Mol. Biol., 525:353-376.
Gonzales, et al. (2005) "Minimizing the Immunogenicity of Antibodies for Clinical Applications", Tumour Biol., 26 (1):31-43.
Wark and Hudson (2006) "Latest Technologies for the Enhancement of Antibody Affinity", Advanced Drug Delivery Reviews, 58(5-6):657-670.
Kunik et al. (2012) "Structural Consensus Among Antibodies Defines the Antigen Binding Site, "PLOS Computational Biology, 8(2):e1002388.
Kussie et al. (1994) "A Single Engineered Amino Acid Substitution Changes Antibody Fine Specificity," Journal of Immunology, 152(1):146-152.
Morris (1996) "Epitope Mapping of Protein Antiens by Completition ELISA," The Protein Protocols Handbook, Totowa, NJ, Human Press, pp. 595-600.
Panka et al.(1988) "Variable Region Framework Differences Result in Decreased or Increased Affinity of Variant Anti-digoxin Antibodies," Proc. Anti, Acad. Sci. USA, 85:3080-3084.
Rudikoff et al. (1982) "Single Amino Acid Substitution Altering Antigen-Binding Specificity," Proc. Natl, Acad. Sci. USA, 79:1979-1983.

* cited by examiner

METHODS OF TREATING ALLERGY USING ANTI-BET V 1 ANTIBODIES

This application claims priority to U.S. Provisional Patent Application Nos. 63/047,126, filed Jul. 1, 2020, and 63/129,253, filed Dec. 22, 2020, the entire contents of each of which are incorporated by reference herein.

FIELD OF THE INVENTION

Sequence Listing

A copy of the sequence listing is submitted concurrently with the specification electronically via EFS-Web as an ASCII formatted sequence listing with a file name of 10821 US01_Sequence_Listing_ST25, a creation date of Jun. 30, 2021, and a size of about 32 kilobytes. The sequence listing contained in this ASCII formatted document is part of the specification and is herein incorporated by reference in its entirety.

FIELD OF THE INVENTION

The present disclosure relates to the use of human antibodies that bind to Bet v 1 to treat or prevent allergic reactions and allergic diseases in a subject in need thereof.

BACKGROUND

Allergic rhinitis (AR) is an allergic disease characterized by one or more symptoms including sneezing, itching, nasal congestion, and rhinorrhea, and also often includes symptoms such as fatigue, malaise, irritability, and possibly neurocognitive deficits. Conjunctivitis is also common, reported in approximately 65% of persons with AR (Rosario and Bielory, *Current Opinion in Allergy and Clinical Immunology* 2011, 11:471-476). Allergic rhinitis affects approximately 100 million people in Europe and the incidence is increasing (Wallace et al, *Journal of Allergy and Clinical Immunology* 2008, 122:S1-84). People with AR may be allergic to pollens, molds, dust mites, and/or animal dander. Diagnosis of AR is confirmed by a positive history and evidence of immunoglobulin E (IgE)-mediated inflammation either by an allergen-specific positive skin prick test (SPT) and/or a positive allergen-specific IgE antibody test.

In Europe and the United States, clinically relevant sensitization to birch affects approximately 20% to 30% of the allergic population (see, e.g., Pablos et al, *Current Allergy and Asthma Reports* 2016, 16:31). Birch pollen contains a mix of allergenic and non-allergenic proteins; Bet v 1 is the most abundant allergenic pollen protein (Erler et al, *Proteomics* 2011 11:1486-1498; Schenk et al, *Journal of Proteomics* 2011, 74:1290-1300). Sensitization rates to 10821 USW
Bet v 1 among birch-allergic individuals reach >95%. Pollen grains are generally not observed to penetrate the lower airways due to larger particle size (>5 μm) and predominantly affect nasal and ocular symptoms. However, coughing and wheezing is not infrequent and has been associated with respirable concentrations of Bet v 1 detectable in the atmosphere, suggesting that pollen fragments may penetrate the lower airways and exacerbate asthma (see, e.g., Taylor et al, *Clinical and Experimental Allergy* 2004, 34:1591-1596; Taylor et al, *International Archives of Allergy and Immunology* 2007, 144:162-170). Moreover, mid-spring pollen exposure is associated with an increase in over-the-counter medicines for rhinitis and a peak in asthma-related emergency department visits; the strongest associations are with children aged 5 to 17 with allergies to birch, oak, beech, and ash pollen (Ito et al, *Environmental Health: A Global Access Science Source* 2015, 14:71). Up to 70% of people with pollen allergy also experience oral reactions to particular fresh fruits, vegetables, and nuts, namely, oral allergy syndrome (OAS), also known as pollen-food allergy. Oral allergy syndrome is not a separate food allergy but rather occurs because of cross-reactive epitopes present in pollen and associated foods; oral allergy syndrome symptoms typically manifest as itching of lips, mouth, and throat, but potentially involve lip and tongue swelling and angioedema (Bucher et al, *Allergy* 2004, 59:1272-1276), leading people to avoid these fresh fruits, vegetables, and nuts.

Recommendations for treating AR include allergen avoidance, medications that provide short-term relief of symptoms such as antihistamines and intra-nasal corticosteroids, and allergen-specific immunotherapy (SIT). While antihistamines and intra-nasal corticosteroids are widely used, up to about half of sufferers of AR report poor or only partial symptom control and short-term relief (see, e.g., Wallace et al, *Current Opinion in Allergy and Clinical Immunology* 2017, 17:286-294; Wei, *Biomedicine & Pharmacotherapy* 2016, 83:989-997). Specific immunotherapy is indicated when moderate to severe symptoms of AR persist despite the use of antihistamines and intra-nasal corticosteroids. Although the use of allergen-specific SIT is well established, both in subcutaneous immunotherapy (SCIT) and as sublingual immunotherapy (SLIT) tablets or drops, there are numerous limitations to SIT. For instance, the efficacy of SIT is moderate, resulting in approximately 20% to 30% improvement in allergic symptoms in people completing treatment as compared to those taking placebo, and can take at least 3 years to induce immune tolerance (see, e.g., Nolte et al, *Journal of Allergy and Clinical Immunology* 2016, 138:1631-1638). Additionally, the efficacy of SIT requires high adherence to prevent rhinitis symptoms upon allergen exposure. Side effects to SCIT occur in 40% to 50% of patients ranging from mild reactions (e.g., swelling, injection site reaction, de novo allergic response, and urticaria) to life-threatening reactions (e.g., asthma exacerbation and anaphylaxis) (see, e.g., Frew, *Journal of Allergy and Clinical Immunology* 2010, 125:S306-313). Additionally, asthma is a major risk factor for life-threatening systemic reactions to SCIT, and therefore moderate to severe asthma is a contraindication to SLCIT. Accordingly, there remains a need for safe and effective therapies for treating people with allergies.

BRIEF SUMMARY

In one aspect, methods of treating birch allergy in a subject are provided. In some embodiments, the method comprises administering to the subject one or more pharmaceutical compositions comprising:

(a) a first anti-Bet v 1 antibody or antigen-binding fragment thereof, wherein the first anti-Bet v 1 antibody comprises a heavy chain complementarity determining region (HCDR) 1 comprising the amino acid sequence of SEQ ID NO:2, an HCDR2 comprising the amino acid sequence of SEQ ID NO:3, an HCDR3 comprising the amino acid sequence of SEQ ID NO:4, a light chain complementarity determining region (LCDR) 1 comprising the amino acid sequence of SEQ ID NO:6, an LCDR2 comprising the amino acid sequence of SEQ ID NO:7, and an LCDR3 comprising the amino acid sequence of SEQ ID NO:8; and/or (b) a second anti-Bet v 1 antibody or antigen-binding fragment thereof, wherein the second anti-Bet v 1 antibody comprises an HCDR1 comprising the amino acid sequence of SEQ ID NO:12, an HCDR2 comprising the amino acid sequence of SEQ ID NO:13, an HCDR3 comprising the amino acid sequence of SEQ ID NO:14, an LCDR1 comprising the amino acid sequence of SEQ ID NO:16, an LCDR2 comprising the amino acid sequence of SEQ ID NO:17, and an LCDR3 comprising the amino acid sequence of SEQ ID NO:18; and/or (c) a third anti-Bet v 1 antibody or antigen-binding fragment thereof, wherein the third anti-Bet v 1 antibody comprises an HCDR1 comprising the amino acid sequence of SEQ ID NO:22, an HCDR2 comprising the amino acid sequence of SEQ ID NO:23, an HCDR3 comprising the amino acid sequence of SEQ ID NO:24, an LCDR1 comprising the amino acid sequence of SEQ ID NO:26, an LCDR2 comprising the amino acid sequence of SEQ ID NO:27, and an LCDR3 comprising the amino acid sequence of SEQ ID NO:28.

In another aspect, methods of reducing one or more symptoms of an allergic reaction to a Fagales allergen in a subject are provided. In some embodiments, the method comprises administering to the subject one or more pharmaceutical compositions comprising:

(a) a first anti-Bet v 1 antibody or antigen-binding fragment thereof, wherein the first anti-Bet v 1 antibody comprises an HCDR1 comprising the amino acid sequence of SEQ ID NO:2, an HCDR2 comprising the amino acid sequence of SEQ ID NO:3, an HCDR3 comprising the amino acid sequence of SEQ ID NO:4, an LCDR1 comprising the amino acid sequence of SEQ ID NO:6, an LCDR2 comprising the amino acid sequence of SEQ ID NO:7, and an LCDR3 comprising the amino acid sequence of SEQ ID NO:8; and/or (b) a second anti-Bet v 1 antibody or antigen-binding fragment thereof, wherein the second anti-Bet v 1 antibody comprises an HCDR1 comprising the amino acid sequence of SEQ ID NO:12, an HCDR2 comprising the amino acid sequence of SEQ ID NO:13, an HCDR3 comprising the amino acid sequence of SEQ ID NO:14, an LCDR1 comprising the amino acid sequence of SEQ ID NO:16, an LCDR2 comprising the amino acid sequence of SEQ ID NO:17, and an LCDR3 comprising the amino acid sequence of SEQ ID NO:18; and/or (c) a third anti-Bet v 1 antibody or antigen-binding fragment thereof, wherein the third anti-Bet v 1 antibody comprises an HCDR1 comprising the amino acid sequence of SEQ ID NO:22, an HCDR2 comprising the amino acid sequence of SEQ ID NO:23, an HCDR3 comprising the amino acid sequence of SEQ ID NO:24, an LCDR1 comprising the amino acid sequence of SEQ ID NO:26, an LCDR2 comprising the amino acid sequence of SEQ ID NO:27, and an LCDR3 comprising the amino acid sequence of SEQ ID NO:28.

In some embodiments, the Fagales allergen is Bet v 1. In some embodiments, the subject is sensitized to Bet v 1 and to at least one other Fagales allergen. In some embodiments, the at least one other Fagales allergen is alder, hazel, oak, hornbeam, hop-hornbeam, beech, chestnut, hazelnut, or apple.

In another aspect, methods of treating a subject having seasonal or perennial allergy associated with birch and cross-reacting pollens are provided. In some embodiments, the subject has moderate-to-severe seasonal allergy or moderate-to-severe perennial allergy. In some embodiments, the method comprises administering to the subject one or more pharmaceutical compositions comprising:

(a) a first anti-Bet v 1 antibody or antigen-binding fragment thereof, wherein the first anti-Bet v 1 antibody comprises an HCDR1 comprising the amino acid sequence of SEQ ID NO:2, an HCDR2 comprising the amino acid sequence of SEQ ID NO:3, an HCDR3 comprising the amino acid sequence of SEQ ID NO:4, an LCDR1 comprising the amino acid sequence of SEQ ID NO:6, an LCDR2 comprising the amino acid sequence of SEQ ID NO:7, and an LCDR3 comprising the amino acid sequence of SEQ ID NO:8; and/or (b) a second anti-Bet v 1 antibody or antigen-binding fragment thereof, wherein the second anti-Bet v 1 antibody comprises an HCDR1 comprising the amino acid sequence of SEQ ID NO:12, an HCDR2 comprising the amino acid sequence of SEQ ID NO:13, an HCDR3 comprising the amino acid sequence of SEQ ID NO:14, an LCDR1 comprising the amino acid sequence of SEQ ID NO:16, an LCDR2 comprising the amino acid sequence of SEQ ID NO:17, and an LCDR3 comprising the amino acid sequence of SEQ ID NO:18; and/or (c) a third anti-Bet v 1 antibody or antigen-binding fragment thereof, wherein the third anti-Bet v 1 antibody comprises an HCDR1 comprising the amino acid sequence of SEQ ID NO:22, an HCDR2 comprising the amino acid sequence of SEQ ID NO:23, an HCDR3 comprising the amino acid sequence of SEQ ID NO:24, an LCDR1 comprising the amino acid sequence of SEQ ID NO:26, an LCDR2 comprising the amino acid sequence of SEQ ID NO:27, and an LCDR3 comprising the amino acid sequence of SEQ ID NO:28.

For the methods disclosed herein, in some embodiments the pharmaceutical composition comprises the first anti-Bet v 1 antibody. In some embodiments, the pharmaceutical composition comprises the second anti-Bet v 1 antibody. In some embodiments, the pharmaceutical composition comprises the third anti-Bet v 1 antibody. In some embodiments, the pharmaceutical composition comprises the first anti-Bet v 1 antibody and the second anti-Bet v 1 antibody. In some embodiments, the pharmaceutical composition comprises the first anti-Bet v 1 antibody and the third anti-Bet v 1 antibody. In some embodiments, the pharmaceutical composition comprises the second anti-Bet v 1 antibody and the third anti-Bet v 1 antibody. In some embodiments, the pharmaceutical composition comprises the first anti-Bet v 1 antibody, the second anti-Bet v 1 antibody, and the third anti-Bet v 1 antibody.

In some embodiments, the anti-Bet v 1 antibodies are provided in a single pharmaceutical composition. In some embodiments, the anti-Bet v 1 antibodies are provided in more than one pharmaceutical composition, e.g., each anti-Bet v 1 antibody in a separate pharmaceutical composition.

In some embodiments, the pharmaceutical composition(s) comprises the anti-Bet v 1 antibody or antibodies (e.g., each of the first anti-Bet v 1 antibody, the second anti-Bet v 1 antibody, and the third anti-Bet v 1 antibody) at an independently selected dose of about 5 mg to about 500 mg. In some embodiments, the pharmaceutical composition(s) comprises the anti-Bet v 1 antibody or antibodies (e.g., each of the first anti-Bet v 1 antibody, the second anti-Bet v 1 antibody, and the third anti-Bet v 1 antibody) at an independently selected dose of about 50 mg, about 100 mg, about 150 mg, about 200 mg, about 250 mg, about 300 mg, about 350 mg, about 400 mg, about 450 mg, or about 500 mg. In some embodiments, the pharmaceutical composition(s) comprises each of the first anti-Bet v 1 antibody, the second anti-Bet v 1 antibody, and the third anti-Bet v 1 antibody at a dose of about 50 mg. In some embodiments, the pharmaceutical composition(s) comprises each of the first anti-Bet v 1 antibody, the second anti-Bet v 1 antibody, and the third anti-Bet v 1 antibody at a dose of about 150 mg. In some embodiments, the pharmaceutical composition(s) comprises each of the first anti-Bet v 1 antibody, the second anti-Bet v 1 antibody, and the third anti-Bet v 1 antibody at a dose of about 300 mg.

In some embodiments, the anti-Bet v 1 antibody or antibodies, or the pharmaceutical composition comprising the anti-Bet v 1 antibody or antibodies, is administered subcutaneously. In some embodiments, the anti-Bet v 1 antibody or antibodies, or the pharmaceutical composition comprising the anti-Bet v 1 antibody or antibodies, is administered intravenously.

In some embodiments, a single dose of the anti-Bet v 1 antibody or antibodies, or the pharmaceutical composition comprising the anti-Bet v 1 antibody or antibodies, is administered. In some embodiments, the anti-Bet v 1 antibody or antibodies, or the pharmaceutical composition comprising the anti-Bet v 1 antibody or antibodies, is administered once before the start of pollen season.

In some embodiments, the first anti-Bet v 1 antibody comprises a heavy chain variable region (HCVR) comprising the amino acid sequence of SEQ ID NO:1 and a light chain variable region (LCVR) comprising the amino acid sequence of SEQ ID NO:5. In some embodiments, the first anti-Bet v 1 antibody comprises a heavy chain comprising the amino acid sequence of SEQ ID NO:9 and a light chain comprising the amino acid sequence of SEQ ID NO:10.

In some embodiments, the second anti-Bet v 1 antibody comprises an HCVR comprising the amino acid sequence of SEQ ID NO:11 and an LCVR comprising the amino acid sequence of SEQ ID NO:15. In some embodiments, the second anti-Bet v 1 antibody comprises a heavy chain comprising the amino acid sequence of SEQ ID NO:19 and a light chain comprising the amino acid sequence of SEQ ID NO:20.

In some embodiments, the third anti-Bet v 1 antibody comprises an HCVR comprising the amino acid sequence of SEQ ID NO:21 and an LCVR comprising the amino acid sequence of SEQ ID NO:25. In some embodiments, the third anti-Bet v 1 antibody comprises a heavy chain comprising the amino acid sequence of SEQ ID NO:29 and a light chain comprising the amino acid sequence of SEQ ID NO:30.

In some embodiments, treatment with the pharmaceutical composition:
- reduces a subject's Total Nasal Symptom Score (TNSS);
- reduces a subject's Total Ocular Symptom Score (TOSS);
- reduces a subject's Total Symptom Score (TSS);
- reduces a subject's Daily Medication Score (DMS);
- reduces a subject's Combined Symptom and Medication Score (CSMS);
- reduces a subject's birch skin prick test (SPT) mean wheal diameter; and/or
- increases a subject's number of "well days" in which rescue medication is not utilized and the subject's TSS is of 18.

In some embodiments, the TNSS, TOSS, TSS, DMS, CSMS, SPT mean wheal diameter, and/or number of well days is measured over at least 28, 57, 85, or 113 days. In some embodiments, the TNSS, TOSS, TSS, DMS, CSMS, SPT mean wheal diameter, and/or number of well days is measured over the duration of birch pollen season.

In some embodiments, treatment with the pharmaceutical composition reduces allergic rhinitis symptoms in the subject. In some embodiments, treatment with the pharmaceutical composition: reduces a subject's Total Nasal Symptom Score (TNSS) AUC (0-1 hr) after nasal allergen challenge (NAC) (e.g., by at least about 15%, 20%, 25%, 30%, 35%, 40%, 45%, 50% or more), relative to a baseline TNSS AUC (0-1 hr) value after NAC for the subject prior to the onset of treatment; and/or reduces a subject's peak TNSS after NAC (e.g., by at least about 15%, 20%, 25%, 30%, 35%, 40%, 45%, 50% or more), relative to a baseline peak TNSS value after NAC for the subject prior to the onset of treatment.

In some embodiments, administration of a single dose of the pharmaceutical composition: reduces a subject's TNSS AUC (0-1 hr) after NAC by at least about 20% for at least two months after the pharmaceutical composition is administered; and/or reduces a subject's peak TNSS after NAC by at least about 25% for at least two months after the pharmaceutical composition is administered.

In some embodiments, treatment with the pharmaceutical composition reduces allergic conjunctivitis symptoms in the subject. In some embodiments, treatment with the pharmaceutical composition: reduces a subject's Total Ocular Symptom Score (TOSS) (e.g., by at least about 15%, 20%, 25%, 30%, 35%, 40%, 45%, 50% or more), relative to a baseline TOSS value for the subject prior to the onset of treatment; and/or reduces a subject's TOSS AUC (0-1 hr) after NAC (e.g., by at least about 15%, 20%, 25%, 30%, 35%, 40%, 45%, 50% or more), relative to a baseline TOSS AUC (0-1 hr) value after NAC for the subject prior to the onset of treatment.

In some embodiments, treatment with the pharmaceutical composition reduces a subject's combined symptom and medication score (CSMS) during birch pollen season (e.g., by at least about 10%, 15%, 20%, 25%, 30%, 35%, 40%, 45%, 50% or more), relative to a baseline CSMS for the subject prior to the onset of treatment or a control CSMS.

In some embodiments, treatment with the pharmaceutical composition improves peak nasal inspiratory flow (PNIF) in the subject (e.g., by at least about 25%, 30%, 35%, 40%, 45%, 50%, 55%, 60%, 65%, 70%, 75% or more), relative to a baseline PNIF value for the subject prior to the onset of treatment.

In some embodiments, treatment with the pharmaceutical composition reduces birch sensitization in the subject (e.g., by at least about 30%, 40%, 50%, 60%, 70%, 80%, 90% or more) as measured by a skin prick test (SPT) with a birch allergen extract. In some embodiments, administration of a single dose of the pharmaceutical composition reduces birch sensitization in the subject by at least about 60% or more for at least two months (e.g., at least three months, at least four months, at least five months, or at least six months) after the pharmaceutical composition is administered.

In some embodiments, the subject to be treated has a baseline serum allergen-specific IgE level 0.35 kUa/L for the allergen (e.g., birch tree pollen, Bet v 1 allergen, or Fagales allergen). In some embodiments, the subject to be treated has a baseline positive SPT with an allergen (e.g., birch allergen extract or Fagales allergen).

In another aspect, a cocktail comprising two or more anti-Bet v 1 antibodies or antigen-binding fragments thereof for use in a method of treating birch allergy in a subject is provided. In some embodiments, the method comprises administering the cocktail as disclosed herein to a subject in need thereof (e.g., a subject having birch allergy).

In another aspect, the use of a cocktail comprising two or more anti-Bet v 1 antibodies or antigen-binding fragments thereof in the manufacture of a medicament for use in a method of treating birch allergy in a subject is provided. In some embodiments, the method comprises administering the cocktail as disclosed herein to a subject in need thereof (e.g., a subject having birch allergy).

In another aspect, a cocktail comprising two or more anti-Bet v 1 antibodies or antigen-binding fragments thereof for use in a method of reducing one or more symptoms of an allergic reaction to a Fagales allergen in a subject is provided. In some embodiments, the method comprises administering the cocktail as disclosed herein to a subject in need thereof (e.g., a subject having one or more symptoms of an allergic reaction to a Fagales allergen).

In another aspect, the use of a cocktail comprising two or more anti-Bet v 1 antibodies or antigen-binding fragments thereof in the manufacture of a medicament for use in a method of reducing one or more symptoms of an allergic reaction to a Fagales allergen in a subject is provided. In some embodiments, the method comprises administering the cocktail as disclosed herein to a subject in need thereof (e.g., a subject having one or more symptoms of an allergic reaction to a Fagales allergen).

In another aspect, a cocktail comprising two or more anti-Bet v 1 antibodies or antigen-binding fragments thereof for use in a method of treating a subject having seasonal or perennial allergy associated with birch and cross-reacting pollens are provided. In some embodiments, the method comprises administering the cocktail as disclosed herein to a subject in need thereof (e.g., a subject having seasonal or perennial allergy associated with birch and cross-reacting pollens are provided).

In another aspect, the use of a cocktail comprising two or more anti-Bet v 1 antibodies or antigen-binding fragments thereof in the manufacture of a medicament for use in a method of treating a subject having seasonal or perennial allergy associated with birch and cross-reacting pollens are provided. In some embodiments, the method comprises administering the cocktail as disclosed herein to a subject in need thereof (e.g., a subject having seasonal or perennial allergy associated with birch and cross-reacting pollens are provided).

Other embodiments will be apparent from a review of the ensuing detailed description.

Figure 8:
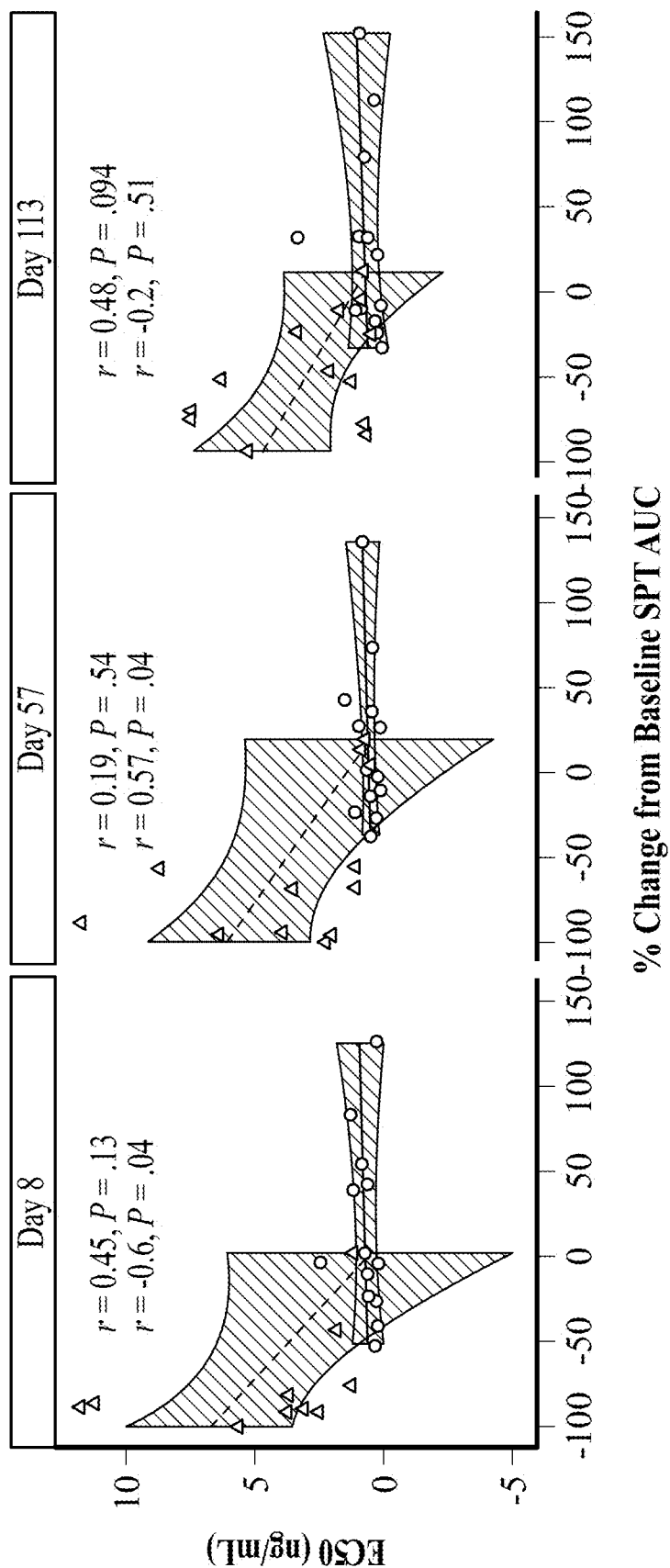

FIG. 8 shows a correlation between suppression of basophil activation (EC50 value) and reduction in skin prick test (SPT) in patients treated with an anti-Bet v 1 antibody cocktail. Inverse correlations were observed between birch BAT EC50 and percent change in birch SPT (Mean wheal diameter) AUC on Day 8 (r=−0.6, p=0.04) and Day 57 (r=−0.57, p=0.04). No significant correlation was observed in subjects who received placebo.

Figure 9A:
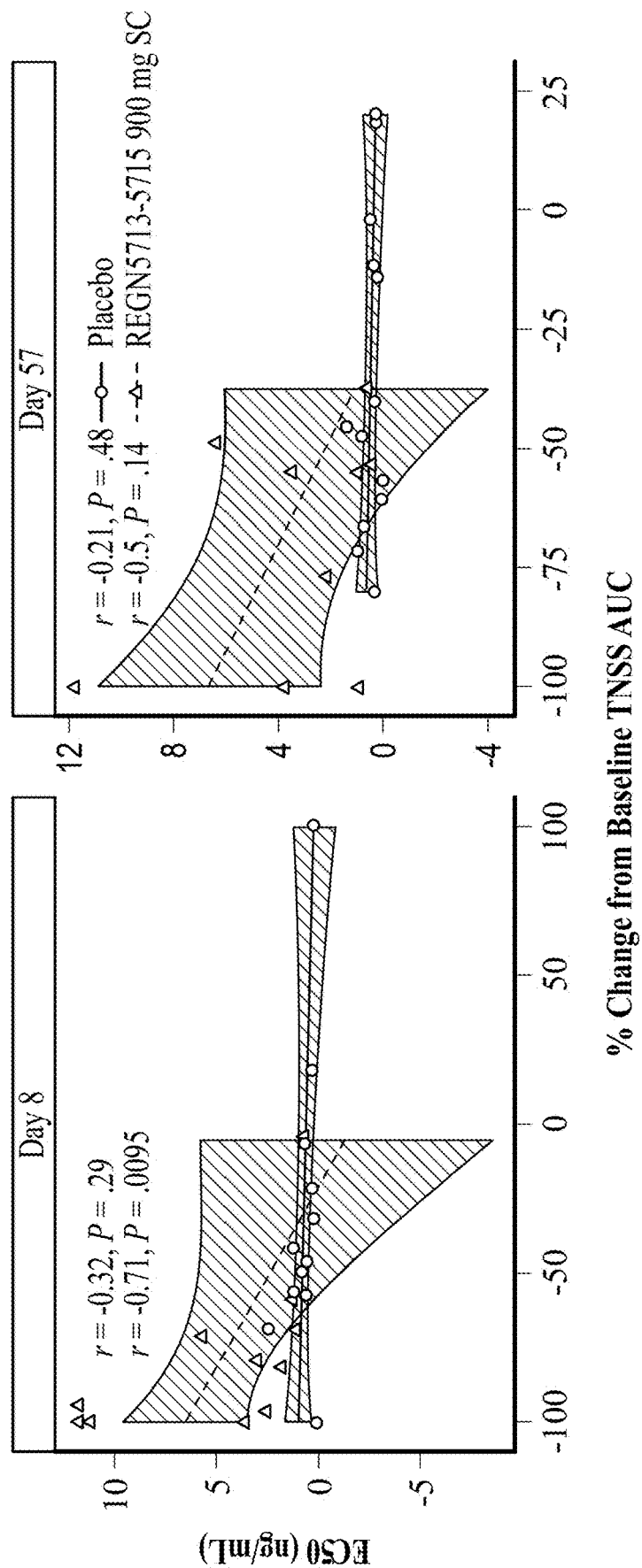
Figure 9B:
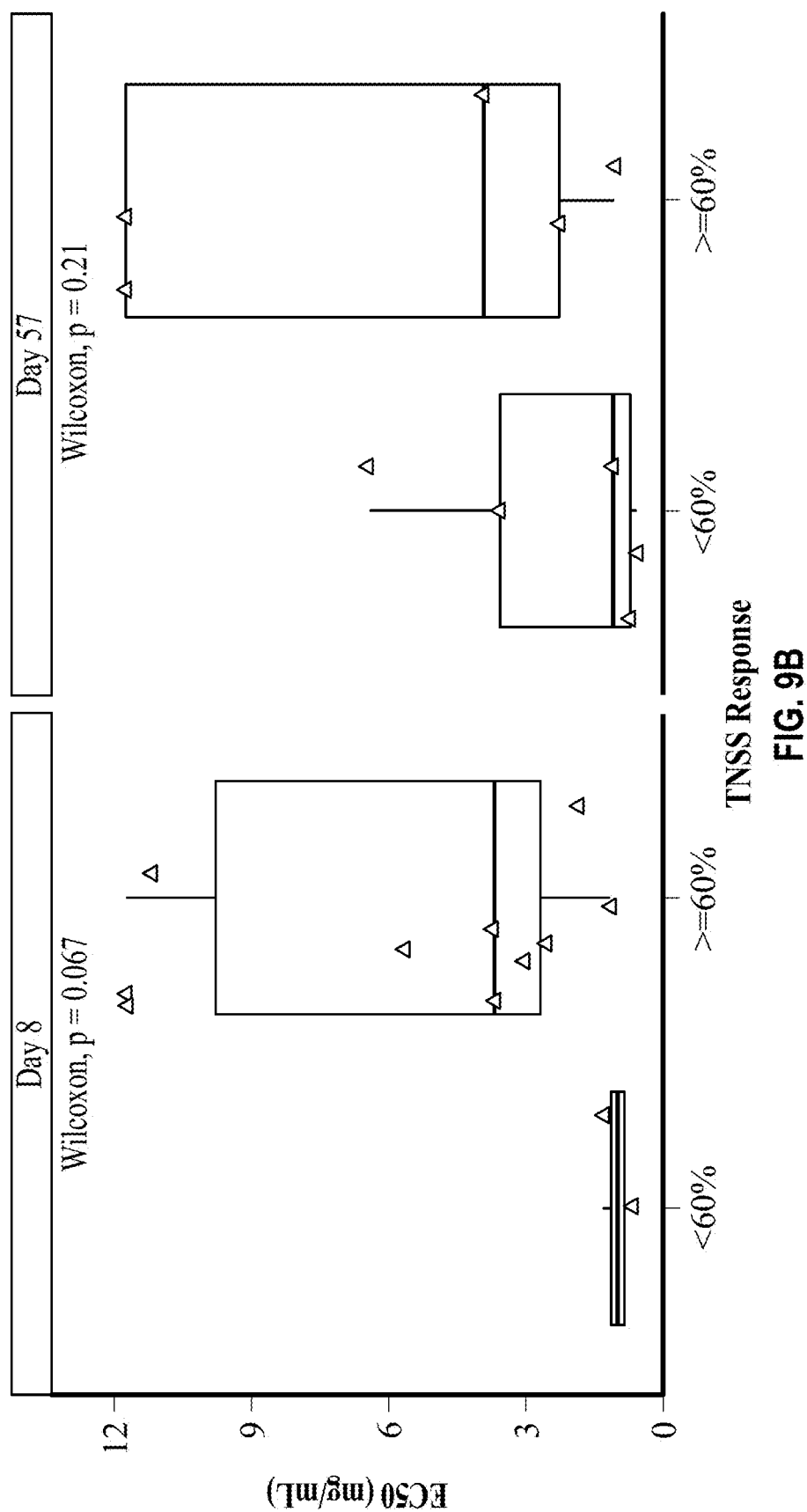

FIGS. 9A-9B show a correlation between suppression of basophil activation (EC50 value) and TNSS response (percent change in $TNSS_{(0-1\ hr)}$ AUC) in patients treated with an anti-Bet v 1 antibody cocktail. (A) Statistically significant inverse correlation of EC50 value with % improvement in $TNSS_{(0-1\ hr)}$ AUC was observed on day 8 (r=−0.71, p=0.0095). No significant correlation was observed in subjects who received placebo. (B) Responder analysis of the active treatment group ($TNSS_{(0-1\ hr)}$ AUC reduction ≥60% vs. <60%).

DETAILED DESCRIPTION

Definitions

Before the present invention is described, it is to be understood that the invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs.

As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

As used herein, the terms "treat," "treating," or the like, mean to alleviate symptoms, eliminate the causation of symptoms either on a temporary or permanent basis, or to prevent or slow the appearance of symptoms of the named disorder or condition.

The term "Bet v 1", as used herein, refers to a Bet v 1 protein, either in natural/native form or recombinantly produced. The natural Bet v 1 protein is approximately 17 kD and exists as a 7 stranded anti-parallel β-sheet (β1-β7), two short α-helices (α1 and α2) connecting β1 and β2, a long C-terminal α-helix (α3), and the glycine-rich loop motif between β2 and β3 (Kofler et al., J. Mol. Biol. 2012, 422(1): 109-123). In some embodiments, a Bet v 1 protein comprises the amino acid sequence of SEQ ID NO:31. In some embodiments, a Bet v 1 protein comprises a naturally occurring or recombinantly produced form that comprises one or more amino acid substitutions, deletions, or additions relative to SEQ ID NO:31. For example, in some embodiments, a Bet v 1 protein comprises the amino acid sequence of SEQ ID NO:32 (the Bet v 1 amino acid sequence from Uniprot: P15494).

The term "Bet v 1 fragment," as used herein, refers to a polypeptide having at least one antigenic site of Bet v 1. In some embodiments, a Bet v 1 fragment is a polypeptide having at least two antigen sites of Bet v 1. In some embodiments, the antigenic sites are covalently linked. In some embodiments, the antigenic sites are linked by at least one peptide bond. In one embodiment, the two antigenic sites are linked by at least one peptide bond and a spacer between the antigenic sites. Exemplary Bet v 1 fragments are disclosed in WO 2018/222854, incorporated by reference herein.

The term "antibody," as used herein, refers to an antigen-binding molecule or molecular complex comprising a set of complementarity determining regions (CDRs) that specifically bind to or interact with a particular antigen (e.g., Bet v 1). The term "antibody," as used herein, includes immunoglobulin molecules comprising four polypeptide chains, two heavy (H) chains and two light (L) chains inter-connected by disulfide bonds, as well as multimers thereof (e.g., IgM). In a typical antibody, each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In some embodiments, the FRs of the antibody (or antigen-binding portion thereof) may be identical to the human germline sequences, or may be naturally or artificially modified. An amino acid consensus sequence may be defined based on a side-by-side analysis of two or more CDRs.

The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g., monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

The term "antibody," as used herein, also includes multispecific (e.g., bispecific) antibodies. A multispecific antibody or antigen-binding fragment of an antibody will typically comprise at least two different variable domains, wherein each variable domain is capable of specifically binding to a separate antigen or to a different epitope on the same antigen. Any multispecific antibody format may be adapted for use in the context of an antibody or antigen-binding fragment of an antibody of the present disclosure using routine techniques available in the art. For example, the present disclosure includes methods comprising the use of bispecific antibodies wherein one arm of an immunoglobulin is specific for Bet v 1 or a fragment thereof, and the other arm of the immunoglobulin is specific for a second therapeutic target or is conjugated to a therapeutic moiety. Exemplary bispecific formats that can be used in the context of the present disclosure include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, Duobody, IgG1/IgG2, dual acting Fab (DAF)-IgG, and Mab$^e$ bispecific formats (see, e.g., Klein et al. 2012, mAbs 4:6, 1-11, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al., *J. Am. Chem. Soc.* [Epub: Dec. 4, 2012]).

The term "human antibody," as used herein, is intended to include antibodies having variable and constant regions derived from human germline immunoglobulin sequences. The human antibodies of the disclosure may nonetheless include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody," as used herein, is not intended to include antibodies in which CDR sequences derived from the germline of another mammalian species, such as a mouse, have been grafted onto human framework sequences.

The term "recombinant human antibody," as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see, e.g., Taylor et al. (1992) *Nucl. Acids Res.* 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

An "isolated antibody" refers to an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody." An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

The term "specifically binds," or the like, means that an antibody or antigen-binding fragment thereof forms a complex with an antigen that is relatively stable under physiologic conditions. Specific binding can be characterized by an equilibrium dissociation constant of at least about $1 \times 10^{-6}$ M or less (e.g., a smaller $K_D$ denotes a tighter binding). Methods for determining whether an antibody specifically binds to an antigen are well known in the art and include, for example, equilibrium dialysis, surface plasmon resonance, and the like. In some embodiments, specific binding is measured in a surface plasmon resonance assay. An isolated antibody that specifically binds an antigen from one species may or may not have cross-reactivity to other antigens, such as an orthologous antigen from another species.

The term "$K_D$," as used herein, refers to the equilibrium dissociation constant of a particular antibody-antigen interaction.

The term "surface plasmon resonance," as used herein, refers to an optical phenomenon that allows for the analysis of real-time biomolecular interactions by detection of alterations in protein concentrations within a biosensor matrix, for example using the BIACORE™ system (Pharmacia Biosensor AB, Uppsala, Sweden and Piscataway, N.J.).

The term "epitope," as used herein, refers to an antigenic determinant that interacts with a specific antigen binding site in the variable region of an antibody molecule known as a paratope. A single antigen may have more than one epitope. Thus, different antibodies may bind to different areas on an antigen and may have different biological effects. The term "epitope" also refers to a site on an antigen to which B and/or T cells respond. It also refers to a region of an antigen that is bound by an antibody. Epitopes may be either linear or discontinuous (e.g., conformational). A linear epitope is one produced by adjacent amino acid residues in a polypeptide chain. A conformational epitope is produced by spatially juxtaposed amino acids from different segments of the linear polypeptide chain. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics. Epitopes may also be defined as structural or functional. Functional epitopes are generally a subset of the structural epitopes and have those residues that directly contribute to the affinity of the interaction. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or at least 8-10 amino acids in a unique spatial conformation.

The terms "substantial identity" and "substantially identical," as used with reference to a nucleic acid or fragment thereof, indicates that, when optimally aligned with appropriate nucleotide insertions or deletions with another nucleic acid (or its complementary strand), there is nucleotide sequence identity in at least about 90%, e.g., at least 91%, 92%, 93%, 94%, 95%, 96%, 97%, 98% or 99%, of the nucleotide bases, as measured by any well-known algorithm of sequence identity, such as FASTA, BLAST or GAP, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the terms "substantial identity" and "substantially identical" mean that two peptide sequences, when optimally aligned, share at least about 90% sequence identity, e.g., at least 90%, 91%, 92%, 93%, 94%, 95%, 96%, 97%, 98% or 99% sequence identity. In some embodiments, residue positions that are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein.

Sequence similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson, 2000 supra). Another preferred algorithm when comparing a sequence of the present disclosure to a database containing a large number of sequences from different organisms is the computer program BLAST, especially BLASTP or TBLASTN, using default parameters. (See, e.g., Altschul et al., 1990, *J. Mol. Biol.* 215: 403-410 and 1997 *Nucleic Acids Res.* 25:3389-3402).

As used herein, the terms "allergic response," "allergic reaction," "allergic symptom," and the like, include one or more signs or symptoms selected from the group consisting of urticaria (e.g., hives), angioedema, rhinitis, asthma, vomiting, sneezing, runny nose, sinus inflammation, watery eyes, wheezing, bronchospasm, reduced peak expiratory flow (PEF), gastrointestinal distress, flushing, swollen lips, swollen tongue, reduced blood pressure, anaphylaxis, and organ dysfunction/failure. An "allergic response," "allergic reaction," "allergic symptom," etc., also includes immunological responses and reactions such as, e.g., increased IgE production and/or increased allergen-specific immunoglobulin production.

The term "allergen" refers to a substance, chemical, particle or composition that is capable of stimulating an allergic response in a susceptible individual. Allergens may be contained within or derived from a food item such as, e.g., dairy products (e.g., cow's milk), egg, celery, sesame, wheat, soy, fish, shellfish, sugars (e.g., sugars present on meat such as alpha-galactose), peanuts, other legumes (e.g., beans, peas, soybeans, etc.), and tree nuts. Alternatively, an allergen may be contained within or derived from a non-food item such as, e.g., dust (e.g., containing dust mite), pollen, insect venom (e.g., venom of bees, wasps, mosquitos, fire ants, etc.), mold, animal fur, animal dander, wool, latex, metals (e.g., nickel), household cleaners, detergents, medication, cosmetics (e.g., perfumes, etc.), drugs (e.g., penicillin, sulfonamides, salicylate, etc.), therapeutic monoclonal antibodies (e.g., cetuximab), ragweed, grass and birch. In some embodiments, an allergen is birch pollen or is contained within or derived from birch, e.g., a Bet v 1 protein. The terms "allergen" and "antigen" are used interchangeably through the disclosure.

As used herein, the term "subject in need thereof" refers to a human or non-human mammal that (i) exhibits one or more symptoms or indicia of allergy (e.g., birch allergy), (ii) has been diagnosed with allergy to an allergen (e.g., birch pollen allergen); and/or (iii) is at an increased risk for developing an allergy or an allergic response to an allergen (e.g., birch allergy or allergic response). In certain embodiments, the term includes subjects that show allergen sensitization to one or more allergens (e.g., birch allergens or a component thereof such as Bet v 1 protein). In some embodiments, a subject is sensitized to an allergen (e.g., birch allergen or Bet v 1 protein) if the subject exhibits a level of allergen-specific IgE for the allergen that is 0.35 kU/L. In certain embodiments, a subject in need of treatment according to the methods of the present disclosure is a subject having an elevated level of one or more serum biomarkers including, but not limited to, total IgE, allergen-specific IgE (e.g., birch pollen IgE or Bet v 1 IgE), thymus and activation-regulated chemokine (TARC), and eotaxin. For example, in some embodiments, the methods of the present disclosure comprise administering an anti-Bet v 1 antibody or antibody cocktail to patients with elevated levels of allergen-specific IgE (e.g., a subject having a birch pollen or Bet v 1 IgE level 0.35 kU/L). The terms "subject" and "patient" are used interchangeably herein.

The term "subject in need thereof" may also include, e.g., subjects who have a concomitant allergy or other condition. For example, in some embodiments a subject having a birch allergy may also have oral allergy syndrome. In some embodiments, a subject to be treated is a subject having a birch allergy and an allergy to one or more other Fagales order allergens. Fagales order allergens, or "Fagales allergens," as used herein, include but are not limited to birch pollen (Bet v 1), alder pollen (Aln g1 and Aln g4), hazel pollen (Cor a1, Cor a2, Cor a8, Cor a9, Cor a10, Cor a11, Cor a12, Cor a13, and Cor a14), hornbeam pollen (Car b1), hop-hornbeam pollen (Ost c1), chestnut pollen (Cas s1, Cas s5, Cas s8, and Cas s9), beech pollen (Fag s1) and white oak pollen (Que a1 and Que a2). A person of skill in the art will recognize that Bet v 1-related allergens (also referred to as "Fagales group 1" allergens or "PR-10 allergens") are also found in foods such as apple (Mal d 1), apricot (Pru ar 1), carrot (Dau c 1), celery (Api g 1), cherry (Pru av 1), chestnut (Cas s 1), hazelnut (Cor a 1), kiwi (Act c 8, Act d 8, and Act d 11), mungbean (Vig r 1), peanut (Ara h 8), pear (Pyr c 1), raspberry (Rub i 1), soybean (Gly m 4), strawberry (Fra a 1), tomato (Sola l 4), and walnut (Jug r 5). See, Carlson, *Annals of Allergy, Asthma & Immunology* 2019, 123:P359-365. Thus, the term "Fagales allergen" includes not only pollen allergens but also food allergens. In some embodiments, the subject has an elevated level of allergen-specific IgE (e.g., an allergen-specific IgE level≥0.35 kU/L) to birch pollen (e.g., birch pollen extract) or a Bet v 1 allergen and to one or more other Fagales allergens.

Introduction

As described herein, monoclonal antibody cocktails have been developed against Bet v 1, the major birch tree allergen. It is hypothesized that high-affinity allergen-specific monoclonal IgG antibodies can be administered as a form of providing "passive immunity" to the allergen. Pre-clinical studies have demonstrated that the anti-Bet v 1 antibodies REGN5713, REGN5714, and REGN5715 bind independently and non-competitively to the Bet v 1 allergen. Data also indicate that optimal binding inhibition of Bet v 1 to human polyclonal IgE occurs when all three antibodies are administered together, resulting in a reduction of in vitro effector cell degranulation and subsequent Type 1 hypersensitivity reaction. Without being bound to a particular theory, this activity of the anti-Bet v 1 antibodies is expected to prevent the resulting inflammatory cascade that triggers an allergic reaction in response to birch tree allergen and potentially cross-reacting allergens.

The anti-Bet v 1 antibody cocktails disclosed herein are advantageous over currently available therapies, such as allergen-specific immunotherapy (SIT), in at least several aspects. For example, blocking antibody cocktails are expected to be safer as the allergic patient is not exposed to native allergen; offer more predictable efficacy; offer more convenience, as a single dose may prevent allergic symptoms for an entire birch group and birch homologous group during allergy season; broaden the pool of patients who are able to receive the therapy (e.g., such as asthmatics who may have previously been contraindicated to receive SIT); and have a faster onset of action. As described herein, the anti-Bet v 1 antibodies provide a rapid and durable reduction in allergic symptoms in patients having a birch allergy.

Therapeutic Methods

In one aspect, methods for treating birch allergy or for treating, preventing, or ameliorating one or more symptoms of birch allergy in a subject are provided. In another aspect, methods for treating, preventing, or ameliorating seasonal or perennial allergy (e.g., moderate to severe seasonal or perennial allergy) to birch and/or birch cross-reacting pollens are provided. In some embodiments, the methods comprise administering to the subject one or more doses of an anti-Bet v 1 antibody or cocktail of anti-Bet v 1 antibodies (e.g., a pharmaceutical composition comprising one or more anti-Bet v 1 antibodies).

In some embodiments, a subject to be treated has a history of birch tree pollen-triggered allergic rhinitis symptoms with or without conjunctivitis. In some embodiments, a subject to be treated has been diagnosed with a positive skin prick test (SPT) with a birch tree pollen extract. In some embodiments, the subject has a positive SPT with a mean wheal diameter mm greater than a negative control. In some embodiments, a subject to be treated has been diagnosed with a positive allergen-specific IgE test for birch tree pollen (e.g., birch pollen extract) and/or a Bet v 1 antigen of ≥0.35 kU/L.

In some embodiments, a subject to be treated is an adult. In some embodiments, the subject has a concomitant disease or condition. Non-limiting examples of concomitant diseases or conditions include allergy (e.g., allergy to one or more food allergens and/or allergy to one or more non-food allergens such as aeroallergens), oral allergy syndrome, and asthma. In some embodiments, the subject has asthma. In some embodiments, the subject has birch triggered asthma. In some embodiments, the subject has an allergy to birch allergen and one or more tree homologues (e.g., a Fagales allergen).

In some embodiments, a subject to be treated has a history of birch tree pollen-triggered allergic rhinitis symptoms with or without asthma. In some embodiments, a subject to be treated has a history of birch tree pollen-triggered allergic rhinitis symptoms with or without conjunctivitis with or without asthma.

In some embodiments, a subject to be treated has an altered level of one or more biomarkers of allergic rhinitis. In some embodiments, the biomarker is associated with Type 2 immune activity and/or is an allergen-specific biomarker. In some embodiments, the biomarker is a serum biomarker. In some embodiments, the biomarker is total IgE, allergen-specific IgG4, or thymus and activation-regulated chemokine (TARC).

In some embodiments, treatment with one or more anti-Bet v 1 antibodies as disclosed herein results in an improvement in one or more symptoms of birch allergy or an improvement in a condition associated with birch allergy. In some embodiments, treatment according to the methods disclosed herein improves one or more symptoms of allergic rhinitis in a subject. As used herein, "improving allergic rhinitis symptoms" includes reducing the severity or duration of or eliminating one or more symptoms of allergic rhinitis in the subject, such as but not limited to sneezing, itching (of nose, eyes, ears, or palate), rhinorrhea, postnasal drip, congestion, anosmia, headache, earache, tearing, red eyes, eye swelling, and fatigue. In some embodiments, a reduction in allergic rhinitis symptoms is measured by Total Nasal Symptom Score (TNSS). TNSS is a patient-reported composite symptom assessment of congestion, itching, rhinorrhea and sneezing in which patient-assessed symptom scores are assigned for each category for a given time point, using a four point scale (0-3), where 0 indicates no symptoms, a score of 1 for mild symptoms that are easily tolerated, 2 for awareness of symptoms which are bothersome but tolerable and 3 is reserved for severe symptoms that are hard to tolerate and interfere with daily activity. TNSS is calculated by adding the score for each of the symptoms to a total out of 12. In some embodiments, a TNSS score is measured after nasal allergen challenge (NAC) with an allergen. In some embodiments, a baseline TNSS score is measured for a subject (e.g., during a screening visit prior to the start of treatment).

In some embodiments, treatment results in an improvement in TNSS during birch pollen season (e.g., over at least 28, 57, 85, or 113 days during birch pollen season or during an entire birch pollen season) relative to a baseline or control value (e.g., a baseline TNSS score for a subject prior to the start of treatment). In some embodiments, treatment results in a decrease in TNSS of at least 10%, 15%, 20%, 25%, 30%, 35%, 40%, 45%, 50% or more relative to a baseline or control value.

In some embodiments, treatment results in an improvement in TNSS after NAC (e.g., with birch pollen extract), wherein the improvement comprises a reduction in score for one or more of (i) congestion, (ii) itching, (iii) rhinorrhea, or (iv) sneezing, and/or total TNSS score, relative to a baseline score for the subject. In some embodiments, treatment results in a decrease in TNSS of at least 10%, 15%, 20%, 25%, 30%, 35%, 40%, 45%, 50% or more relative to a baseline score for the subject. In some embodiments, treatment results in a decrease in TNSS score of 1, 2, 3, 4, 5 or more points relative to a baseline score for the subject.

In some embodiments, treatment according to the methods disclosed herein (e.g., administering an anti-Bet v 1 antibody or anti-Bet v 1 antibody cocktail as disclosed herein) reduces a subject's TNSS AUC (0-1 hr) by at least about 15%, 20%, 25%, 30%, 35% or more relative to a baseline TNSS AUC (0-1 hr) for the subject (e.g., a baseline TNSS AUC (0-1 hr) for the subject prior to the onset of treatment). In some embodiments, the TNSS AUC (0-1 hr) is measured after NAC. In some embodiments, treatment reduces a subject's peak TNSS by at least about 15%, 20%, 25%, 30%, 35% or more relative to a baseline peak TNSS for the subject (e.g., a baseline peak TNSS for the subject prior to the onset of treatment). In some embodiments, the peak TNSS is measured after NAC. In some embodiments, the baseline peak TNSS is evaluated by determining the dose of allergen (e.g., Bet v 1 allergen or birch extract) that achieves TNSS of 7 in the subject prior to the onset of treatment, and the peak TNSS after treatment is evaluated by administering to the subject the same dose of allergen that achieved TNSS 7 at baseline.

In some embodiments, treatment according to the methods disclosed herein improves one or more symptoms of allergic conjunctivitis in a subject. As used herein, "improving allergic conjunctivitis symptoms" includes reducing the severity or duration of or eliminating one or more symptoms of allergic conjunctivitis in the subject, such as but not limited to itchy, red, tearing, or puffy eyes. In some embodiments, a reduction in allergic conjunctivitis symptoms is measured by Total Ocular Symptom Score (TOSS). TOSS is a patient-reported composite symptom assessment of ocular symptoms.

In some embodiments, TOSS ranges from 0-6 and is based on two symptoms: itching/redness/gritty feeling and tearing/watering. Each of the 2 symptoms is graded by the patient as 0 (absent), 1 (mild), 2 (moderate), or 3 (severe). In other embodiments, TOSS ranges from 0-12 and is based on four items: itching/burning, redness, watering and tearing, and puffiness and swelling; patient-assessed symptom scores are assigned for each category for a given time point, using a four point scale (0-3), where 0 indicates no symptoms, a score of 1 for mild symptoms that are easily tolerated, 2 for awareness of symptoms which are bothersome but tolerable and 3 is reserved for severe symptoms that are hard to tolerate and interfere with daily activity.

In some embodiments, a TOSS score is measured after NAC with an allergen. In some embodiments, a baseline TOSS score is measured for a subject (e.g., during a screening visit prior to the start of treatment). In some embodiments, treatment results in an improvement in TOSS after NAC (e.g., with birch pollen extract), wherein the improvement comprises a reduction in score for one or more of (i) itching/burning, (ii) redness, (iii) watering and tearing, or (iv) puffiness and swelling, and/or total TOSS score, relative to a baseline score for the subject.

In some embodiments, treatment results in a decrease in TOSS of at least 10%, 15%, 20%, 25%, 30%, 35%, 40%, 45%, 50% or more relative to a baseline score for the subject. In some embodiments, treatment results in a decrease in TOSS score of 1, 2, 3, 4, 5 or more points relative to a baseline score for the subject. In some embodiments, treatment reduces a subject's TOSS AUC (0-1 hr) by at least about 15%, 20%, 25%, 30%, 35% or more relative to a baseline TOSS AUC (0-1 hr) for subject (e.g., a baseline TOSS AUC (0-1 hr) for the subject prior to the onset of treatment). In some embodiments, the TOSS AUC (0-1 hr) is measured after NAC.

In some embodiments, treatment according to the methods disclosed herein results in an improvement (i.e., reduction) in a subject's Total Symptom Score (TSS). TSS is calculated by adding together a subject's TNSS (ranging from 0-12) and TOSS (ranging from 0-6), for a combined TNSS of 0 to 18. In some embodiments, a baseline TSS score is measured for a subject (e.g., during a screening visit prior to the start of treatment). In some embodiments, treatment results in an improvement in TSS during birch pollen season (e.g., over at least 28, 57, 85, or 113 days during birch pollen season or during an entire birch pollen season) relative to a baseline or control value (e.g., a baseline TSS score for a subject prior to the start of treatment). In some embodiments, treatment results in a decrease in TSS of at least 10%, 15%, 20%, 25%, 30%, 35%, 40%, 45%, 50% or more relative to a baseline or control value. In some embodiments, treatment results in a decrease in TSS score of 1, 2, 3, 4, 5 or more points relative to a baseline score for the subject.

In some embodiments, treatment according to the methods disclosed herein results in an improvement (i.e., reduction) in a subject's Daily Medication Score (DMS). For calculating a DMS, a subject records their daily rescue medication use, including which medication(s) and the amount of these pre-specified medication(s). This information is used to calculate the DMS as follows: desloratadine 5 mg 6 points/dose; maximum daily score 6 points, olopatadine 1 mg/mL each drop 1.5 points/drop; maximum daily score 6 points, mometasone furoate 50 µg/dose 2.0 points/ spray; maximum daily score 8 points). The maximum DMS score is 20. See, Calderon et al., *Clin Exp Allergy* 2014; 44(10):1228-39. In some embodiments, a baseline DMS score is measured for a subject (e.g., during a screening visit prior to the start of treatment). In some embodiments, treatment results in an improvement in DMS during birch pollen season (e.g., over at least 28, 57, 85, or 113 days during birch pollen season or during an entire birch pollen season) relative to a baseline or control value (e.g., a baseline TSS score for a subject prior to the start of treatment). In some embodiments, treatment results in a decrease in DMS of at least 10%, 15%, 20%, 25%, 30%, 35%, 40%, 45%, 50% or more relative to a baseline or control value. In some embodiments, treatment results in a decrease in DMS score of 1, 2, 3, 4, 5 or more points relative to a baseline score for the subject.

In some embodiments, treatment according to the methods disclosed herein results in an improvement (i.e., reduction) in a subject's combined symptom and medication score (CSMS). CSMS is calculated by adding together a subject's DMS (ranging from 0-20) and TSS (ranging from 0-18), for a combined CSMS of 0 to 38. In some embodiments, a baseline CSMS score is measured for a subject (e.g., during a screening visit prior to the start of treatment). In some embodiments, treatment results in an improvement in CSMS during birch pollen season (e.g., over at least 28, 57, 85, or 113 days during birch pollen season or during an entire birch pollen season) relative to a baseline or control value (e.g., a baseline CSMS score for a subject prior to the start of treatment). In some embodiments, treatment results in a decrease in CSMS of at least 10%, 15%, 20%, 25%, 30%, 35%, 40%, 45%, 50% or more relative to a baseline or control value. In some embodiments, treatment results in a decrease in CSMS score of 1, 2, 3, 4, 5, 6, 7, 8, 9, 10 or more points relative to a baseline score for the subject.

In some embodiments, treatment according to the methods disclosed herein improves a subject's peak nasal inspiratory flow (PNIF) as compared to a baseline value (e.g., a baseline PNIF for the subject prior to the onset of treatment). In some embodiments, the PNIF is measured after NAC. In some embodiments, treatment increases a subject's PNIF by at least about 15%, 20%, 25%, 30%, 35%, 40%, 45%, 50%, or more relative to a baseline PNIF for the subject (e.g., a baseline PNIF for the subject prior to the onset of treatment).

In some embodiments, treatment according to the methods disclosed herein reduces a subject's allergen sensitization (e.g., sensitization to birch allergen) as compared to a baseline value (e.g., the subject's level of sensitization prior to the onset of treatment). In some embodiments, treatment reduces a subject's allergen sensitization (e.g., birch sensitization) by at least about 20%, 25%, 30%, 35%, 40%, 45%, 50%, 55%, 60%, 65%, 70%, 75% or more as compared to the subject's level of sensitization prior to the onset of treatment. In some embodiments, level of sensitization is measured using a skin prick test with the allergen (e.g., birch allergen extract). In some embodiments, level of sensitization is assessed by measuring serum antibodies (e.g., allergen specific IgE levels, such as Bet v 1 or birch pollen IgE).

In some embodiments, treatment according to the methods disclosed herein results in an increase in the subject's number of well days during birch pollen season. As used herein, a "well day" is defined as a day when the subject's TSS is without the use of anti-allergy rescue medication.

In some embodiments, treatment according to the methods disclosed herein improves one or more symptoms of oral allergy syndrome. Oral allergy syndrome symptoms typically include itching of lips, mouth, and throat, and can also include lip and tongue swelling and angioedema. In some embodiments, methods of treating birch pollen-related oral allergy syndrome by administering an anti-Bet v 1 antibody or anti-Bet v 1 antibody cocktail as disclosed herein are provided.

In some embodiments, treatment according to the methods disclosed herein (e.g., administering an anti-Bet v 1 antibody or anti-Bet v 1 antibody cocktail as disclosed herein) results in one or more improvements as described above for a prolonged period of time, e.g., for at least one month, at least two months, at least three months, at least four months, or longer.

Anti-Bet v 1 Antibodies and Antigen-Binding Fragments Thereof

According to certain embodiments of the present disclosure, an anti-Bet v 1 antibody or antigen-binding fragment thereof comprises a heavy chain variable region (HCVR), light chain variable region (LCVR), and/or complementarity determining regions (CDRs) comprising any of the amino acid sequences of the anti-Bet v 1 antibodies as set forth in WO 2018/222854, incorporated by reference herein.

In some embodiments, an anti-Bet v 1 antibody or antigen-binding fragment thereof comprises the heavy chain complementarity determining regions (HCDRs) of a heavy chain variable region (HCVR) comprising the amino acid sequence of SEQ ID NO:1 and the light chain complementarity determining regions (LCDRs) of a light chain variable region (LCVR) comprising the amino acid sequence of SEQ ID NO:5. In some embodiments, the anti-Bet v 1 antibody or antigen-binding fragment thereof comprises three HCDRs (HCDR1, HCDR2 and HCDR3) and three LCDRs (LCDR1, LCDR2 and LCDR3), wherein the HCDR1 comprises the amino acid sequence of SEQ ID NO:2, the HCDR2 comprises the amino acid sequence of SEQ ID NO:3, the HCDR3 comprises the amino acid sequence of SEQ ID NO:4, the LCDR1 comprises the amino acid sequence of SEQ ID NO:6, the LCDR2 comprises the amino acid sequence of SEQ ID NO:7, and the LCDR3 comprises the amino acid sequence of SEQ ID NO:8. In some embodiments, the anti-Bet v 1 antibody or antigen-binding fragment thereof comprises the HCDR1, HCDR2, HCDR3, LCDR1, LCDR2, and LCDR3 of SEQ ID NOs:2, 3, 4, 6, 7, and 8, respectively, and further comprises an HCVR having at least 85% sequence identity (e.g., at least 90%, 91%, 92%, 93%, 94%, 95%, 96%, 97%, 98%, or 99% sequence identity) to the amino acid sequence of SEQ ID NO:1 and an LCVR having at least 85% sequence identity (e.g., at least 90%, 91%, 92%, 93%, 94%, 95%, 96%, 97%, 98%, or 99% sequence identity) to the amino acid sequence of SEQ ID NO:5. In some embodiments, the anti-Bet v 1 antibody or antigen-binding fragment thereof comprises an HCVR comprising SEQ ID NO:1 and an LCVR comprising SEQ ID NO:5. In some embodiments, the anti-Bet v 1 antibody or antigen-binding fragment thereof comprises a heavy chain comprising the amino acid sequence of SEQ ID NO:9. In some embodiments, the anti-Bet v 1 antibody or antigen-binding fragment thereof comprises a light chain comprising the amino acid sequence of SEQ ID NO:10.

In some embodiments, an anti-Bet v 1 antibody or antigen-binding fragment thereof comprises the HCDRs of a HCVR comprising the amino acid sequence of SEQ ID NO:11 and the LCDRs of a LCVR comprising the amino acid sequence of SEQ ID NO:15. In some embodiments, the anti-Bet v 1 antibody or antigen-binding fragment thereof comprises three HCDRs (HCDR1, HCDR2 and HCDR3) and three LCDRs (LCDR1, LCDR2 and LCDR3), wherein the HCDR1 comprises the amino acid sequence of SEQ ID NO:12, the HCDR2 comprises the amino acid sequence of SEQ ID NO:13, the HCDR3 comprises the amino acid sequence of SEQ ID NO:14, the LCDR1 comprises the amino acid sequence of SEQ ID NO:16, the LCDR2 comprises the amino acid sequence of SEQ ID NO:17, and the LCDR3 comprises the amino acid sequence of SEQ ID NO:18. In some embodiments, the anti-Bet v 1 antibody or antigen-binding fragment thereof comprises the HCDR1, HCDR2, HCDR3, LCDR1, LCDR2, and LCDR3 of SEQ ID NOs:12, 13, 14, 16, 17, and 18, respectively, and further comprises an HCVR having at least 85% sequence identity (e.g., at least 90%, 91%, 92%, 93%, 94%, 95%, 96%, 97%, 98%, or 99% sequence identity) to the amino acid sequence of SEQ ID NO:11 and an LCVR having at least 85% sequence identity (e.g., at least 90%, 91%, 92%, 93%, 94%, 95%, 96%, 97%, 98%, or 99% sequence identity) to the amino acid sequence of SEQ ID NO:15. In some embodiments, the anti-Bet v 1 antibody or antigen-binding fragment thereof comprises an HCVR comprising SEQ ID NO:11 and an LCVR comprising SEQ ID NO:15. In some embodiments, the anti-Bet v 1 antibody or antigen-binding fragment thereof comprises a heavy chain comprising the amino acid sequence of SEQ ID NO:19. In some embodiments, the anti-Bet v 1 antibody or antigen-binding fragment thereof comprises a light chain comprising the amino acid sequence of SEQ ID NO:20.

In some embodiments, an anti-Bet v 1 antibody or antigen-binding fragment thereof comprises the HCDRs of a HCVR comprising the amino acid sequence of SEQ ID NO:21 and the LCDRs of a LCVR comprising the amino acid sequence of SEQ ID NO:25. In some embodiments, the anti-Bet v 1 antibody or antigen-binding fragment thereof comprises three HCDRs (HCDR1, HCDR2 and HCDR3) and three LCDRs (LCDR1, LCDR2 and LCDR3), wherein the HCDR1 comprises the amino acid sequence of SEQ ID NO:22, the HCDR2 comprises the amino acid sequence of SEQ ID NO:23, the HCDR3 comprises the amino acid sequence of SEQ ID NO:24, the LCDR1 comprises the amino acid sequence of SEQ ID NO:26, the LCDR2 comprises the amino acid sequence of SEQ ID NO:27, and the LCDR3 comprises the amino acid sequence of SEQ ID NO:28. In some embodiments, the anti-Bet v 1 antibody or antigen-binding fragment thereof comprises the HCDR1, HCDR2, HCDR3, LCDR1, LCDR2, and LCDR3 of SEQ ID NOs:22, 23, 24, 26, 27, and 28, respectively, and further comprises an HCVR having at least 85% sequence identity (e.g., at least 90%, 91%, 92%, 93%, 94%, 95%, 96%, 97%, 98%, or 99% sequence identity) to the amino acid sequence of SEQ ID NO:21 and an LCVR having at least 85% sequence identity (e.g., at least 90%, 91%, 92%, 93%, 94%, 95%, 96%, 97%, 98%, or 99% sequence identity) to the amino acid sequence of SEQ ID NO:25. In some embodiments, the anti-Bet v 1 antibody or antigen-binding fragment thereof comprises an HCVR comprising SEQ ID NO:21 and an LCVR comprising SEQ ID NO:25. In some embodiments, the anti-Bet v 1 antibody or antigen-binding fragment thereof comprises a heavy chain comprising the amino acid sequence of SEQ ID NO:29. In some embodiments, the anti-Bet v 1 antibody or antigen-binding fragment thereof comprises a light chain comprising the amino acid sequence of SEQ ID NO:30.

In some embodiments, the anti-Bet v 1 antibody is a bioequivalent of an antibody disclosed herein (e.g., a bioequivalent of REGN5713, REGN5714, or REGN5715). The term "bioequivalent," as used herein, refers to an anti-Bet v 1 antibody that is a pharmaceutical equivalent or pharmaceutical alternative whose rate and/or extent of absorption does not show a significant difference with that of the reference antibody (e.g., REGN5713, REGN5714, or REGN5715) when administered at the same molar dose under similar experimental conditions, either single dose or multiple dose. In some embodiments, the term refers to anti-Bet v 1 antibodies which do not have clinically meaningful differences with an anti-Bet v 1 antibody of the present disclosure (e.g., REGN5713, REGN5714, or REGN5715) in their safety, purity and/or potency.

In some embodiments, the anti-Bet v 1 antibody is an IgG1 or an IgG4 antibody. In some embodiments, the anti-Bet v 1 antibody comprises a heavy chain constant region of a human IgG1 or IgG4 isotype in which the constant region comprises one or more amino acid modifications (e.g., substitutions or deletions), e.g., an amino acid modification in the hinge, $C_H2$, or $C_H3$ region.

In some embodiments, an anti-Bet v 1 antibody used in the methods of the present disclosure can have pH-dependent binding characteristics. For example, an anti-Bet v 1 antibody for use in the methods of the present disclosure may exhibit reduced binding to Bet v 1 at acidic pH as compared to neutral pH. Alternatively, an anti-Bet v 1 antibody of the disclosure may exhibit enhanced binding to its antigen at acidic pH as compared to neutral pH. The expression "acidic pH" includes pH values less than about 6.2, e.g., about 6.0, 5.95, 5.9, 5.85, 5.8, 5.75, 5.7, 5.65, 5.6, 5.55, 5.5, 5.45, 5.4, 5.35, 5.3, 5.25, 5.2, 5.15, 5.1, 5.05, 5.0, or less. As used herein, the expression "neutral pH" means a pH of about 7.0 to about 7.4. The expression "neutral pH" includes pH values of about 7.0, 7.05, 7.1, 7.15, 7.2, 7.25, 7.3, 7.35, and 7.4.

Antibodies with pH-dependent binding characteristics may be obtained, e.g., by screening a population of antibodies for reduced (or enhanced) binding to a particular antigen at acidic pH as compared to neutral pH. Additionally, modifications of the antigen-binding domain at the amino acid level may yield antibodies with pH-dependent characteristics. For example, by substituting one or more amino acids of an antigen-binding domain (e.g., within a CDR) with a histidine residue, an antibody with reduced antigen-binding at acidic pH relative to neutral pH may be obtained.

In some embodiments, the therapeutic methods disclosed herein comprise the use of two or more anti-Bet v 1 antibodies as disclosed herein, e.g., a pharmaceutical composition comprising two or three anti-Bet v 1 antibodies as disclosed herein.

In some embodiments, the combination or the pharmaceutical composition comprises:

(a) a first anti-Bet v 1 antibody or antigen-binding fragment thereof, wherein the first anti-Bet v 1 antibody comprises a heavy chain complementarity determining region (HCDR) 1 comprising the amino acid sequence of SEQ ID NO:2, an HCDR2 comprising the amino acid sequence of SEQ ID NO:3, an HCDR3 comprising the amino acid sequence of SEQ ID NO:4, a light chain complementarity determining region (LCDR) 1 comprising the amino acid sequence of SEQ ID NO:6, an LCDR2 comprising the amino acid sequence of SEQ ID NO:7, and an LCDR3 comprising the amino acid sequence of SEQ ID NO:8; and/or (b) a second anti-Bet v 1 antibody or antigen-binding fragment thereof, wherein the second anti-Bet v 1 antibody comprises an HCDR1 comprising the amino acid sequence of SEQ ID NO:12, an HCDR2 comprising the amino acid sequence of SEQ ID NO:13, an HCDR3 comprising the amino acid sequence of SEQ ID NO:14, an LCDR1 comprising the amino acid sequence of SEQ ID NO:16, an LCDR2 comprising the amino acid sequence of SEQ ID NO:17, and an LCDR3 comprising the amino acid sequence of SEQ ID NO:18; and/or (c) a third anti-Bet v 1 antibody or antigen-binding fragment thereof, wherein the third anti-Bet v 1 antibody comprises an HCDR1 comprising the amino acid sequence of SEQ ID NO:22, an HCDR2 comprising the amino acid sequence of SEQ ID NO:23, an HCDR3 comprising the amino acid sequence of SEQ ID NO:24, an LCDR1 comprising the amino acid sequence of SEQ ID NO:26, an LCDR2 comprising the amino acid sequence of SEQ ID NO:27, and an LCDR3 comprising the amino acid sequence of SEQ ID NO:28.

In some embodiments, the pharmaceutical composition comprises (a) and (b). In some embodiments, the pharmaceutical composition comprises (a) and (c). In some embodiments, the pharmaceutical composition comprises (b) and (c). In some embodiments, the pharmaceutical composition comprises (a), (b), and (c).

Preparation of Human Antibodies

Methods for generating human antibodies in transgenic mice are known in the art. Any such known methods can be used in the context of the present disclosure to make human antibodies that specifically bind to the Bet v 1 protein.

Using VELOCIMMUNE™ technology (see, for example, U.S. Pat. No. 6,596,541, Regeneron Pharmaceuticals) or any other known method for generating monoclonal antibodies, high affinity chimeric antibodies to IL-4R are initially isolated having a human variable region and a mouse constant region. The VELOCIMMUNE® technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody.

Generally, a VELOCIMMUNE® mouse is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies or the variable domains of the light and heavy chains may be isolated directly from antigen-specific lymphocytes.

Initially, high affinity chimeric antibodies are isolated having a human variable region and a mouse constant region. The antibodies are characterized and selected for desirable characteristics, including affinity, selectivity, epitope, etc., using standard procedures known to those skilled in the art. The mouse constant regions are replaced with a desired human constant region to generate the fully human antibody of the disclosure, for example wild-type or modified IgG1 or IgG4. While the constant region selected may vary according to specific use, high affinity antigen-binding and target specificity characteristics reside in the variable region.

In general, the antibodies that can be used in the methods of the present disclosure possess high affinities, as described above, when measured by binding to antigen either immobilized on solid phase or in solution phase. The mouse constant regions are replaced with desired human constant regions to generate the fully human antibodies of the disclosure. While the constant region selected may vary according to specific use, high affinity antigen-binding and target specificity characteristics reside in the variable region.

Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

Pharmaceutical Compositions

In one aspect, the present disclosure provides methods that comprise administering one or more anti-Bet v 1 antibodies to a subject, wherein the one or more anti-Bet v 1 antibodies are contained within a pharmaceutical composition that comprises one or more pharmaceutically acceptable vehicle, carriers, and/or excipients. In some embodiments, the antibody or antibodies are for use in treating birch allergy or for treating a condition associated with birch allergy (e.g., allergic rhinitis or oral allergy syndrome).

In some embodiments, the pharmaceutical composition comprises one anti-Bet v 1 antibody or antigen-binding fragment thereof (e.g., an antibody comprising the HCDR1, HCDR2, HCDR3, LCDR1, LCDR2, and LCDR3 of SEQ ID NOs: 2, 3, 4, 6, 7, and 8, respectively; or an antibody comprising the HCDR1, HCDR2, HCDR3, LCDR1, LCDR2, and LCDR3 of SEQ ID NOs: 12, 13, 14, 16, 17, and 18, respectively; or an antibody comprising the HCDR1, HCDR2, HCDR3, LCDR1, LCDR2, and LCDR3 of SEQ ID NOs: 22, 23, 24, 26, 27, and 28, respectively).

In some embodiments, the pharmaceutical composition comprises two anti-Bet v 1 antibodies or antigen-binding fragments thereof. For example, in some embodiments, the pharmaceutical composition comprises an antibody comprising the HCDR1, HCDR2, HCDR3, LCDR1, LCDR2, and LCDR3 of SEQ ID NOs: 2, 3, 4, 6, 7, and 8, respectively, and an antibody comprising the HCDR1, HCDR2, HCDR3, LCDR1, LCDR2, and LCDR3 of SEQ ID NOs: 12, 13, 14, 16, 17, and 18, respectively. In some embodiments, the pharmaceutical composition comprises an antibody comprising the HCDR1, HCDR2, HCDR3, LCDR1, LCDR2, and LCDR3 of SEQ ID NOs: 2, 3, 4, 6, 7, and 8, respectively, and an antibody comprising the HCDR1, HCDR2, HCDR3, LCDR1, LCDR2, and LCDR3 of SEQ ID NOs: 22, 23, 24, 26, 27, and 28, respectively. In some embodiments, the pharmaceutical composition comprises an antibody comprising the HCDR1, HCDR2, HCDR3, LCDR1, LCDR2, and LCDR3 of SEQ ID NOs: 12, 13, 14, 16, 17, and 18, respectively, and an antibody comprising the HCDR1, HCDR2, HCDR3, LCDR1, LCDR2, and LCDR3 of SEQ ID NOs: 22, 23, 24, 26, 27, and 28, respectively.

In some embodiments, the pharmaceutical composition comprises three anti-Bet v 1 antibodies or antigen-binding fragments thereof. For example, in some embodiments, the pharmaceutical composition comprise san antibody comprising the HCDR1, HCDR2, HCDR3, LCDR1, LCDR2, and LCDR3 of SEQ ID NOs: 2, 3, 4, 6, 7, and 8, respectively, an antibody comprising the HCDR1, HCDR2, HCDR3, LCDR1, LCDR2, and LCDR3 of SEQ ID NOs: 12, 13, 14, 16, 17, and 18, respectively, and an antibody comprising the HCDR1, HCDR2, HCDR3, LCDR1, LCDR2, and LCDR3 of SEQ ID NOs: 22, 23, 24, 26, 27, and 28, respectively.

Various pharmaceutically acceptable carriers and excipients are well-known in the art. See, e.g., Remington's Pharmaceutical Sciences, Mack Publishing Company, Easton, Pa. In some embodiments, the carrier is suitable for intravenous, intramuscular, oral, intraperitoneal, intrathecal, transdermal, topical, or subcutaneous administration.

In some embodiments, the pharmaceutical composition comprises an injectable preparation, such as a dosage form for intravenous, subcutaneous, intracutaneous and intramuscular injections, drip infusions, etc. These injectable preparations may be prepared by known methods. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared can be filled in an appropriate ampoule.

The dose of the one or more antibodies that are administered to a patient according to the methods of the present disclosure may vary depending upon the age and the size of the patient, symptoms, conditions, route of administration, and the like. The dose is typically calculated according to body weight or body surface area. Depending on the severity of the condition, the frequency and the duration of the treatment can be adjusted. Effective dosages and schedules for administering pharmaceutical compositions comprising anti-Bet v 1 antibodies may be determined empirically; for example, patient progress can be monitored by periodic assessment, and the dose adjusted accordingly. Moreover, interspecies scaling of dosages can be performed using well-known methods in the art (e.g., Mordenti et al., 1991, *Pharmaceut. Res.* 8:1351). Specific exemplary doses of anti-Bet v 1 antibodies, and administration regimens involving the same, that can be used in the context of the present disclosure are disclosed elsewhere herein.

Various delivery systems are known and can be used to administer the pharmaceutical composition, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of administration include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. In some embodiments, a pharmaceutical composition as disclosed herein is administered intravenously. In some embodiments, a pharmaceutical composition as disclosed herein is administered subcutaneously.

In some embodiments, a pharmaceutical composition of the present disclosure is contained within a container. Thus, in another aspect, containers comprising a pharmaceutical composition as disclosed herein are provided. For example, in some embodiments, a pharmaceutical composition is contained within a container selected from the group consisting of a glass vial, a syringe, a pen delivery device, and an autoinjector.

In some embodiments, a pharmaceutical composition of the present disclosure is delivered, e.g., subcutaneously or intravenously, with a standard needle and syringe. In some embodiments, the syringe is a pre-filled syringe. In some embodiments, a pen delivery device or autoinjector is used to deliver a pharmaceutical composition of the present disclosure (e.g., for subcutaneous delivery). A pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Examples of suitable pen and autoinjector delivery devices include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, IN), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, NJ), OPTIPEN™, OPTIPEN PRO™ OPTIPEN STARLET™, and OPTICLIK™ (Sanofi-Aventis, Frankfurt, Germany). Examples of disposable pen delivery devices having applications in subcutaneous delivery of a pharmaceutical composition of the present disclosure include, but are not limited to the SOLOSTAR™ pen (Sanofi-Aventis), the FLEXPEN™ (Novo Nordisk), and the KWIKPEN™ (Eli Lilly), the SURECLICK™ Autoinjector (Amgen, Thousand Oaks, CA), the PENLET™ (Haselmeier, Stuttgart, Germany), the EPIPEN (Dey, L. P.), and the HUM IRA™ Pen (Abbott Labs, Abbott Park IL).

In some embodiments, the pharmaceutical composition is delivered using a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Florida In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

In some embodiments, pharmaceutical compositions for use as described herein are prepared into dosage forms in a unit dose suited to fit a dose of the active ingredients. Such dosage forms in a unit dose include, for example, tablets, pills, capsules, injections (ampoules), suppositories, etc.

Dosage and Administration Regimens

Typically, an amount of an anti-Bet v 1 antibody that is administered to a subject according to the methods disclosed herein is a therapeutically effective amount. As used herein, the phrase "therapeutically effective amount" means an amount of an anti-Bet v 1 antibody (or combination of anti-Bet v 1 antibodies) that results in one or more of: (a) a reduction in the severity or duration of one or more symptoms of birch allergy; (b) prevention or alleviation of an allergic reaction to a birch allergen (e.g., birch pollen extract or a Bet v 1 protein); (c) reduction in provoked allergic rhinitis symptoms after nasal allergen challenge; (d) reduction in the level of one or more markers of Type 2 immune activity (e.g., serum TARC or total IgE); and (e) a reduction in the use or need for conventional allergy therapy (e.g., reduced or eliminated use of antihistamines, decongestants, nasal or inhaled steroids, anti-IgE treatment, epinephrine, etc.).

In the case of an anti-Bet v 1 antibody (e.g., an antibody comprising the CDRs and/or HCVR and LCVR sequences of REGN5713, REGN5714, or REGN5715 as disclosed herein), a therapeutically effective amount can be from about 0.05 mg to about 600 mg, about 10 mg to about 600 mg, or about 10 mg to about 300 mg, about 25 mg to about 500 mg, or about 50 mg to about 300 mg, e.g., about 0.05 mg, about 0.1 mg, about 1.0 mg, about 1.5 mg, about 2.0 mg, about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, or about 600 mg, of the anti-Bet v 1 antibody. In certain embodiments, about 50 mg, 100 mg, 150 mg, 200 mg, 250 mg, or 300 mg of an anti-Bet v 1 antibody is administered to a subject.

In some embodiments, a therapeutically effective amount of each of two or more anti-Bet v 1 antibodies as disclosed herein is administered to a subject. For example, in some embodiments, a therapeutically effective amount of each of REGN5713 and REGN5714, or each of REGN5713 and REGN5715, or each of REGN5714 and REGN5715, is administered to the subject. In some embodiments, a therapeutically effective amount of each of REGN5713, REGN5714, and REGN5715 is administered to the subject. In some embodiments, each of the anti-Bet v 1 antibodies is administered in an amount from about 0.05 mg to about 600 mg, about 10 mg to about 600 mg, or about 10 mg to about 300 mg, about 25 mg to about 500 mg, or about 50 mg to about 300 mg, e.g., about 0.05 mg, about 0.1 mg, about 1.0 mg, about 1.5 mg, about 2.0 mg, about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, or about 600 mg. In some embodiments, each of the two or more anti-Bet v 1 antibodies (e.g., two or more of REGN5713, REGN5714, and REGN5715) is administered in an amount of about 50 mg, 100 mg, 150 mg, 200 mg, 250 mg, or 300 mg. In some embodiments, the two or more anti-Bet v 1 antibodies are administered in the same amount. In some embodiments, the two or more anti-Bet v 1 antibodies are administered in different amounts. In some embodiments wherein three anti-Bet v 1 antibodies are administered, at least one antibody is administered in a different amount than the other antibodies. In some embodiments wherein three anti-Bet v 1 antibodies are administered, all three antibodies are administered in different amounts. In some embodiments wherein three anti-Bet v 1 antibodies are administered, all three antibodies are administered in the same amount.

In some embodiments, the anti-Bet v 1 antibody or antibodies (e.g., an antibody comprising the CDRs and/or HCVR and LCVR sequences of REGN5713, REGN5714, and/or REGN5715 as disclosed herein) are administered at a total dose of about 50 mg to about 1500 mg, e.g., about 100 mg to about 1500 mg, about 100 mg to about 1000 mg, or about 300 mg to about 1000 mg. In some embodiments, the anti-Bet v 1 antibody or antibodies are administered at a total dose of about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1025 mg, about 1050 mg, about 1075 mg, about 1100 mg, about 1125 mg, about 1150 mg, about 1175 mg, about 1200 mg, about 1225 mg, about 1250 mg, about 1275 mg, about 1300 mg, about 1325 mg, about 1350 mg, about 1375 mg, about 1400 mg, about 1450 mg, about 1475 mg, or about 1500 mg.

The amount of an anti-Bet v 1 antibody contained within the individual doses may be expressed in terms of milligrams of active agent (e.g., antibody) per kilogram of patient body weight (i.e., mg/kg). For example, the anti-Bet v 1 antibody may be administered to a patient at a dose of about 0.0001 to about 10 mg/kg of patient body weight, e.g., from about 1 mg/kg to about 10 mg/kg, or about 1 mg/kg, 2 mg/kg, 3 mg/kg, 4 mg/kg, 5 mg/kg, 6 mg/kg, 7 mg/kg, 8 mg/kg, 9 mg/kg, or 10 mg/kg.

In some embodiments, the anti-Bet v 1 antibody or antibodies, or pharmaceutical composition comprising one or more anti-Bet v 1 antibodies, is administered to a subject at a dosing frequency of about four times a week, twice a week, once a week, once every two weeks, once every three weeks, once every four weeks, once every five weeks, once every six weeks, once every eight weeks, once every twelve weeks, or less frequently so long as a therapeutic response is achieved. In some embodiments, the anti-Bet v 1 antibody or antibodies are administered once every three months, once every four months, once every five months, once every six months, once every seven months, once every eight months, once every nine months, once every ten months, once every eleven months, or once every twelve months. In some embodiments, the anti-Bet v 1 antibody or antibodies are administered once a year or twice a year. In some embodiments, the anti-Bet v 1 antibody or antibodies are administered once a year or twice a year, prior to the onset of allergy season (e.g., prior to birch pollen season).

In certain embodiments involving the administration of a pharmaceutical composition comprising an anti-Bet v 1 antibody at a dosing frequency described herein, each dose is administered at an amount of about 50 mg to about 600 mg, e.g., about 50 mg, 100 mg, 150 mg, 200 mg, 250 mg, or 300 mg, or in embodiments wherein two or more anti-Bet v 1 antibodies are administered, for each dose that is administered, each of the anti-Bet v 1 antibodies are administered in amount of about 50 mg to about 600 mg, e.g., about 50 mg, 100 mg, 150 mg, 200 mg, 250 mg, or 300 mg. In certain embodiments where two anti-Bet v 1 antibodies are administered, for each dose that is administered, the anti-Bet v 1 antibodies are administered in a 1:1 ratio. In certain embodiments where three anti-Bet v 1 antibodies are administered, for each dose that is administered, the anti-Bet v 1 antibodies are administered in a 1:1:1 ratio.

In some embodiments, multiple doses of an anti-Bet v 1 antibody or cocktail of anti-Bet v 1 antibodies are administered to a subject over a defined time course. In some embodiments, the methods of the present disclosure comprise sequentially administering to a subject multiple doses of an anti-Bet v 1 antibody or antibodies. As used herein, "sequentially administering" means that each dose of the anti-Bet v 1 antibody or antibodies is administered to the subject at a different point in time, e.g., on different days separated by a predetermined interval (e.g., hours, days, weeks or months). In some embodiments, the methods of the disclosure comprise sequentially administering to the patient a single initial dose of an anti-Bet v 1 antibody or antibodies, followed by one or more secondary doses of the anti-Bet v 1 antibody or antibodies, and optionally followed by one or more tertiary doses of the anti-Bet v 1 antibody or antibodies. The terms "initial dose," "secondary dose(s)," and "tertiary dose(s)" refer to the temporal sequence of administration of the anti-Bet v 1 antibody or antibodies. Thus, the "initial dose" is the dose which is administered at the beginning of the treatment regimen (also referred to as the "loading dose"); the "secondary doses" are the doses which are administered after the initial dose; and the "tertiary doses" are the doses which are administered after the secondary doses.

In some embodiments, the initial, secondary, and tertiary doses all contain the same amount of the anti-Bet v 1 antibody or antibodies, but differ from one another in terms of frequency of administration. In other embodiments, the amount of the anti-Bet v 1 antibody or antibodies contained in the initial, secondary and/or tertiary doses varies from one another (e.g., adjusted up or down as appropriate) during the course of treatment. In certain embodiments, one or more (e.g., 1, 2, 3, 4, or 5) doses are administered at the beginning of the treatment regimen as "loading doses" followed by subsequent doses that are administered on a less frequent basis (e.g., "maintenance doses"). For example, the first amount of the anti-Bet v 1 antibody or cocktail of anti-Bet v 1 antibodies can be 1.5×, 2×, 2.5×, 3×, 3.5×, 4× or 5× or more than the second amount of the anti-Bet v 1 antibody or cocktail of anti-Bet v 1 antibodies.

In some embodiments, each secondary and/or tertiary dose is administered 1 to 30 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, 27, 27½, 28, 28½, 29, 29½, 30 or more) weeks after the immediately preceding dose. The phrase "the immediately preceding dose," as used herein, means, in a sequence of multiple administrations, the dose of an anti-Bet v 1 antibody which is administered to a patient prior to the administration of the very next dose in the sequence with no intervening doses.

The methods of the disclosure may comprise administering to a patient any number of secondary and/or tertiary doses of an anti-Bet v 1 antibody or cocktail of anti-Bet v 1 antibodies. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In some embodiments involving multiple secondary doses, each secondary dose is administered at the same frequency as the other secondary doses. Similarly, in some embodiments involving multiple tertiary doses, each tertiary dose is administered at the same frequency as the other tertiary doses. Alternatively, the frequency at which the secondary and/or tertiary doses are administered to a patient can vary over the course of the treatment regimen. The frequency of administration may also be adjusted during the course of treatment by a physician depending on the needs of the individual patient following clinical examination.

In some embodiments, a pharmaceutical composition comprising each of a first anti-Bet v 1 antibody, a second anti-Bet v 1 antibody, and a third anti-Bet v 1 antibody as disclosed herein is administered to a subject at a dose of about 50 mg per antibody (total dose for the three antibodies of about 150 mg). In some embodiments, the pharmaceutical composition is administered to the subject subcutaneously or intravenously.

In some embodiments, a pharmaceutical composition comprising each of a first anti-Bet v 1 antibody, a second anti-Bet v 1 antibody, and a third anti-Bet v 1 antibody as disclosed herein is administered to a subject at a dose of about 150 mg per antibody (total dose for the three antibodies of about 450 mg). In some embodiments, the pharmaceutical composition is administered to the subject subcutaneously or intravenously.

In some embodiments, a pharmaceutical composition comprising each of a first anti-Bet v 1 antibody, a second anti-Bet v 1 antibody, and a third anti-Bet v 1 antibody as disclosed herein is administered to a subject at a dose of about 300 mg per antibody (total dose for the three antibodies of about 900 mg). In some embodiments, the pharmaceutical composition is administered to the subject subcutaneously or intravenously.

In some embodiments in which more than one anti-Bet v 1 antibody is administered, the anti-Bet v 1 antibodies are in separate pharmaceutical compositions. In some embodiments, the pharmaceutical compositions are administered at the same time (e.g., by combining the compositions in a solution prior to administration). In some embodiments, the pharmaceutical compositions are administered separately (e.g., by sequential administration).

Combination Therapies

In some embodiments, the methods of the present disclosure comprise administering to the subject one or more additional therapeutic agents in combination with an anti-Bet v 1 antibody or cocktail of anti-Bet v 1 antibodies as disclosed herein. As used herein, the expression "in combination with" means that the additional therapeutic agents are administered before, after, or concurrent with the anti-Bet v 1 antibody or antibodies or pharmaceutical composition comprising the anti-Bet v 1 antibody or antibodies. The term "in combination with" also includes sequential or concomitant administration of an anti-Bet v 1 antibody and a second therapeutic agent or therapy.

In some embodiments, the additional therapeutic agent is a steroid, an antihistamine, a decongestant, an anti-IgE agent, or an agent that depletes plasma cells and/or B cells. In some embodiments, the additional therapeutic agent is a steroid (e.g., a corticosteroid, such as an inhaled corticosteroid (ICS)). In some embodiments, the additional therapeutic agent is an antihistamine (e.g., loratadine, fexofenadine, cetirizine, diphenhydramine, promethazine, carbinoxamine, desloratadine, hydroxyzine, levocetirizine, triprolidine, brompheniramine, or chlorpheniramine). In some embodiments, the additional therapeutic agent is a decongestant (e.g., pseudoephedrine or phenylephrine). In some embodiments, the additional therapeutic agent is an anti-IgE agent (e.g., omalizumab). In some embodiments, the additional therapeutic agent is an agent that depletes plasma cells and/or B cells, such as BCMA targeting agents (e.g., anti-BCMA antibodies that are conjugated to a therapeutic agent such as a cytotoxic drug ("BCMA ADC" or "anti-BCMA ADC"), chimeric antigenic receptors (CARs) that bind specifically to BCMA, ("BCMA CAR" or "anti-BCMA CAR") and anti-BCMA/anti-CD3 bispecific antibodies such as those disclosed in WO 2020/018820).

EXAMPLES

The following examples are put forth so as to provide those of ordinary skill in the art with a complete disclosure and description of how to make and use the methods and compositions of the disclosure, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1: Clinical Trial to Investigate the Safety, Tolerability, Pharmacokinetic, and Pharmacodynamic Effects of a Single Dose of REGN5713-5714-5715 in Healthy Adult Subjects Study Design and Objectives This example describes a Phase 1, two-part, randomized, double-blind, placebo-controlled study of the safety, tolerability, pharmacokinetic (PK), and pharmacodynamic (PD) effects of a single dose of REGN5713-5714-5715 in healthy adult subjects (NCT03969849). The safety, tolerability, and PK of single ascending doses of 150 mg subcutaneous (SC), 450 mg SC, 900 mg SC, and 900 mg intravenous (IV) in healthy adult subjects were evaluated in Part A. The safety, tolerability, PK, and PD of one dose of REGN5713-5714-5715 were evaluated in healthy adult subjects with birch pollen allergy in Part B.

REGN5713 is a fully human anti-Bet v 1 antibody comprising the HCVR of SEQ ID NO:1, the HCDR1 of SEQ ID NO:2, the HCDR2 of SEQ ID NO:3, the HCDR3 of SEQ ID NO:4, the LCVR of SEQ ID NO:5, the LCDR1 of SEQ ID NO:6, the LCDR2 of SEQ ID NO:7, and the LCDR3 of SEQ ID NO:8.

REGN5714 is a fully human anti-Bet v 1 antibody comprising the HCVR of SEQ ID NO:11, the HCDR1 of SEQ ID NO:12, the HCDR2 of SEQ ID NO:13, the HCDR3 of SEQ ID NO:14, the LCVR of SEQ ID NO:15, the LCDR1 of SEQ ID NO:16, the LCDR2 of SEQ ID NO:17, and the LCDR3 of SEQ ID NO:18.

REGN5715 is a fully human anti-Bet v 1 antibody comprising the HCVR of SEQ ID NO:21, the HCDR1 of SEQ ID NO:22, the HCDR2 of SEQ ID NO:23, the HCDR3 of SEQ ID NO:24, the LCVR of SEQ ID NO:25, the LCDR1 of SEQ ID NO:26, the LCDR2 of SEQ ID NO:27, and the LCDR3 of SEQ ID NO:28.

The primary objective of the study was to evaluate the safety and tolerability of REGN5713-5714-5715 in healthy adult subjects. The secondary objectives of the study were: to characterize the concentration time profile of single doses of REGN5713-5714-5715 in healthy adults (Parts A and B); to assess the immunogenicity of single dose of REGN5713-5714-5715 (Parts A and B); to assess the inhibition of allergic symptoms as measured by total nasal symptom score (TNSS) provoked by a birch allergen nasal allergen challenge (NAC) in birch-sensitized allergic subjects after a single SC dose of REGN5713-5714-5715 (Part B); and to assess the skin test reactivity provoked by a skin prick test (SPT) with serial birch allergen titration after a single 900 mg SC dose of REGN5713-5714-5715 (Part B). For Part B, additional exploratory objectives were: to assess the inhibition of allergic symptoms as measured by TOSS provoked by a birch allergen NAC in birch-sensitized allergic subjects after a single SC dose of REGN5713-5714-5715; to assess the inhibition of allergic responses as measured by PNIF in birch-sensitized AR subjects challenged intranasally with birch pollen extract (NAC) after a single SC dose of REGN5713-5714-5715; to assess the inhibition of allergic responses as measured by RNA sequencing of nasal mucosal tissue, and chemokine/cytokines in the nasal fluid after NAC in birch-sensitized AR subjects challenged intranasally with birch pollen extract (NAC) after a single SC dose of REGN5713-5714-5715; and to assess the relationship between clinical response to REGN5713-5714-5715 and the ability of REGN5713-5714-5715 and its components to interfere with endogenous serum IgE binding to Bet V 1 at baseline before drug exposure.

In Part A, after obtaining informed consent subjects are assessed for eligibility. Eligible subjects participated in a pre-baseline visit during which they were admitted. Dosing of study drug occurred on the next day, study day 1 (randomization). Subjects were monitored in the clinic for at least 48 hours after an SC dose or at least 24 hours after an IV dose. Following safety assessments, subjects were discharged on day 3 after SC dosing or on day 2 after IV dosing, respectively. Subjects returned to the clinic for safety assessments at days 8, 15, 22, 29, 43, 57, 85, 99, and 113 (for the SC dosing cohorts) or days 4, 8, 15, 22, 29, 43, 57, 85, 99, and 113 (for the IV dosing cohort).

Part B was a randomized, placebo-controlled and double-blind, single-dose nasal allergen challenge (NAC) study to assess safety, tolerability, and drug concentrations over time, as well as the PD effects of 900 mg SC REGN5713-5714-5715 in healthy adult subjects with birch pollen allergy. Part B enrollment occurred outside of birch allergy season in a birch-endemic geographical area. After obtaining informed consent, subjects were assessed for eligibility during a 3-part screening period of up to 12 weeks. During screening visit 1, subjects with a history of AR to birch pollen underwent a medical history, physical examination, SPT for birch, and blood draw for birch pollen and Bet v 1-specific IgE. If the subject met criteria with a positive SPT for birch, and for birch pollen and Bet v 1-specific IgE, as per inclusion/exclusion criteria, they were invited for screening visit 2. At screening visit 2, they underwent a serum pregnancy test if applicable, spirometry, ECG, serologic testing for chronic viral infections (human immunodeficiency virus infection [HIV] and hepatitis B and C), hematology, chemistry, urinalysis, and will be evaluated for the remaining study eligibility criteria. Screening visits 1 and 2 could be combined into one visit if the subject had a historical, positive birch SPT or birch IgE that was completed in the last 12 months. At screening visit 3/entry visit, subjects were observed for at least 10 minutes and a resting/baseline TNSS had to be achieved, signifying that the subject did not have active nasal symptoms at rest (due to viral infection, sinusitis, allergies, etc.), prior to NAC. Before initiating the NAC, the SPT with serial allergen titration was performed to evaluate early phase reaction (EPR). Upon completion of the evaluation of the EPR, the NAC proceeded as follows:

- NAC was performed using increasing doses of birch extract every 10 minutes up to 1 hour (up-titration phase), or until a TNSS was reached.
- The peak TNSS was recorded.
- The birch extract concentration that was used to attain TNSS was recorded.
- Subjects were observed for the subsequent hour and the TNSS was recorded at approximately 5 minutes, 15 minutes, 30 minutes, 45 minutes, 1 hour, and then hourly up to 6 hours post-peak TNSS.
- In addition to TNSS, TOSS, PNIF (measured in nasal patency, L/min) and total sneezes were measured during the NAC procedure and the 6-hour observation period.

Birch-allergic subjects were eligible for enrollment based on having a TNSS prior to the screening NAC (visit 3), peak TNSS within the first hour during the up-titration phase. Additionally, for eligibility, between the first non-zero dose of and approximately 10 minutes after the highest/peak dose, subjects must have experienced either a >20% drop in PNIF or ≥3 sneezes.

Dosing of study drug occurred on study day 1. Subjects were monitored in clinic for at least 8 hours after the SC dose. Following safety assessments, subjects were discharged at least 8 hours after the SC dosing. Subjects returned to the clinic for safety assessments at days 4, 8, 29, 57, 85, 99, and 113. The end of study visit occurred approximately 16 weeks following study drug administration. Subjects were in the study for approximately 28 weeks, including the screening period.

This study was conducted in accordance with the provisions of the Declaration of Helsinki, the International Conference on Harmonization Good Clinical Practices guideline, and applicable regulatory requirements. The protocol was reviewed and approved by institutional review boards/ethics committees at all sites. Written informed consent was obtained from all adult patients.

Patient Population

This study enrolled adult healthy males and females 18 to 60 years of age (inclusive) at screening visit.

Inclusion Criteria: A patient was required to meet the following criteria to be eligible for inclusion in the study: (1) male or female 18 to 60 years of age (inclusive) at screening visit; (2) Body mass index (BMI) between 18 and 31 kg/m$^2$ (inclusive) at screening visit; (3) subject is judged by the investigator to be in good health based on medical history, physical examination, vital sign measurements, and ECG performed prior to study drug dosing; (4) subject is in good health based on laboratory safety testing obtained at the screening visits prior to study drug dosing; (5) willing and able to comply with clinic visits and study-related procedures; (6) provide informed consent signed by study subject or legally acceptable representative. Part B additional inclusion criteria: (7) able to understand and complete study-related questionnaires; (8) has a medical history of birch tree pollen-triggered AR symptoms with or without conjunctivitis (for at least 2 seasons) based on subject's recall; (9) has positive SPT with birch tree pollen extract (mean wheal diameter ≥5 mm greater than a negative control) in screening period; (10) has positive allergen-specific IgE (sIgE) tests for birch tree pollen and Bet v 1 (≥0.35 kUa/L) in screening period; (11) has positive NAC with birch extract with peak TNSS ≥7 out of 12 at screening visit; and (12) experiences a >20% drop in PNIF and/or ≥3 sneezes between the first non-zero dose and approximately 10 minutes after the highest dose of NAC at screening visit.

Exclusion Criteria: The following were exclusion criteria for the study: (1) history of clinically significant cardiovascular, respiratory, hepatic, renal, gastrointestinal, endocrine, hematological, psychiatric, or neurological disease, as assessed by the investigator that may confound the results of the study or pose an additional risk to the subject by study participation; (2) has any physical examination findings and/or history of any illness that, in the opinion of the study investigator, might confound the results of the study or pose an additional risk to the subject by study participation; (3) hospitalization (>24 hours) for any reason within 60 days of the screening visit 1; (4) current cigarette smoker or former smoker (cigarettes or e-cigarettes) who stopped smoking within 3 months prior to screening visit 1; (5) history of drug or alcohol abuse within a year prior to screening visit 1 (Note: drug and alcohol screen must be negative prior to study drug dosing); (6) presence of HIV, hepatitis B, or hepatitis C seropositivity at screening or within 3 months prior to dosing, with the exception of false-positive screening tests as documented by polymerase chain reaction or Western blot; (7) any malignancy within the past 5 years, except for basal cell or squamous epithelial cell carcinomas of the skin or carcinoma in situ of the cervix or anus that have been resected, with no evidence of local recurrence or metastatic disease for 3 years; (8) has an estimated glomerular filtration rate (using the Modification of Diet in Renal Disease study equation or the Chronic Kidney Disease Epidemiology Collaboration equation) of <60 mL/min/1.73 m$^2$ at screening; (9) clinically significant abnormal ECG as assessed by the investigator or with abnormal intervals (QTcF >470 ms for males; >480 ms for females) at screening or prior to dosing and confirmed in a repeat measurement; (10) history of acute hypersensitivity and/or anaphylaxis to protein therapeutics or components of formulation, or allergies that in the opinion of the investigator could represent a substantial risk to the subject; (11) participation in any clinical research study evaluating another investigational drug or therapy within 90 days or at least 5 half-lives (whichever is longer) for an investigational biologic drug, or at least 28 days for other investigational products, or within 6 months for immunotherapy prior to the screening visit of the current trial; (12) unwilling or unable to comply with the permitted and prohibited medication specifications for this study; (13) member of the clinical site study team and/or his/her immediate family, unless prior approval granted by the sponsor; (14) known sensitivity to doxycycline or similar compounds (i.e., tetracyclines); (15) pregnant or breastfeeding women; (16) women of childbearing potential who have a positive pregnancy test result or do not have their pregnancy test result at baseline; (17) women of childbearing potential who are unwilling to practice highly effective contraception prior to start of the first treatment, during the study, and for at least 6 months after the last dose; (18) sexually active men who are unwilling to use the following forms of medically acceptable birth control during the study drug follow-up period and for 6 months after the last dose of study drug: vasectomy with medical assessment of surgical success OR consistent use of a condom. Additional exclusion criteria for Part B: (19) receipt of study drug REGN5713-5714-5715 in Part A; (20) experiences systemic symptoms in response to the NAC at visit 3, including but not limited to wheezing, throat tightening, or shortness of breath; (21) significant rhinitis or sinusitis outside of the birch pollen season or due to daily contact with other allergens causing symptoms, that is expected to coincide with the study NAC assessments as assessed by the investigator; (22) subjects who anticipate major changes in allergen exposure in their home or work environments that are expected to coincide with the study NAC assessments as assessed by the investigator; (23) abnormal lung function as judged by the investigator with FEV1<80% of predicted; (24) a clinical history of asthma requiring chronic medication such as regular, inhaled corticosteroids for >6 months per year; (25) a clinical history of asthma with 2 or more asthma exacerbations requiring hospitalizations or systemic corticosteroids in the previous year; (26) history of significant, recurrent sinusitis, defined as at least 3 episodes requiring antibiotic treatment per year for the last 2 years; (27) history of chronic obstructive pulmonary disease (COPD); (28) history of birch allergy immunotherapy (SCIT, sublingual immunotherapy, or oral immunotherapy) in the 5 years prior to screening; (29) use of anti-IgE or other biological therapy within 6 months prior to screening; (30) allergen-specific immunotherapy with any allergen within 6 months prior to screening; (31) screening ACT <20 at any screening visits.

Study Treatments

REGN5713, REGN5714, and REGN5715 were supplied for this study in the following concentrations for each drug:
REGN5713, REGN5714, and REGN5715 drug products, lyophilized 265 mg in 20 mL vials
REGN5713/REGN5714/REGN5715 placebo product, lyophilized, in 20 mL vials Reconstituted drug was 150 mg/mL for each drug: REGN5713, REGN5714, and REGN5715. Therefore, total injected drug volume (SC) was 1 mL for the 150 mg total dose of REGN5713, REGN5714, and REGN5715 (cohort 1), 3 mL for the 450 mg total dose of REGN5713, REGN5714, and REGN5715 (cohort 2), and 6 mL for the 900 mg total dose of REGN5713, REGN5714, and REGN5715 (cohort 3 and Part B). Multiple syringes could be used for SC injection. For example, 3 syringes (2 mL per syringe) were used to inject SC drug for cohort 3 and Part B. The preferred site for SC injections is the abdomen, but the injections could be given in the abdomen, thigh, or upper arm.

For Part A, there were four cohorts as follows:

| Cohorts | Study Drug Treatment | Dosing | Treatment Administration |
|---|---|---|---|
| Cohort 1 8 subjects/cohort (6 active: 2 placebo) | REGN5713-5714-5715 or placebo | 150 mg SC (50 mg/mAb) | day 1 |
| Cohort 2 8 subjects/cohort (6 active: 2 placebo) | REGN5713-5714-5715 or placebo | 450 mg SC (150 mg/mAb) | day 1 |
| Cohort 3 8 subjects/cohort (6 active: 2 placebo) | REGN5713-5714-5715 or placebo | 900 mg SC (300 mg/mAb) | day 1 |
| Cohort 4 8 subjects/cohort (6 active: 2 placebo) | REGN5713-5714-5715 or placebo | 900 mg IV (300 mg/mAb) | day 1 |

For Part B, REGN5713-5714-5715 at 900 mg SC (300 mg/mAb) or placebo was administered on day 1.

Rescue treatments: If required, subjects who experienced allergic reactions were treated with anti-allergic rescue treatment according to the discretion of the investigator. Subjects could also take oral antihistamines as needed for AR symptoms during the course of the study. However, oral antihistamines were prohibited within 5 days prior to or during a visit for NAC or skin prick testing.

Outcomes Assessed

For both Parts A and B, the primary endpoint was the incidence and severity of treatment-emergent adverse events (TEAEs) reported by the subjects or observed by the investigator and other safety variables in subjects who received REGN5713-5714-5715 administered SC or IV compared to placebo.

Secondary endpoints for Parts A and B were: total concentration of REGN5713, REGN5714, and REGN5715 in serum, at the sampling times specified in the visit schedule; and incidence of treatment-emergent anti-drug antibodies to REGN5713, REGN5714, and REGN5715 in subjects.

Secondary endpoints for Part B only were: change and percent change in area under the curve (AUC) for TNSS (0 to 1 hour post-peak TNSS) in response to a NAC at day 8, 29, and 57 from the pretreatment baseline TNSS AUC (0 to 1 hour post-peak TNSS) for REGN5713-5714-5715 900 mg SC as compared to placebo; and change and percent change in mean wheal diameters of the skin prick test with serial birch allergen titration at day 8, 29, and 57 from the pretreatment baseline for REGN5713-5714-5715 900 mg SC as compared to placebo.

Procedures for assessing efficacy are described below.

Total Nasal Symptom Score (TNSS): The Total Nasal Symptom Score (TNSS), measured on a 0-12 scale, is a composite symptom assessment of congestion, itching, and rhinorrhea (each graded on a 0-3 scale, 3 being severe), and sneezing (3 being >5 sneezes). The TNSS is recorded in response to a NAC at day 8, 29, and 57 from the pretreatment baseline TNSS in response to a NAC, to assess the efficacy of REGN5713-5714-5715 on AR symptoms elicited by a NAC with birch allergen.

Total Ocular Symptom Score (TOSS): The Total Ocular Symptom Score (TOSS), measured on a 0-12 scale, is a composite symptom assessment of ocular symptoms (itching/burning, redness, watering and tearing, and puffiness and swelling). The TOSS score is recorded during the NAC assessments.

Peak Nasal Inspiratory Flow (PNIF): The Peak Nasal Inspiratory Flow (PNIF, L/min) is a measure of nasal patency or nasal congestion. PNIF is measured and recorded during the NAC assessments.

Safety Variables

Safety was assessed throughout the study (Part A and Part B) by reviewing adverse events (AEs), vital signs, 12-lead electrocardiograms (ECGs), physical examinations, and routine laboratory safety tests. In addition, for Part B, spirometry (American Thoracic Society [ATS]/European Respiratory Society [ERS]-compliant), including measurements of forced vital capacity (FVC) (L), forced expiratory volume (FEV1) (L), FEV1/FVC (%), peak expiratory flow (L/s), forced expiratory flow 25 to 75 (L/s), and the asthma control test (ACT) was performed during screening to exclude any subjects with abnormal lung function and/or poorly controlled asthma. The ACT was performed prior to every NAC procedure in all subjects and spirometry was measured prior to the NAC in any subject with a history of asthma. FEV1 must be 80% predicted to perform the NAC in any subject with a history of asthma.

Pharmacokinetic, Pharmacodynamic, and Other Biomarker Variables

Pharmacokinetic variables include the following: concentration of REGN5713, REGN5714, and REGN5715 in serum at each specified time point.

In Part B, a standard SPT with serial allergen titration to birch allergen extract and at least one other birch homologous tree allergen (e.g., alder) is performed at screening visit 1 to assess sensitization status, and on specified study days (e.g., days 8, 29, 57, and 113). Skin prick test data may be used to determine the relationship between birch sensitization at baseline and PD effects of REGN5713-5714-5715 to reduce nasal symptoms upon NAC. A titrated SPT with serial allergen titration, with birch allergen extract, will be performed at screening and at day 29 to assess PD effects of REGN5713-5714-5715 on skin wheal size response (mediated by mast cell degranulation).

Serum antibodies are assessed as follows:
- Allergen-specific IgE levels (birch pollen, Bet v 1) at screening visit 1 (V1) and baseline
- Allergen-specific IgE levels (Bet v 1 and other common allergens) at screening and baseline to assess sensitization status and to evaluate the relationship between response to REGN5713-5714-5715 and poly/mono-sensitization
- Allergen-specific IgE levels (Bet v 1 and other common allergens) on days 8, 29, and 57 using blood samples collected prior to the NAC
- Additional subclass of serum antibodies (e.g., IgG and IgG4 against birch pollen and Bet v 1) may be measured at screening, baseline, and on days 8, 29, and 57, using blood samples collected prior to NAC Additionally, blood may be obtained for additional exploratory research tests to understand better the effects of REGN5713-5714-5715 on birch allergy. This may include the assessment of effective competition between REGN5713-5714-5715 and endogenous serum IgE for allergen binding on an in vitro assay. Serum IgE against other related tree allergies will also be measured to correlate with symptom improvement after treatment with REGN5713-5714-5715. Peripheral blood samples (whole blood, peripheral blood mononuclear cells [PBMC]) may also be collected for the exploratory biomarker research to study changes in ex vivo allergic response to birch pollen and other allergens after treatment. Nasal brushings may be collected from birch-allergic subjects approximately 6 hours after NAC. Changes in the gene signatures of Type 2 inflammatory response after NAC will be analyzed by RNA-seq.

Nasal fluid may be obtained from birch-allergic subjects up to approximately 6 hours after NAC. Type 2 cytokines and chemokines in nasal fluid of birch pollen-allergic subjects will be determined: the levels of Type 2 cytokines (e.g., IL-4, IL-13) and chemokines (e.g. TARC, eotaxin) will be measured up to 6 hours after NAC to assess the suppression of allergic response to birch pollen after treatment with REGN5713-5714-5715.

Results

Study Subjects

In Part A, a total of 32 subjects were randomized (24 subjects to REGN5713-5714-5715 and 8 subjects to placebo). In Part B, a total of 64 subjects were randomized (32 subjects to REGN5713-5714-5715 and 32 subjects to placebo). All subjects randomized in Parts A and B received their intended study treatments and completed the study through the Day 113 end-of-study visit.

Baseline demographics of age, race, ethnicity and BMI were generally similar across treatment groups in Part A (Table 1). Among REGN5713-5714-5715 subjects in Part A, 16 (66.7%) were female, and the average height and weight were 169.2 cm and 67.5 kg, respectively, as compared to 2 (25%) female subjects and an average height and weight of 177.9 cm and 75.6 kg in placebo subjects. In Part B, baseline demographics of age, sex, race, ethnicity, height, weight, and BMI were generally similar across treatment groups (Table 2).

Safety

REGN5713-5714-5715 was generally well tolerated when administered via SC and IV routes. There were no SAEs, no deaths, and no TEAEs leading to study discontinuation in Part A or Part B (Table 3, Table 4). The overall frequency of TEAEs were comparable between REGN5713-5714-5715 (Part A: 88.9%, Part B: 81.3%) and placebo (Part A: 100%, Part B: 93.8%) (Table 3, Table 4). There was no dose-dependent trend in any of the TEAEs. The overall frequency of treatment-related TEAEs were also comparable between REGN5713-5714-5715 (Part A: 25.0%, Part B: 21.9%) and placebo (Part A: 12.5%, Part B: 25.0%) (Table 3, Table 4).

Two injection site reactions were reported in Part A (1 [16.7%] in 450 mg SC REGN5713-5714-5715 arm and 1 [16.7%] in 900 mg SC) and 11 were reported in Part B (5 [15.6%] in 900 mg SC vs. 6 [18.8%] in placebo). All injection site reactions were mild in severity. There was no dose-dependent trend in any of the TEAEs. The TEAEs seen most frequently in Part A in the REGN5713-5714-5715 IV+SC group were headache (29.2% subjects receiving REGN5713-5714-5715 vs. 50.0% subjects receiving placebo), nasopharyngitis (20.8% vs. 62.5%) and abdominal pain (16.7% vs. 25.0%). In Part B, headache (34.4% vs. 28.1%), nasopharyngitis (15.6% vs. 34.4%), and sinusitis (6.3% vs. 15.6%) were the most frequent TEAEs in the REGN5713-5714-5715 group.

TABLE 1

Summary of Demographic and Baseline Characteristics for Part A

| | Placebo Total SC (N = 6) | Placebo Total IV (N = 2) | REGN5713-5714-5715 150 mg SC (N = 6) | REGN5713-5714-5715 450 mg SC (N = 6) | REGN5713-5714-5715 900 mg SC (N = 6) | REGN5713-5714-5715 900 mg IV (N = 6) | Total REGN5713-5714-5715 SC (N = 18) | Total Placebo IV + SC (N = 8) | Total REGN5713-5714-5715 IV + SC (N = 24) |
|---|---|---|---|---|---|---|---|---|---|
| Age (Years) Mean (SD) | 34.3 (14.6) | 36.0 (7.1) | 36.0 (11.7) | 31.7 (14.6) | 36.8 (7.2) | 34.5 (5.9) | 34.8 (11.1) | 34.8 (12.7) | 34.8 (9.9) |
| Sex, n (%) | | | | | | | | | |
| Male | 4 (66.7%) | 2 (100%) | 2 (33.3%) | 2 (33.3%) | 3 (50.0%) | 1 (16.7%) | 7 (38.9%) | 6 (75.0%) | 8 (33.3%) |
| Female | 2 (33.3%) | 0 | 4 (66.7%) | 4 (66.7%) | 3 (50.0%) | 5 (83.3%) | 11 (61.1%) | 2 (25.0%) | 16 (66.7%) |
| Ethnicity, n (%) Not Hispanic or Latino | 6 (100%) | 2 (100%) | 6 (100%) | 6 (100%) | 6 (100%) | 6 (100%) | 18 (100%) | 8 (100%) | 24 (100%) |
| Race, n (%) White | 6 (100%) | 2 (100%) | 6 (100%) | 6 (100%) | 6 (100%) | 6 (100%) | 18 (100%) | 8 (100%) | 24 (100%) |
| Weight (kg), Mean (SD) | 72.9 (11.8) | 83.7 (15.4) | 69.5 (13.3) | 67.4 (11.4) | 69.8 (14.1) | 63.3 (4.2) | 68.9 (12.6) | 75.6 (12.6) | 67.5 (11.0) |
| BMI (kg/m$^2$) Mean (SD) | 23.6 (3.8) | 24.6 (3.6) | 24.5 (3.5) | 23.3 (2.0) | 23.7 (4.1) | 22.7 (2.7) | 23.8 (3.2) | 23.9 (3.5) | 23.5 (3.1) |

TABLE 2

Summary of Demographic and Baseline Characteristics for Part B

| | Placebo Total SC (N = 32) | REGN5713-5714-5715 900 mg SC (N = 32) | Total (N = 64) |
|---|---|---|---|
| Age (Years) Mean (SD) | 39.9 (11.4) | 33.8 (11.2) | 36.9 (11.6) |
| Sex, n (%) | | | |
| Male | 13 (40.6%) | 9 (28.1%) | 22 (34.4%) |
| Female | 19 (59.4%) | 23 (71.9%) | 42 (65.6%) |
| Ethnicity, n (%) Not Hispanic or Latino | 32 (100%) | 32 (100%) | 64 (100%) |
| Race, n (%) | | | |
| White | 32 (100%) | 31 (96.9%) | 63 (98.4%) |
| Black or African American | 0 | 0 | 0 |
| Asian | 0 | 1 (3.1%) | 0 |
| Other | 0 | 0 | 0 |
| Weight (kg), Mean (SD) | 72.6 (12.9) | 71.0 (14.1) | 71.8 (13.4) |
| BMI (kg/m$^2$) Mean (SD) | 24.6 (3.4) | 24.2 (3.2) | 24.4 (3.3) |
| AUC of TNSS (0-1 hr), Mean (SD) | 4.1 (1.4) | 4.1 (1.6) | 4.1 (1.5) |
| Peak TNSS (0-1 hr), Mean (SD) | 7.7 (0.8) | 8.0 (1.0) | 7.8 (0.9) |
| AUC of TOSS (0-1 hr), Mean (SD) | 2.1 (2.2) | 1.3 (1.2) | 1.7 (1.8) |
| AUC of PNIF (0-1 hr), Mean (SD) | 53.1 (27.9) | 59.9 (32.2) | 56.5 (30.1) |
| Screening skin prick test for birch allergen (mm), Mean (SD) | 6.8 (2.0) | 6.5 (1.3) | 6.7 (1.7) |
| AUC of skin prick test with serial birch allergen titration, Mean (SD) | 3.9 (1.3) | 4.1 (1.4) | 4.0 (1.3) |
| AUC of skin prick test with serial alder allergen titration, Mean (SD | 4.9 (1.5) | 5.3 (1.5) | 5.1 (1.5) |
| Bet v 1 IgE, Mean (SD) | 22.9 (29.9) | 22.9 (25.2) | 22.9 (27.5) |
| Birch Silver IgE, Mean (SD) | 23.9 (29.9) | 25.9 (26.4) | 24.9 (28.0) |
| Bet v 2 IgE, Mean (SD) | 0.6 (1.9) | 0.6 (2.1) | 0.6 (2.0) |
| Total IgE, Mean (SD) | 195.7 (307.5) | 251.6 (322.1) | 223.6 (313.7) |

TABLE 3

Overview of Treatment-Emergent Adverse Events for Part A

| | Placebo Total SC (N = 6) | Placebo Total IV (N = 2) | REGN5713-5714-5715 150 mg SC (N = 6) | REGN5713-5714-5715 450 mg SC (N = 6) | REGN5713-5714-5715 900 mg SC (N = 6) | REGN5713-5714-5715 900 mg IV (N = 6) | Total REGN5713-5714-5715 SC (N = 18) | Total Placebo IV + SC (N = 8) | Total REGN5713-5714-5715 IV + SC (N = 24) |
|---|---|---|---|---|---|---|---|---|---|
| Total Number of TEAEs | 27 | 12 | 19 | 15 | 35 | 15 | 69 | 39 | 84 |
| Total Number of Serious TEAEs | 0 | 0 | 0 | 0 | 0 | 0 | 0 | 0 | 0 |
| Total Number of TEAEs with Severe TEAEs | 0 | 0 | 0 | 1 | 1 | 0 | 2 | 0 | 2 |
| Subjects with any TEAE | 6 (100%) | 2 (100%) | 5 (83.3%) | 5 (83.3%) | 6 (100%) | 6 (100%) | 16 (88.9%) | 8 (100%) | 22 (91.7%) |
| Headache | 4 (66.7%) | 0 | 3 (50.0%) | 1 (16.7%) | 2 (33.3%) | 1 (16.7%) | 6 (33.3%) | 4 (50.0%) | 7 (29.2%) |
| Nasopharyngitis | 4 (66.7%) | 1 (50.0%) | 1 (16.7%) | 2 (33.3%) | 2 (33.3%) | 0 | 5 (27.8%) | 5 (62.5%) | 5 (20.8%) |
| Abdominal pain | 1 (16.7%) | 1 (50.0%) | 0 | 1 (16.7%) | 2 (33.3%) | 1 (16.7%) | 3 (16.7%) | 2 (25.0%) | 4 (16.7%) |
| Blood creatine phosphokinase increased | 1 (16.7%) | 0 | 0 | 0 | 2 (33.3%) | 1 (16.7%) | 2 (11.1%) | 1 (12.5%) | 3 (12.5%) |
| Myalgia | 2 (33.3%) | 0 | 0 | 0 | 3 (50.0%) | 0 | 3 (16.7%) | 2 (25.0%) | 3 (12.5%) |
| Toothache | 1 (16.7%) | 0 | 1 (16.7%) | 0 | 2 (33.3%) | 0 | 3 (16.7%) | 1 (12.5%) | 3 (12.5%) |
| Subjects with any Serious TEAE | 0 | 0 | 0 | 0 | 0 | 0 | 0 | 0 | 0 |
| Subjects with any Severe TEAE | 0 | 0 | 0 | 1 (16.7%) | 1 (16.7%) | 0 | 2 (11.1%) | 0 | 2 (8.3%) |
| Subjects with any TEAE Leading to Death | 0 | 0 | 0 | 0 | 0 | 0 | 0 | 0 | 0 |

TABLE 4

Overview of Treatment-Emergent Adverse Events for Part B

| | Placebo Total SC (N = 32) | REGN5713-5714-5715 900 mg SC (N = 32) | Total (N = 64) |
|---|---|---|---|
| Total Number of TEAEs | 89 | 71 | 160 |
| Total Number of Serious TEAEs | 0 | 0 | 0 |
| Total Number of TEAEs with Severe TEAEs | 0 | 0 | 0 |
| Subjects with any TEAE | 30 (93.8%) | 26 (81.3%) | 56 (87.5%) |
| Headache | 9 (28.1%) | 11 (34.4%) | 20 (31.3%) |
| Nasopharyngitis | 11 (34.4%) | 5 (15.6%) | 16 (25.0%) |
| Sinusitis | 5 (15.6%) | 2 (6.3%) | 7 (10.9%) |
| Subjects with any Serious TEAE | 0 | 0 | 0 |
| Subjects with any Severe TEAE | 0 | 0 | 0 |
| Subjects with any TEAE Leading to Death | 0 | 0 | 0 |

Pharmacokinetics

In Part A, after SC administration, the PK profiles exhibited an initial absorption phase with a $T_{max}$ of approximately 8.5 days, followed by a monophasic elimination phase for all three antibodies administered. The half-lives of all three antibodies were similar, with a mean half-life of 25.9±5.0 days for REGN5713 across the three SC doses, 31.7±4.3 days for REGN5714 across the three SC doses, and 34.7±5.9 days for REGN5715 across the three SC doses. REGN5713-5714-5715 concentrations increased in a dose proportional manner, exhibiting dose proportional increases in $AUC_{inf}$ and $C_{max}$, consistent with linear PK for all three antibodies. After IV administration, a rapid initial distribution phase was observed, followed by a monophasic elimination phase. The half-lives of all three antibodies were consistent with SC administration; 26.7±5.0 days, 29.9±4.7 days, and 32.1±5.1 days for REGN5713, 5714, and 5715, respectively. REGN5713 showed slightly higher clearance and lower serum concentrations, and a slightly shorter half-life than REGN5714 and REGN5715, but all three antibodies showed generally similar PK characteristics. Administration of an IV dose allowed for calculation of bioavailability (F) from mean $AUC_{inf}$. Among the three antibodies, F ranged from 70-93% at the various dose levels, with an average F of 72% for REGN5713, 79% for REGN5714, and 88% for REGN5715 across all SC doses.

In Part B, administration of REGN5713-5714-5715 SC in Bet v 1 sensitive patients exhibited similar concentration time profiles to administration in healthy subjects, following linear PK. Visual inspection and graphical overlay of the concentration time profiles showed little difference between Bet v 1 sensitive patients and healthy volunteers.

Efficacy

Figure 1:
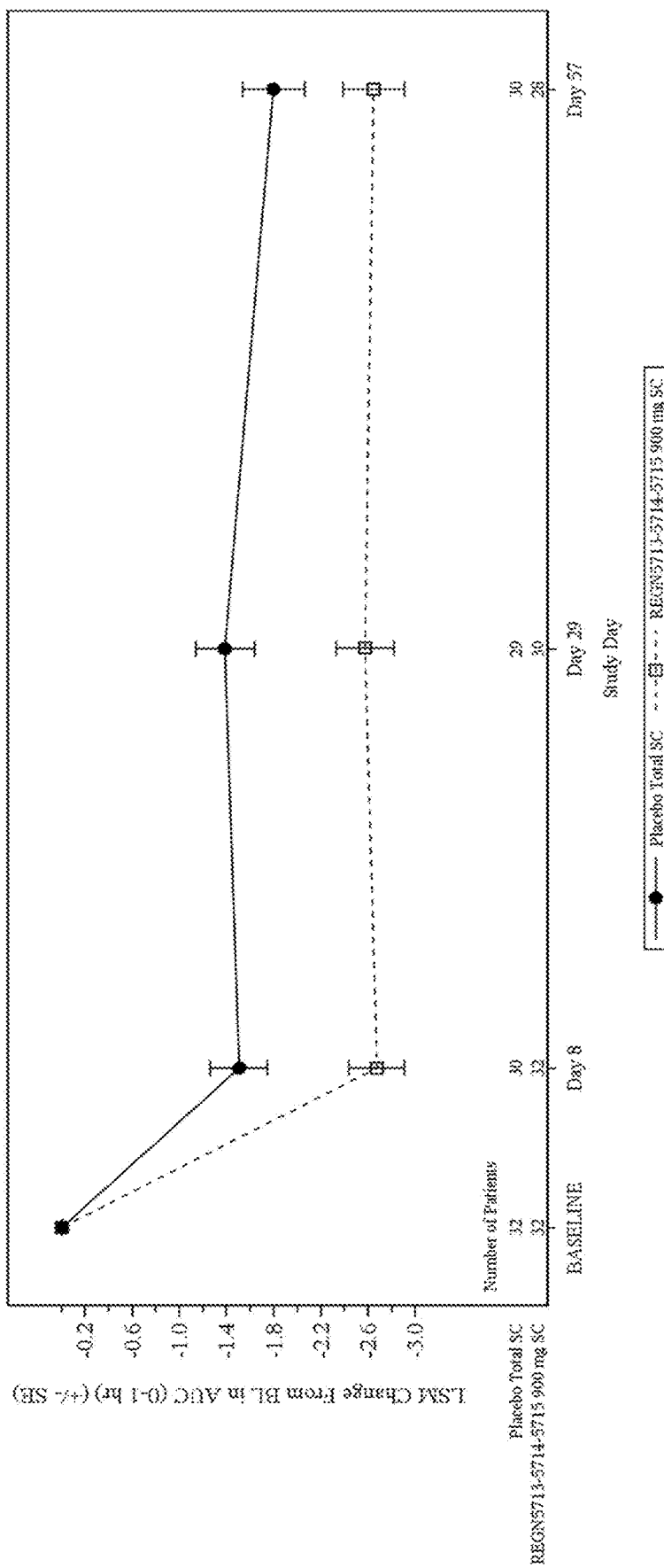
FIG. 1 shows that a single dose of an anti-Bet v 1 antibody cocktail reduced Total Nasal Symptom Score (TNSS) AUC (0-1 hr) after Nasal Allergen Challenge (NAC) on day 8 ($\Delta$-1.2, p=0.001), day 29 ($\Delta$-1.2, p=0.001), and day 57 ($\Delta$-0.9, p=0.024) after dosing as compared to placebo. Least squares mean change in AUC presented, adjusted for the baseline AUC. Circles=placebo; squares=anti-Bet v 1 antibody cocktail.
Figure 2:
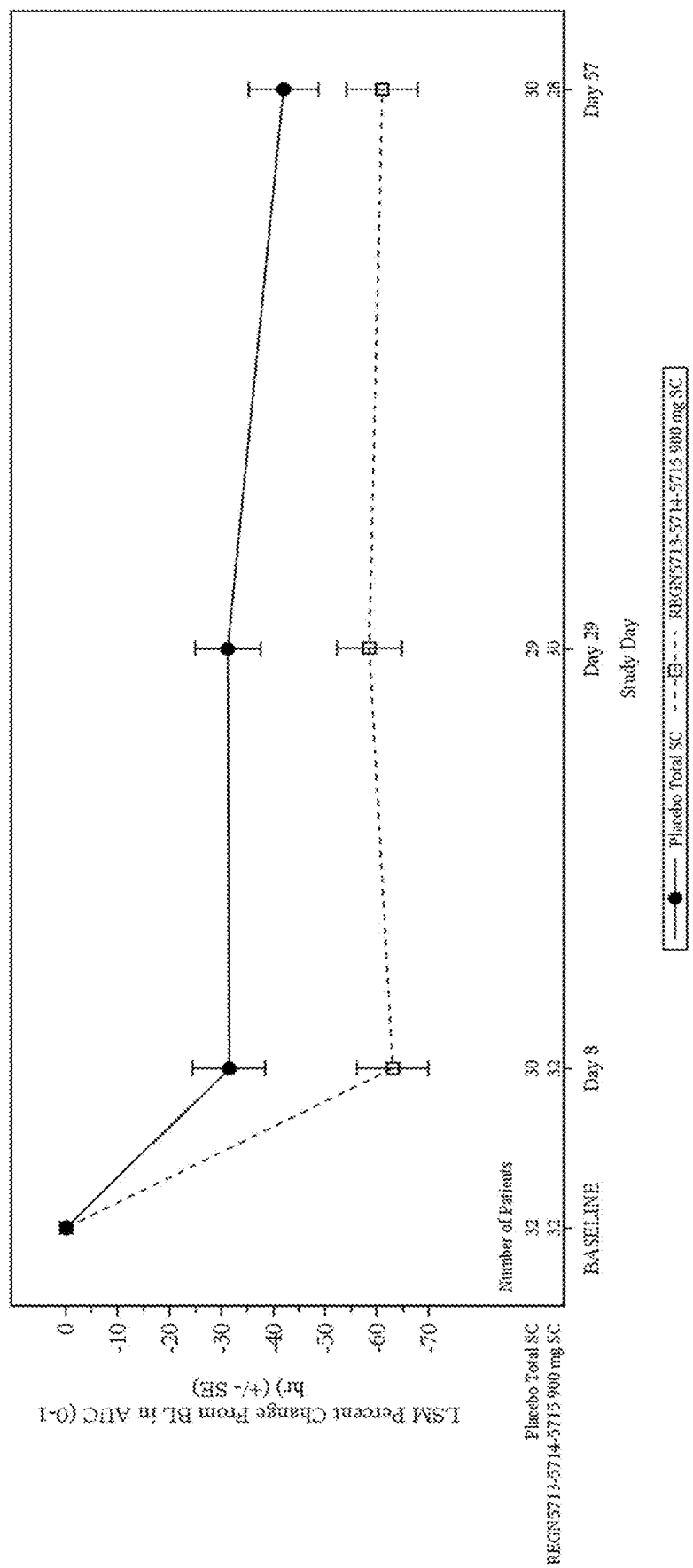
FIG. 2 shows that a single dose of an anti-Bet v 1 antibody cocktail reduced TNSS AUC (0-1 hr) after NAC on day 8 ($\Delta$-32%, p=0.002), day 29 ($\Delta$-27%, p=0.003), and day 57 ($\Delta$-19%, p=0.053) after dosing as compared to placebo, as measured in percent change. Least squares mean percent change in AUC presented, adjusted for the baseline AUC. Circles=placebo; squares=anti-Bet v 1 antibody cocktail.
Figure 3:
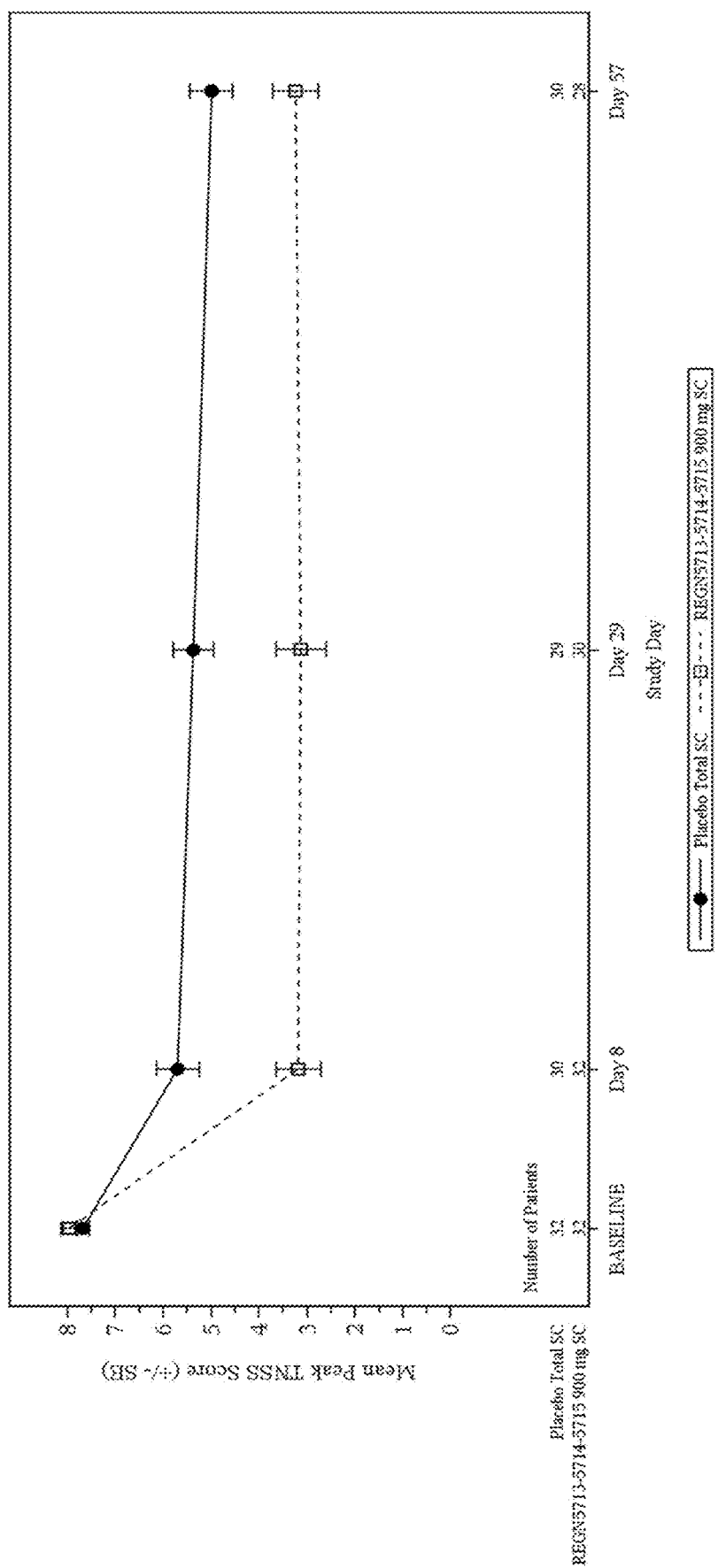
FIG. 3 shows that a single dose of an anti-Bet v 1 antibody cocktail reduced peak TNSS after NAC on day 8 ($\Delta$-35%, p=<0.001), day 29 ($\Delta$-29%, p<0.001), and day 57 ($\Delta$-26%, p=0.003) after dosing as compared to placebo. TNSS in subjects was evaluated at each challenge time point using the specific qualifying dose of allergen that was required for the patient to achieve TNSS at the baseline screening challenge. Circles=placebo; squares=anti-Bet v 1 antibody cocktail.

The key efficacy endpoints assessed in Part B were met. As shown in FIG. 1 and Table 5, a single dose of REGN5713-5714-5715 significantly reduced TNSS AUC (0-1 hr) following NAC as compared to placebo 8, 29 and 57 days after a single dose (placebo-adjusted changes in the TNSS AUC from the baseline NAC of −1.17 [p=0.001], −1.18 [p=0.001] and −0.85 [p=0.024] for study days 8, 29, and 57, respectively). The percent change from baseline yielded similar results, with significant reductions in TNSS AUC (0-1 hr) as compared to the baseline NAC out to Day 57 (placebo-adjusted percent changes in the TNSS AUC from the baseline NAC of −31.57% [p=0.002], −27.35% [p=0.003], and −19.00% [p=0.053] for study days 8, 29, and 57, respectively). See FIG. 2 and Table 5. Treatment with the anti-Bet v 1 cocktail consistently reduced nasal symptoms for two months, with 8 subjects exhibiting 100% reduction in TNSS AUC after 2 months. A decrease in relative treatment efficacy for REGN5713-5714-5715 on day 57 was related to an increase in the placebo-effect (percent reduction in TNSS AUC (0-1 hr) of −31.39%, −31.15% and −41.96% for study days 8, 29, and 57, respectively). The treatment effect of REGN5714-5714-5715 remained consistently around 60% across all study days (percent reduction in TNSS AUC (0-1 hr) of −62.96%, −58.50% and −60.96% for study days 8, 29 and 57, respectively). Treatment with a single dose of REGN5713-5714-5715 also significantly reduced peak TNSS after NAC as compared to placebo at 8, 29 and 57 days. See FIG. 3 and Table 5.

Figure 4A:
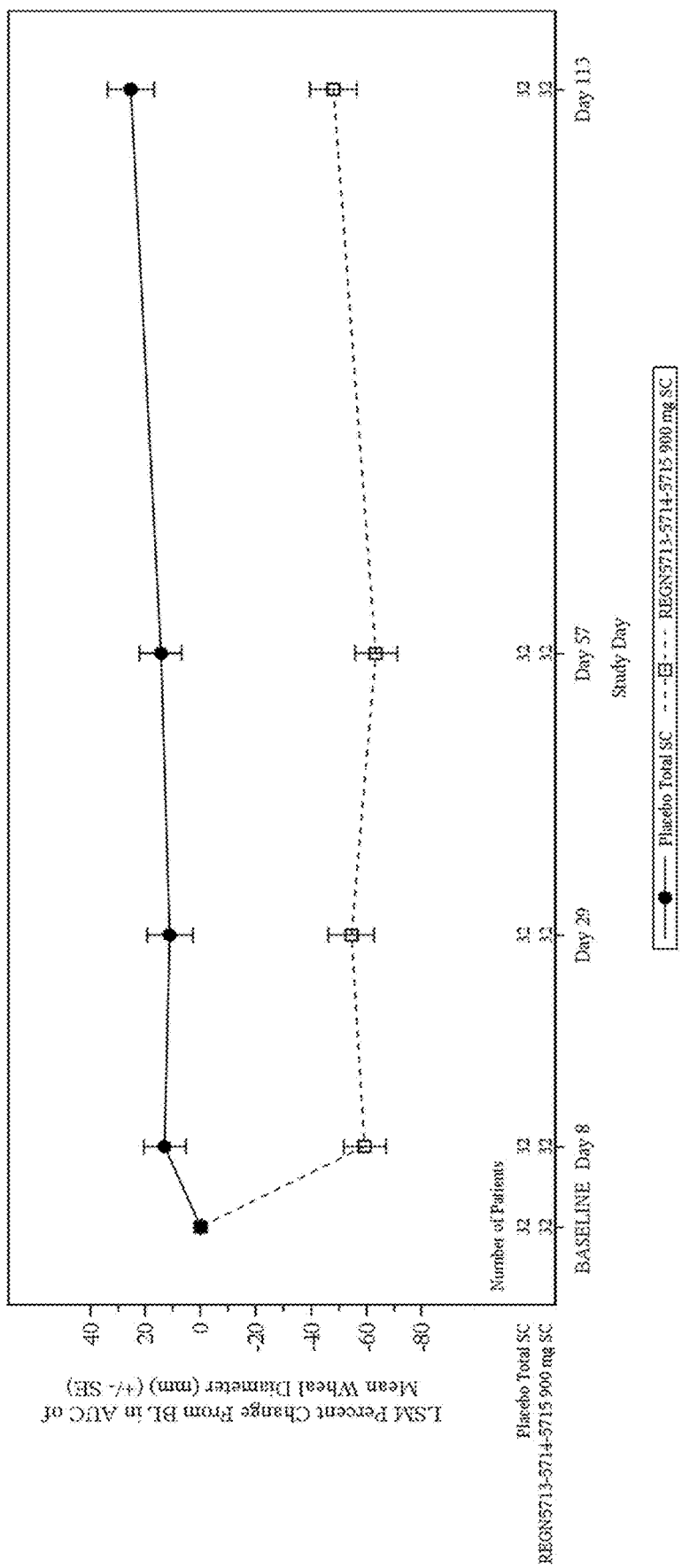
FIG. 4A shows that a single dose of an anti-Bet v 1 antibody cocktail exhibited a durable response in reducing birch sensitization, as measured by percent change from baseline in AUC of mean wheal diameter (mm) in a skin prick test on day 8 ($\Delta$-72%, p<0.001), day 29 ($\Delta$-66%, p<0.001), day 57 ($\Delta$-78%, p<0.001), and day 113 ($\Delta$-74%, p<0.001) as compared to placebo. Circles=placebo; squares=anti-Bet v 1 antibody cocktail.

The mean wheal diameters in the serial birch titration SPT at baseline were similar in the REGN5713-5714-5715 and placebo groups (data not shown), and a similar AUC of mean wheal diameters of 4.14 and 3.93, respectively, was observed in the baseline visit (Table 2). REGN5713-5714-5715 significantly reduced the AUC of the SPT mean wheal diameters relative to placebo out to Day 113 (placebo-adjusted percent changes relative to the baseline SPT of −72.39% [p<0.001], −65.61% [p<0.001], −77.90% [p<0.001], −73.56% [p<0.001] on study days 8, 29, 57 and 113, respectively). See FIG. 4A and Table 5. Thus, a single dose of anti-Bet v 1 cocktail showed a durable response in reducing birch sensitization even 3.5 months after dosing.

TABLE 5

Key Efficacy Endpoints

| Study Day | Placebo | REGN5713-5714-5715 900 mg SC | Difference (Placebo vs. 900 mg SC) | p-value (Placebo vs. 900 mg SC) |
|---|---|---|---|---|
| Change from baseline NAC in the TNSS AUC (0-1 hr) | | | | |
| Day 8 | −1.50 (0.24) | −2.67 (0.24) | −1.17 (0.34) | 0.001 |
| Day 29 | −1.39 (0.25) | −2.57 (0.24) | −1.18 (0.35) | 0.001 |
| Day 57 | −1.79 (0.26) | −2.64 (0.26) | −0.85 (0.37) | 0.024 |
| Percent change from baseline NAC in the TNSS AUC (0-1 hr) | | | | |
| Day 8 | −31.39% | −62.96% | −31.57% | 0.002 |
| Day 29 | −31.15% | −58.50% | −27.35% | 0.003 |
| Day 57 | −41.96% | −60.96% | −19.00% | 0.053 |
| Change from baseline NAC in the TOSS AUC (0-1 hr) | | | | |
| Day 8 | −0.88 (0.13) | −1.36 (0.13) | −0.48 (0.19) | 0.013 |
| Day 29 | −0.85 (0.15) | −1.44 (0.15) | −0.59 (0.21) | 0.007 |
| Day 57 | −0.99 (0.16) | −1.29 (0.16) | −0.30 (0.23) | 0.191 |
| Change from baseline NAC in the PNIF AUC (0-1 hr) | | | | |
| Day 8 | 22.07 (6.25) | 38.53 (6.09) | 16.45 (8.74) | 0.065 |
| Day 29 | 22.37 (6.40) | 47.65 (6.29) | 25.28 (8.98) | 0.007 |
| Day 57 | 33.58 (6.56) | 50.32 (6.61) | 16.74 (9.33) | 0.078 |
| Change from baseline in the skin prick test AUC | | | | |
| Day 8 | 0.11 | −2.43 | −2.54 | <0.001 |
| Day 29 | 0.00 | −2.27 | −2.27 | <0.001 |
| Day 57 | 0.21 | −2.57 | −2.78 | <0.001 |
| Day 113 | 0.50 | −1.97 | −2.46 | <0.001 |
| Percent change from baseline in the skin prick test AUC | | | | |
| Day 8 | 13.12% | −59.27% | −72.39% | <0.001 |
| Day 29 | 11.24% | −54.38% | −65.61% | <0.001 |
| Day 57 | 14.53% | −63.36% | −77.90% | <0.001 |
| Day 113 | 25.58% | −47.98% | −73.56% | <0.001 |

Figure 5A:
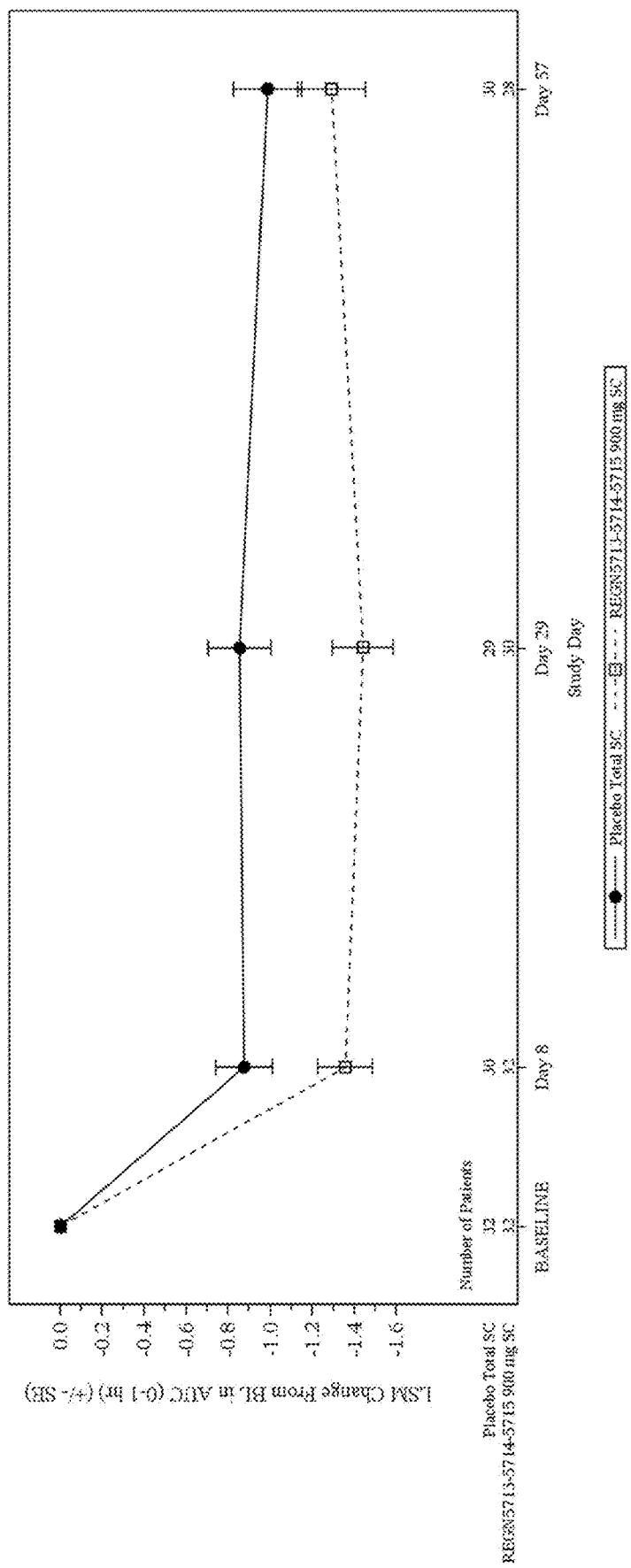
FIG. 5A shows that a single dose of an anti-Bet v 1 antibody cocktail reduced Total Ocular Symptom Score (TOSS) AUC (0-1 hr) after NAC on day 8 ($\Delta$-0.48, p=0.013), day 29 ($\Delta$-0.59, p=0.007), and day 57 ($\Delta$-0.30, p=0.191) after dosing as compared to placebo. Least squares mean change in AUC presented, adjusted for the baseline AUC. Circles=placebo; squares=anti-Bet v 1 antibody cocktail.
Figure 5B:
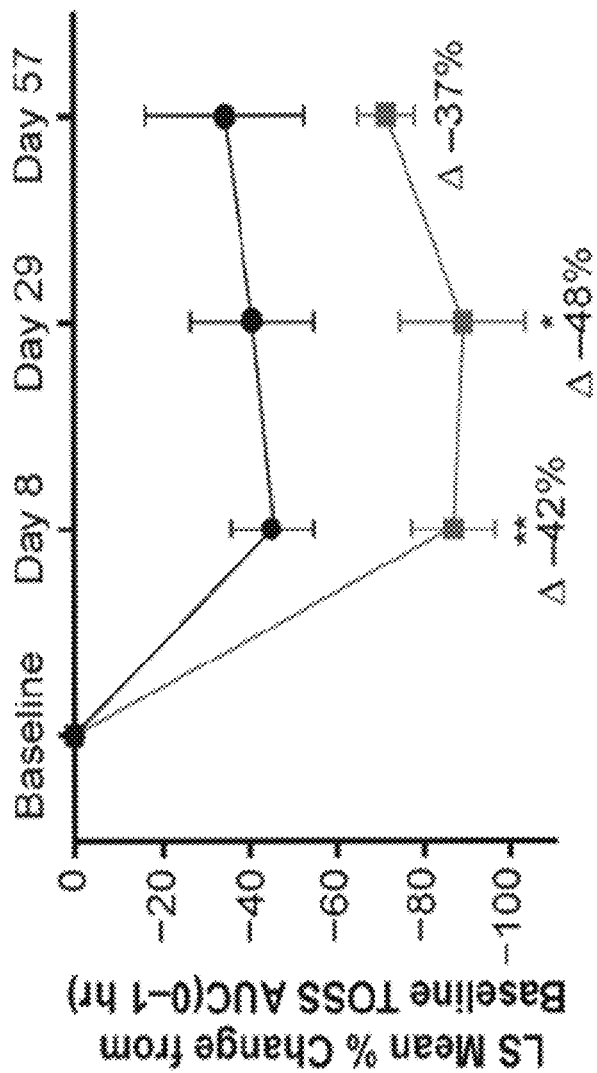
FIG. 5B shows that a single dose of an anti-Bet v 1 antibody cocktail reduced TOSS AUC (0-1 hr) after NAC on day 8 ($\Delta$-42%, p<0.01), day 29 ($\Delta$-48%, p<0.05), and day 57 ($\Delta$-37%) after dosing as compared to placebo, as measured in percent change. Least squares mean percent change in AUC presented, adjusted for the baseline AUC. Circles=placebo; squares=anti-Bet v 1 antibody cocktail.
Figure 6:
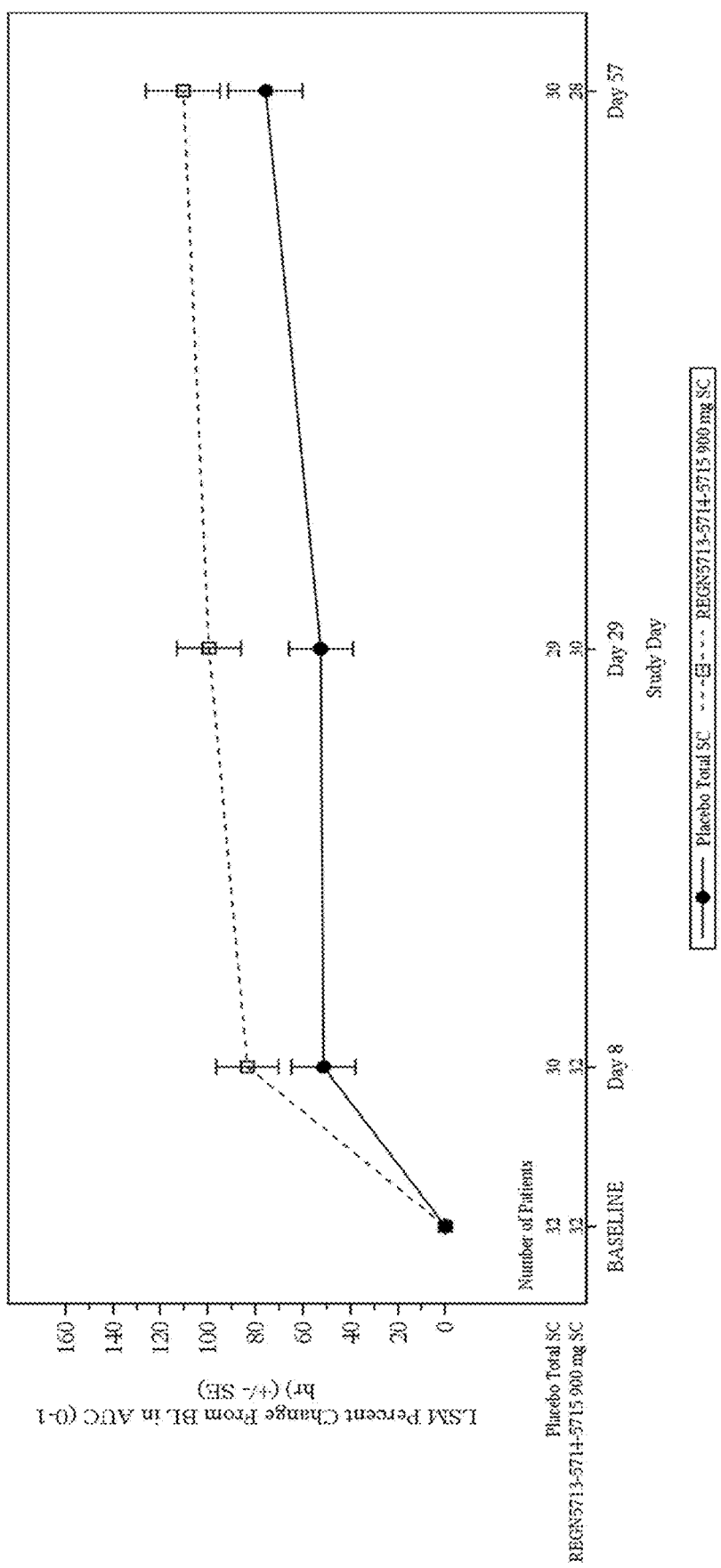
FIG. 6 shows that a single dose of an anti-Bet v 1 antibody cocktail improved peak nasal inspiratory flow (PNIF) on day 8 ($\Delta$32%, p=0.092), day 29 (M7%, p=0.017), and day 57 ($\Delta$35%, p=0.121) as compared to placebo; statistical significance was achieved on day 29. Least squares mean percent change in AUC presented, adjusted for the baseline AUC. Circles=placebo; squares=anti-Bet v 1 antibody cocktail.

At baseline, subjects' NAC-provoked ocular symptoms were minimal; mean TOSS AUC 1.3 and 2.1 in the REGN5713-5714-5715 and placebo groups, respectively (Table 2). As shown in Table 5 and FIGS. 5A-5B, a single dose of REGN5713-5714-5715 significantly reduced TOSS AUC (0-1 hr) following a NAC as compared to placebo 8 and 29 days after dosing, with a trend present on day 57 after dosing (placebo-adjusted changes in the TOSS AUC from the baseline NAC of −0.48 [p=0.013], −0.59 [p=0.007] and −0.30 [p=0.191] for study days 8, 29, and 57, respectively). Two (6.3%) placebo subjects and five (15.6%) REGN5713-5714-5715 subjects had no ocular symptoms at baseline with AUC=0. Additionally, peak nasal inspiratory flow (PNIF) was improved by at least 30% with the anti-Bet v 1 cocktail as compared to placebo, with statistical significance achieved on day 29 (placebo-adjusted percent changes relative to the baseline AUC of 32% [p=0.092], 47% [p=0.017], and 35% [p=0.121] on study days 8, 29, and 57, respectively). See, FIG. 6 and Table 5.

Titration Skin Prick Test for Birch-Homologous Allergen

Figure 4B:
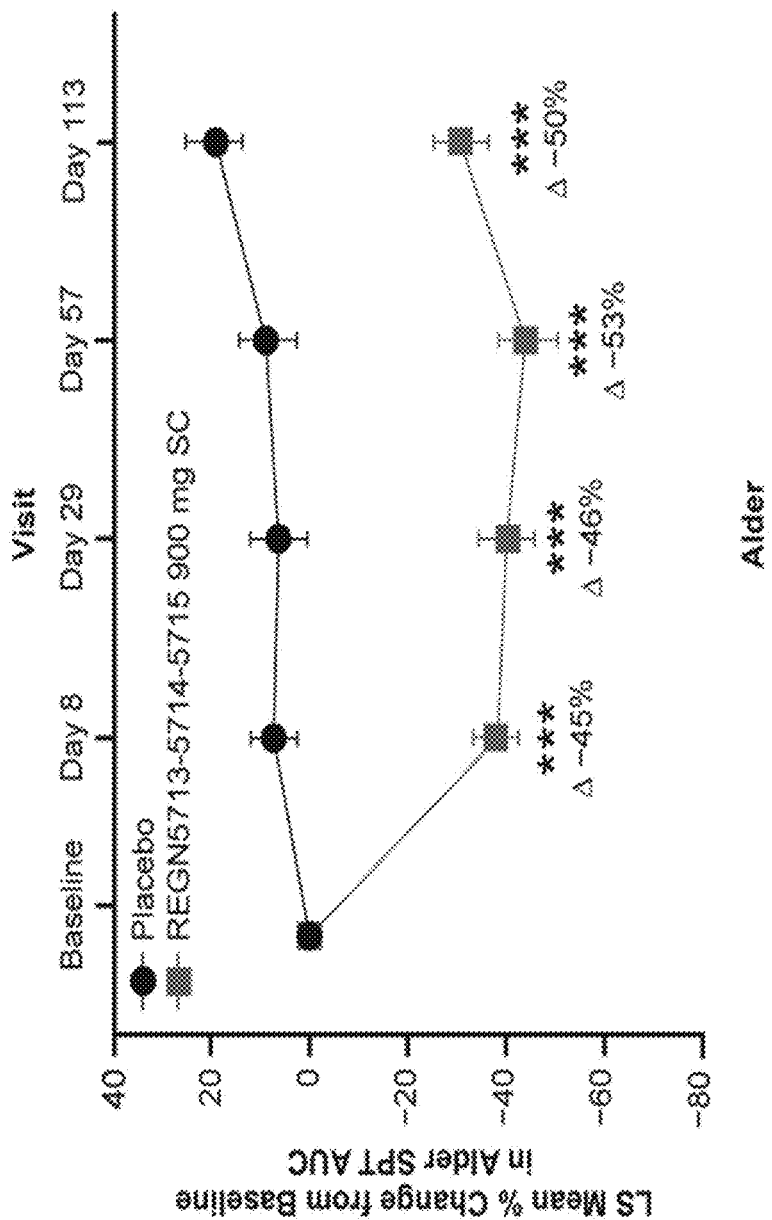
FIG. 4B shows that a single dose of an anti-Bet v 1 antibody cocktail exhibited a durable response in reducing sensitization to alder, as measured by percent change from baseline in AUC of mean wheal diameter (mm) in a skin prick test on day 8 ($\Delta$-45%, p<0.001), day 29 ($\Delta$-46%, p<0.001), day 57 ($\Delta$-53%, p<0.001), and day 113 ($\Delta$-50%, p<0.001) as compared to placebo. Circles=placebo; squares=anti-Bet v 1 antibody cocktail.

AUCs of mean wheal diameters of the serial alder titration SPT at baseline also were similar between the REGN5713-5714-5715 (5.3) and placebo (4.9) groups (Table 2). REGN5713-5714-5715 significantly reduced the AUC of alder SPT mean wheal diameters relative to placebo out to day 113. Placebo-adjusted percent changes relative to the baseline SPT were: −44.7% (day 8, P<0.001), −46.3% (day 29, P<0.001), −52.8 (day 57, P<0.001), −49.8 (day 113, P<0.001). See, FIG. 4B.

Basophil Activation

A biomarker sub-study was conducted for a subset of patients from Part B. Basophil activation assays were performed in a single center on 26 study subjects (13 treated with REGN5713-5714-5715; 13 placebo). Basophil activation is marked by CD63 surface expression; the percentage of basophils that are CD63+ are measured, e.g., by flow cytometry. Increasing concentrations of birch allergen extract were used to stimulate basophils in patient whole blood ex vivo. Basophil responsiveness to allergen stimulation was measured by EC50, which is the concentration of birch allergen required to achieve 50% of maximal basophil activation. Higher EC50 value indicates lower basophil responsiveness to allergen stimulation (i.e., increased suppression of basophil responsiveness). Percent change from baseline EC50 was compared between treatment and placebo groups using a non-parametric test. EC50 for birch was correlated to clinical responses including total nasal symptom score (TNSS) after NAC and SPT.

The basophil activation tests (BATs) were performed using Bühlmann's Flow CAST® kits (Bühlmann Laboratories AG, Switzerland), in which CCR3 and CD63 were used for basophil detection following stimulation of basophils in patients' whole blood ex vivo with seven increasing concentrations of allergen extract (0.0055-22.72 ng/mL) to generate a dose-response curve. Basophil activation was measured by the percentage of basophils positive for CD63 surface expression in flow cytometry analysis. Basophil responsiveness to birch, alder, hazel, apple, and grass mix (Allergen source: Bühlmann Laboratories AG, Switzerland or Biomay AG, Vienna) extract was measured by EC50.

Figure 7A:
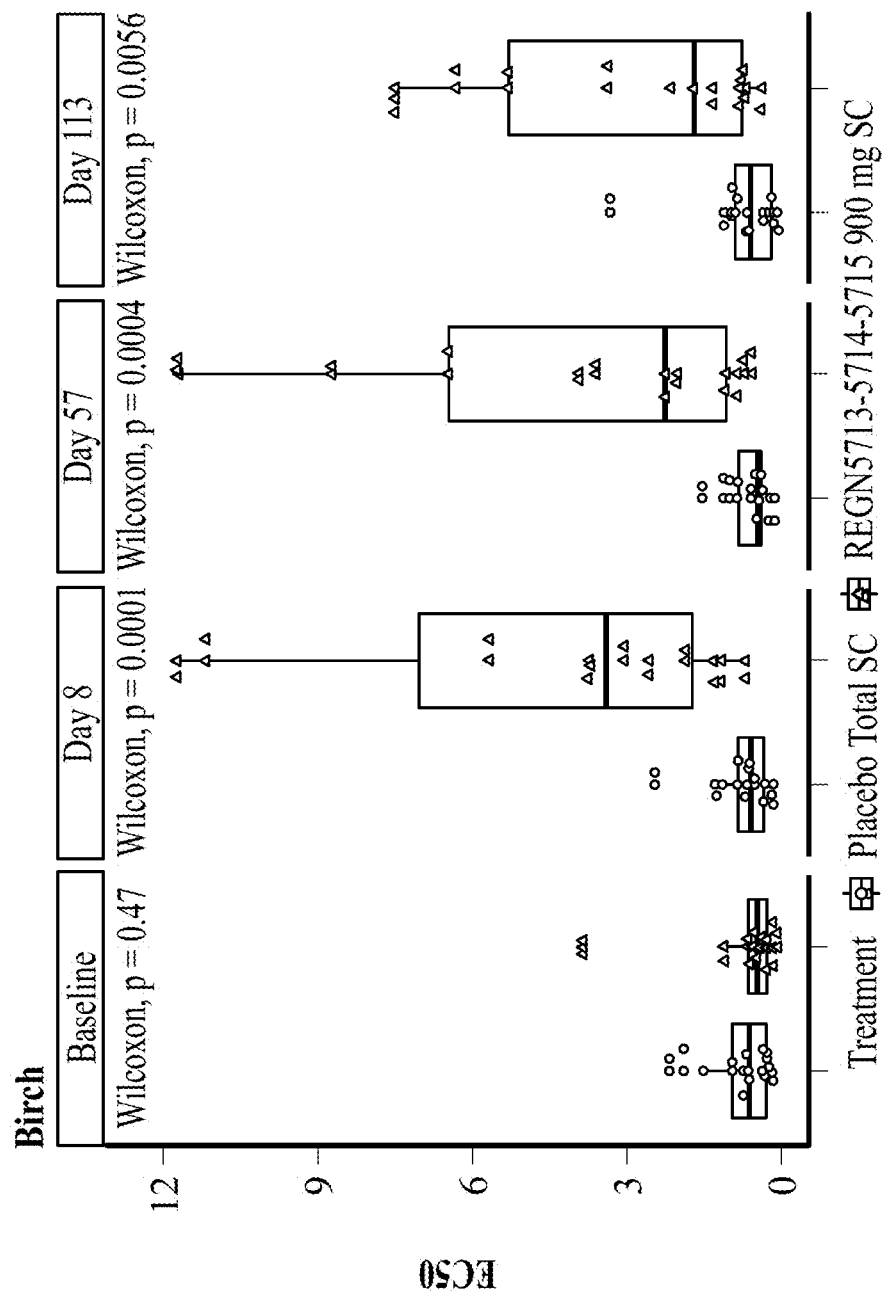
FIG. 7A-7E show that significant suppression of basophil responsiveness to birch, alder, hazel, and apple pollen was observed in patients treated with an anti-Bet v 1 antibody cocktail versus placebo group, while no suppression in basophil response was detected in the grass allergen negative control. (A) Basophil responsiveness to birch pollen extract was measured by EC50. Significant suppression of basophil responsiveness to birch allergen was observed in the treatment group (n=13) versus placebo, as measured by EC value (Days 8, 57 all p<0.001; Day 113 p<0.01). (B) Basophil responsiveness to alder pollen extract was measured by EC50. Significant suppression of basophil responsiveness to alder allergen was observed in the treatment group (n=13) versus placebo (n=13) as measured by percent change from baseline in EC50 (Days 8, 57, 113 all p<0.001). (C) Basophil responsiveness to hazel pollen extract was measured by EC50. Significant suppression of basophil responsiveness to hazel allergen was observed in the treatment group (n=13) versus placebo (n=13) as measured by percent change from baseline in EC50 (Day 8, p<0.001, Day 57 p=0.01). (D) Basophil responsiveness to apple pollen extract was measured by EC50. Significant suppression of basophil responsiveness to apple allergen was observed in the treatment group (n=13) versus placebo (n=13) as measured by percent change from baseline in EC50 (Day 8 p<0.01; Days 57 and 113 p<0.05). (E) Basophil responsiveness to grass pollen extract was measured by EC50.
Figure 7B:
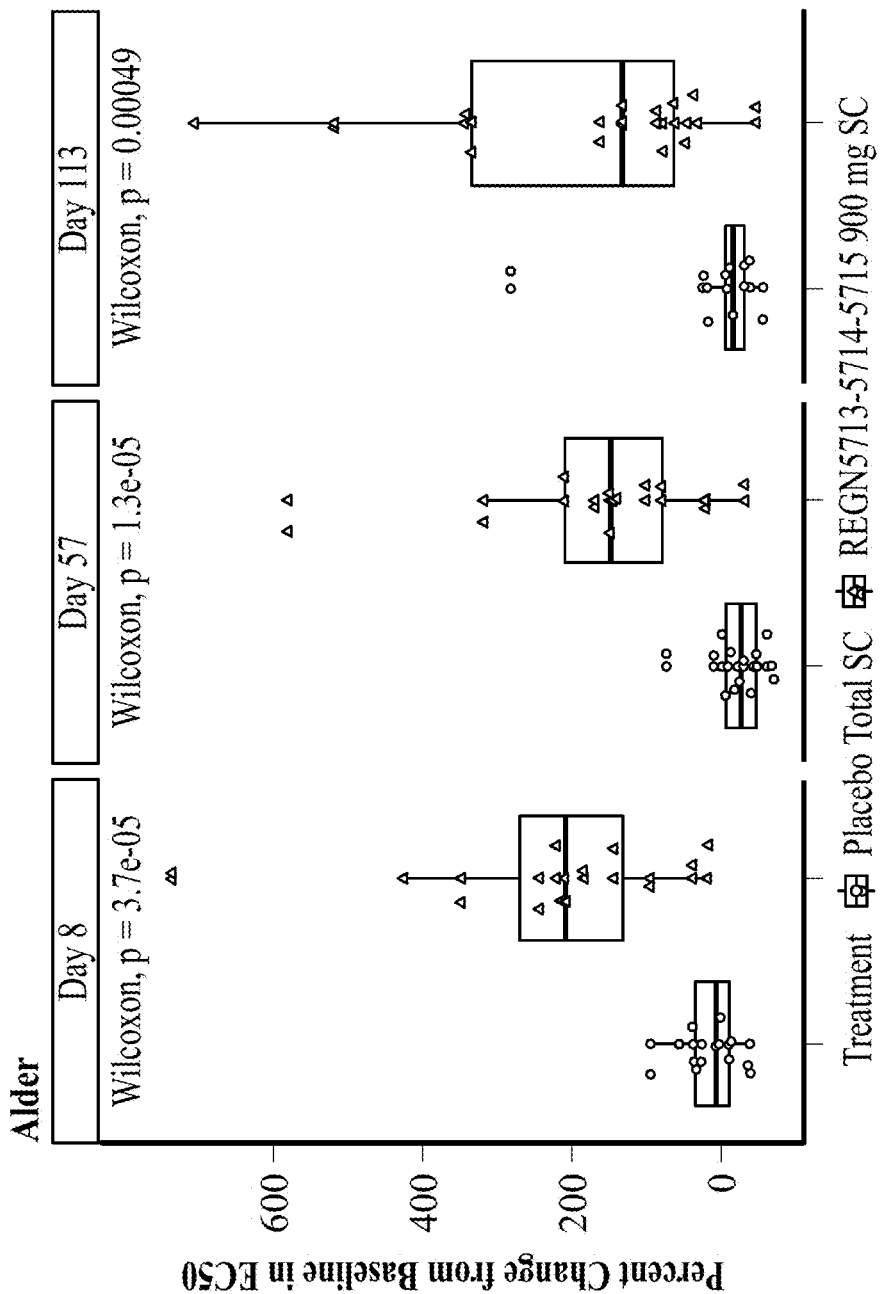
Figure 7C:
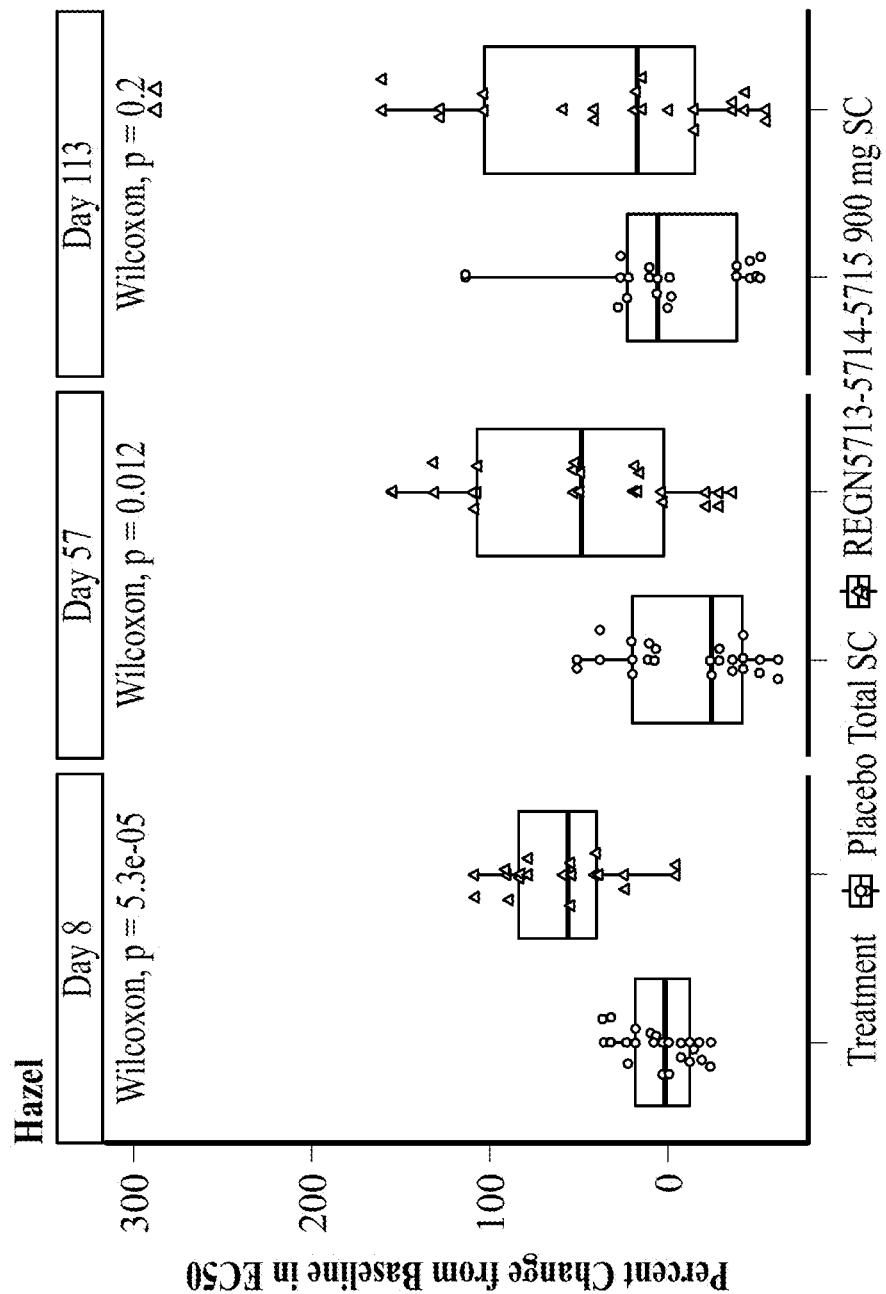
Figure 7D:
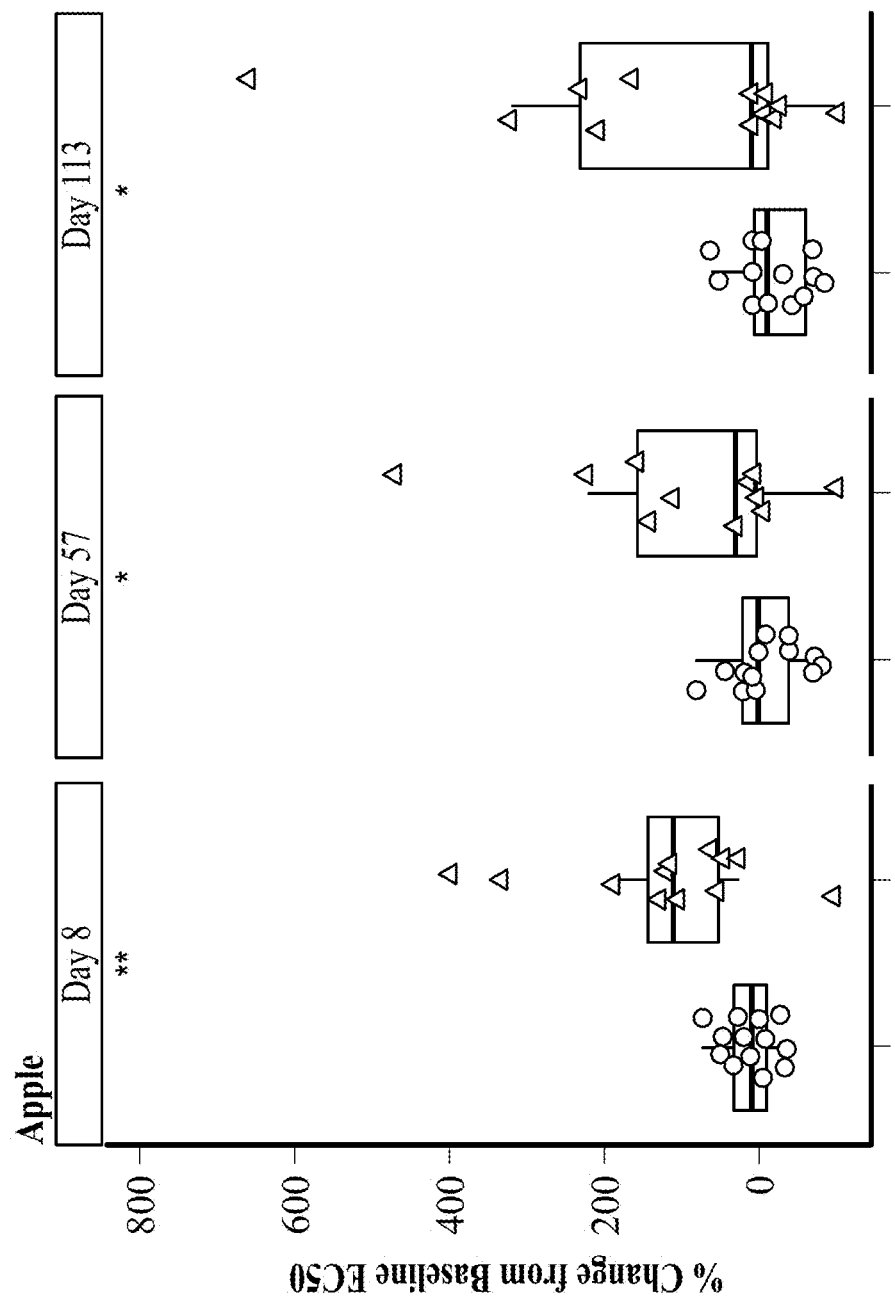
Figure 7E:
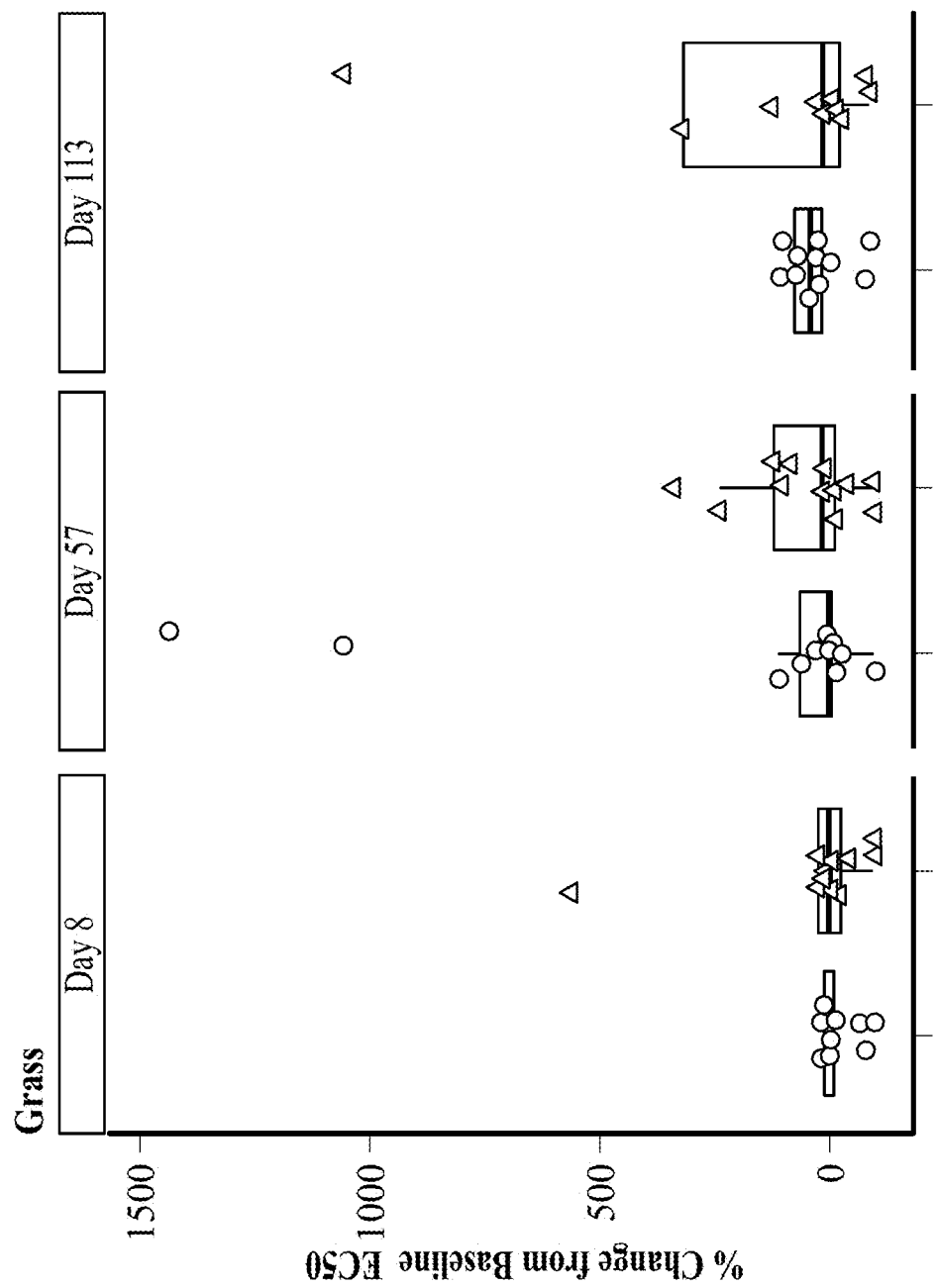

Significant suppression of basophil responsiveness to birch, alder, hazel, and apple pollen extract was observed in treated patients (n=13) versus placebo (n=13) as measured by change from baseline in EC50 (birch and alder: Days 8, 57, 113 all p<0.001; hazel: Day 8, p<0.001, Day 57 p=0.01; apple: Day 8, p<0.01; Days 57 and 113, p<0.05); the highest EC50 was detected on day 8. See, FIGS. 7A-7D. No suppression in basophil response to grass allergen mix (negative control) was detected with REGN5713-5714-5715 treatment (FIG. 7E).

The relationship between basophil suppression and reduction in skin prick test (SPT) was assessed for patients treated with REGN5713-5714-5715. The SPT was performed by pricking the patient's forearm skin with increasing concentrations of birch allergen. Mean Wheal Diameters (MWD) induced at each birch allergen concentration were used for AUC analysis. Inverse correlations were observed in the treatment group between birch basophil activation assay (BAT) EC50 and percent change in birch SPT (Mean wheal diameter) AUC on Day 8 (r=−0.6, p=0.04) and Day 57 (r=−0.57, p=0.04). See, FIG. 8.

The relationship between basophil suppression and TNSS response was also assessed. Analysis of the active treatment group receiving REGN5713-5714-5715 also showed an inverse correlation between percent change in $TNSS_{(0-1\ hr)}$ AUC and EC50 for birch allergen on Day 8, when basophil response to birch stimulation was maximally suppressed (r=−0.71, p=0.0095). See, FIGS. 9A-9B. One subject did not achieve any clinical improvement; no suppression of basophil responsiveness was detected in that subject's blood.

Conclusion

REGN5713-5714-5715 was generally well tolerated when administered by IV or SC routes. There were no deaths or TEAEs leading to treatment or study discontinuation. The concentration time profiles of REGN5713-5714-5715 exhibited linear PK. A single dose of REGN5713-5714-5715 reduced allergic symptoms as measured by TNSS within 8 days and for at least two months and provided a durable response to reduce birch sensitization to study day 113.

Treatment with REGN5713-5714-5715, but not placebo, significantly lowered basophil response to birch pollen extract. Notably, the EC50 for birch allergen correlated with improvements in clinical responses, indicating that the less sensitive the basophils are to birch pollen (i.e., higher EC50), the greater the clinical benefit the patients may achieve. This study suggests that the clinical efficacy of anti-Bet v1 monoclonal antibodies in birch allergic patients may be achieved partly through the suppression of basophils and mast cell mediated allergic responses.

Following treatment with REGN5713-5714-5715, there was significant suppression of basophil responsiveness to alder (r Aln g 1), hazel (r Cor a 1) pollen extract, and apple (r Mal d 1). These data are also consistent with the SPT results which showed that REGN5713-5714-5715 significantly reduced mean wheal diameter after SPT with alder pollen extract. The remarkable inhibitory effect on basophil responses to homologous allergens indicate that REGN5713-5714-5715 as a cocktail may ameliorate allergic response to related tree allergens beyond birch and may treat birch pollen related OAS.

In conclusion, a single subcutaneous dose of REGN5713-5714-5715 is well tolerated and provides a rapid and durable reduction in allergic symptoms post birch-allergen provocation. The suppression of the allergic response to other cross-reacting allergens by the novel Bet v 1 mAb cocktail may offer a convenient, fast and long-acting therapy for the prevention and treatment of seasonal birch and related allergies. The three-antibody cocktail targeting the dominant birch allergen, Bet v 1, provides substantial clinical improvement in most patients.

Example 2: Clinical Trial Investigating the Efficacy of Anti-Bet v 1 Monoclonal Antibodies to Reduce Symptoms of Seasonal Allergic Rhinitis Study Design and Objectives This example describes a Phase 3, multi-center, randomized, double-blind, placebo-controlled, parallel group study to assess the efficacy of anti-Bet v 1 monoclonal antibodies to reduce allergic rhinitis and conjunctivitis symptoms and the use of rescue medications during birch pollen season (NCT04709575).

The primary objective is to assess the reduction of allergic symptoms as measured by combined symptom and medication score (CSMS) during birch pollen season after a single dose of REGN5713-5714-5715 versus placebo. The secondary objectives are: (1) to assess the reduction of allergic symptoms and use of allergy-relieving medications after a single dose of REGN5713-5714-5715 versus placebo, as measured by the total symptom score (TSS), total nasal symptom score (TNSS), total ocular symptom score (TOSS), and daily medication score (DMS); (2) to evaluate the safety and tolerability of REGN5713-5714-5715, including the incidence of hypersensitivity reactions and local injection site reactions; (3) to evaluate the reduction in early allergic response to birch allergen after a single dose of REGN5713-5714-5715 versus placebo, as measured by skin prick test (SPT) mean wheal diameter; (4) to determine systemic exposure of total antibody (i.e., free and antigen-bound) in the form of concentration of REGN5713, REGN5714, and REGN5715 in serum; (5) to assess the immunogenicity to REGN5713, REGN5714, and REGN5715 in subjects after a single dose of REGN5713-5714-5715; and (6) to evaluate "well days" (defined as days when the TSS is without the use of anti-allergy rescue medications).

The total study duration is approximately 28 weeks including screening, dependent on the start and end times of the local birch pollen season. The length of birch pollen season will vary based on geography. Approximately 300 birch-allergic subjects will be randomized 1:1 to REGN5713-5714-5715 or placebo.

Patient Population

This study will enroll generally healthy adult male and female subjects with birch allergy.

Inclusion Criteria: A subject must meet the following criteria to be eligible for inclusion in the study: (1) generally healthy men and women 18 years of age and older at the time of screening; (2) documented or subject-reported history of birch pollen-triggered allergic rhinitis symptoms, with or without conjunctivitis, for at least 2 years; (3) positive SPT with birch pollen extract (i.e., mean wheal diameter at least 5 mm greater than a negative control) in the screening period; (4) positive sIgE tests for birch pollen and Bet v 1 (i.e., kUa/L) in the screening period; (5) willing and able to comply with clinic visits and study-related procedures; (6) provide informed consent signed by study subject or legally acceptable representative; (7) able to understand and complete study-related questionnaires.

Exclusion Criteria: A subject who meets any of the following criteria will be excluded from the study: (1) participation in a prior REGN5713-5714-5715 clinical trial; (2) recurrent or chronic rhinitis or sinusitis not associated with birch pollen season, or due to daily contact with other allergens causing symptoms that are expected to coincide with birch pollen season, as assessed by the investigator; (3) subjects who anticipate major changes in allergen exposure in their home or work environments that are expected to coincide with study assessments, per investigator discretion; (4) persistent chronic or recurring acute infection requiring treatment with antibiotics, antivirals, or antifungals, or any untreated respiratory infections within 4 weeks prior to screening. Participants may be re-evaluated for eligibility after symptoms resolve; (5) documentation of active SARS-CoV-2 infection; (6) abnormal lung function as judged by the investigator with FEV1<70% of predicted at screening or randomization; (7) a clinical history of moderate to severe asthma with 2 or more asthma exacerbations requiring hospitalizations or systemic corticosteroids in the previous year; (8) history of significant, recurrent sinusitis, defined as at least 3 episodes requiring antibiotic treatment per year for the last 2 years prior to screening; (9) history of nasal polyps; (10) active lung disease other than asthma; (11) history of birch or related tree allergy immunotherapy (SCIT, SLIT, or oral immunotherapy) within 5 years prior to screening; (12) use of anti-IgE or other biological therapy that modifies Type 2 inflammation within 6 months prior to screening; (13) allergen-specific immunotherapy with any allergen other than birch within 6 months prior to screening; (14) history of clinically significant cardiovascular, respiratory, hepatic, renal, gastrointestinal, endocrine, hematological, psychiatric, or neurological disease that, in the opinion of the study investigator, might confound the results of the study or pose an additional risk to the subject by study participation; (15) any physical examination findings and/or history of any illness that, in the opinion of the study investigator, might confound the results of the study or pose an additional risk to the subject by study participation; (16) subjects with any laboratory findings showing evidence of organ dysfunction or any clinically significant deviation from the normal range, as decided by the investigator at the screening visit, including but not limited to: (a) clinically significant/active underlying hepatobiliary disease, or (b) abnormal laboratory values at screening, such as neutrophils <1.5×10$^3$/μL or platelets <100,000 cells/mm$^3$; (17) history of drug or alcohol abuse within a year prior to screening; (18) any malignancy within the past 5 years, except for basal cell or squamous epithelial cell carcinomas of the skin or carcinoma in situ of the cervix or anus that have been resected, with no evidence of local recurrence or metastatic disease for 3 years; (19) clinically significant abnormal ECG in the screening period as assessed by the investigator; (20) history of acute hypersensitivity and/or anaphylaxis to excipients in the study medication or allergies that could represent a substantial risk to the subject in the opinion of the investigator; (21) treatment with an investigational drug or therapy within 2 months or at least 5 half-lives (if known), whichever is longer; (22) unwilling or unable to comply with the permitted and prohibited medication specifications for this study; (23) member of the clinical site study team and/or his/her immediate family, unless prior approval granted by the Sponsor; (24) pregnant or breastfeeding women; (25) women of childbearing potential (WOCBP)* who are unwilling to practice highly effective contraception prior to study drug administration, during the study, and for at least 6 months after the dose of study medication; (26) sexually active men who are unwilling to use the following forms of medically acceptable birth control during the study drug follow-up period and for 6 months after the study drug administration: vasectomy with medical assessment of surgical success or consistent use of a condom.

Study Treatments

REGN5713, REGN5714, and REGN5715 are provided individually in open-label vials in carton. Each 20 mL vial contains 265 mg of lyophilized protein. Matching placebo is provided as a lyophilized powder in 20 mL open-label vials in carton. Instructions are provided in the pharmacy manual to create the following treatments:

single subcutaneous (SC) dose of REGN5713-5714-5715 900 mg (300 mg per mAb)
single SC dose of matching placebo that replaces REGN5713-5714-5715

Subjects will be provided with the following medications to treat allergic symptoms during the study:

desloratadine 5 mg (second generation antihistamine)
olopatadine 1 mg/mL (antihistamine eye drop)
mometasone furoate 50 ug/dose (intranasal steroid)

From the time of study drug dosing throughout the birch pollen season, subjects will be asked to record their daily medication use using an e-diary, including information regarding which medications was used and the amount of the pre-specified medications that was used. Utilization of rescue medications should be initiated when subjects reach a symptoms threshold of approximately TSS≥4/18. Subjects will be provided with training to understand the severity of symptoms associated with a TSS≥4/18. Subjects should be instructed not to utilize rescue medications in the anticipation of the birch pollen season. Subjects should also be instructed not to utilize antihistamines (i.e., desloratadine or olopatadine) for 5 days before the end of study visit.

Subjects will be randomized 1:1 to REGN5713-5714-5715 or matching placebo. Randomization will be stratified based on the following:

Serum specific birch pollen IgE levels at screening (<17.5 kUa/L versus 17.5 kUa/L)
In North America only: serum specific oak pollen IgE levels at screening (<0.7 kUa/L versus ≥0.7 kUa/L)
Geographical region (North America versus Europe)

Efficacy Procedures

Procedures for assessing efficacy are described below.

Total Nasal Symptom Score (TNSS): The TNSS ranges from 0 to 12 and is based on assessment of 4 nasal symptoms graded on a Likert scale ranging from 0 (none) to 3 (severe) for congestion, itching, and rhinorrhea, and for sneezing. The TNSS will be recorded using an e-diary.

Total Ocular Symptom Score (TOSS): The TOSS ranges from 0 to 6 and is based on 2 symptoms: itching/redness/gritty feeling and tearing/watering. Each of the 2 symptoms is graded 0 (absent), 1 (mild), 2 (moderate), or 3 (severe). The TOSS will be recorded using an e-diary.

Total Symptom Score (TSS): TSS is calculated by adding the TNSS and TOSS together, for a combined TSS of 0 to 18.

Daily Medication Score: Subjects will be asked to record their daily rescue medication use using an e-diary, including which medications and the amount of these pre-specified medications. This information will be used to calculate the DMS as follows: desloratadine 5 mg 6 points/dose; maximum daily score 6 points, olopatadine 1 mg/mL each drop 1.5 points/drop; maximum daily score 6 points, mometasone furoate 50 μg/dose 2.0 points/spray; maximum daily score 8 points). The maximum DMS score is 20.

Combined Symptom and Medication Score (CSMS): The CSMS is calculated by adding the DMS and TSS together, with scores ranging between 0 and 38.

Asthma Control Questionnaire (ACQ): The ACQ measures the adequacy of asthma control and change in asthma control that occurs spontaneously or as a result of treatment. The ACQ-5 is comprised of 5, patient-reported items that were rated by clinicians as the most important to evaluate control: (1) awakening at night due to symptoms, (2) morning symptoms, (3) limitation of daily activities, (4) shortness of breath, and (5) wheezing. The total score ranges from 0 to 6 with higher scores denoting less asthma control. A score of is considered as uncontrolled asthma. The ACQ-5 will be recorded using an e-diary.

Standardized Rhinoconjunctivitis Quality of Life Questionnaire (RQLQ (S)): The RQLQ (S) has 28 questions in 7 domains: activity limitation, sleep problems, nose symptoms, eye symptoms, non-nose/eye symptoms, practical problems, and emotional function. There are 3 subject-specific questions in the activity domain that allow subjects to select 3 activities in which they are most limited by their rhinoconjunctivitis. Subjects recall how bothered they have been by their rhinoconjunctivitis during the previous week and respond to each question on a 7-point scale (0 [not impaired at all] to 6 [severely impaired]). The overall RQLQ (S) score is the mean of all 28 responses, and the individual domain scores are the means of the items in those domains. The RQLQ (S) will be recorded using an e-diary.

Pollen Food Allergy Symptom Questionnaire (PFASQ): The PFASQ will be performed at specified time points to determine the types of food that produce an allergic reaction, the type of reaction, and how soon the reactions occur.

Patient Global Impression of Severity (PGI-S): The PGI-S assesses the severity of seasonal allergy symptoms over the past 1 week. Symptom severity ranges from 0 (no symptoms), 1 (mild), 2 (moderate), and 3 (severe) symptoms.

| Informal Sequence Listing | | |
|---|---|---|
| SEQ ID NO | Sequence | Description |
| 1 | QVQLQESGPGLVKPSETLSLTCSVSGGSITNYFWTWIRQSPGKGLEWIGYIYYSGGTNYNP SLKSRVTISIDTSKNQFSLNMNSVTAADTAVYYCAGSYYYGVDVWGQGTTVTVSS | REGN5713 heavy chain variable region |
| 2 | GGSITNYF | REGN5713 HCDR1 |
| 3 | IYYSGGT | REGN5713 HCDR2 |
| 4 | AGSYYYGVDV | REGN5713 HCDR3 |
| 5 | EIVLTQSPATLSLSPGERATLSCRASQSIKSFLAWYRQKPGQAPRLLIYDASNRPTGIPARFS GSGSGTDFTLTINSLESEDFAVYFCQQRNNWPFTFGPGTKVDIK | REGN5713 light chain variable region |
| 6 | QSIKSF | REGN5713 LCDR1 |
| 7 | DAS | REGN5713 LCDR2 |
| 8 | QQRNNWPFT | REGN5713 LCDR3 |
| 9 | QVQLQESGPGLVKPSETLSLTCSVSGGSITNYFWTWIRQSPGKGLEWIGYIYYSGGTNYNP SLKSRVTISIDTSKNQFSLNMNSVTAADTAVYYCAGSYYYGVDVWGQGTTVTVSSASTKG PSVFPLAPCSRSTSESTAALGCLVKDYFPEPVTVSWNSGALTSGVHTFPAVLQSSGLYSLSS VVTVPSSSLGTKTYTCNVDHKPSNTKVDKRVESKYGPPCPPCPAPEFLGGPSVFLFPPKPKD TLMISRTPEVTCVVVDVSQEDPEVQFNWYVDGVEVHNAKTKPREEQFNSTYRVVSVLTVL HQDWLNGKEYKCKVSNKGLPSSIEKTISKAKGQPREPQVYTLPPSQEEMTKNQVSLTCLVK GFYPSDIAVEWESNGQPENNYKTTPPVLDSDGSFFLYSRLTVDKSRWQEGNVFSCSVMH EALHNHYTQKSLSLSLGK | REGN5713 heavy chain |
| 10 | EIVLTQSPATLSLSPGERATLSCRASQSIKSFLAWYRQKPGQAPRLLIYDASNRPTGIPARFS GSGSGTDFTLTINSLESEDFAVYFCQQRNNWPFTFGPGTKVDIKRTVAAPSVFIFPPSDEQL KSGTASVVCLLNNFYPREAKVQWKVDNALQSGNSQESVTEQDSKDSTYSLSSTLTLSKADY EKHKVYACEVTHQGLSSPVTKSFNRGEC | REGN5713 light chain |
| 11 | EVQLVESGGDLVQPGGSLRLSCAASGFTFSSYEMNWVRQAPGKGLEWVSFISDSSSNIVY ADSVKGRFTISRDNAKKSLYLQMTSLRAEDTAVYYCAREAIGSTSFDNWGQGTLVTVSS | REGN5714 heavy chain variable region |
| 12 | GFTFSSYE | REGN5714 HCDR1 |
| 13 | ISDSSSNI | REGN5714 HCDR2 |
| 14 | AREAIGSTSFDN | REGN5714 HCDR3 |
| 15 | EIVMTQSPATLSVSPGERATLSCRASQSVSSSLAWYQQKPGQAPRRLIYSASTRATGIPARF SGSGSGTEFTLTISSLQSEDFAIYYCHQYNNWPLTFGGGTKVEIK | REGN5714 light chain variable region |
| 16 | QSVSSS | REGN5714 LCDR1 |
| 17 | SAS | REGN5714 LCDR2 |
| 18 | HQYNNWPLT | REGN5714 LCDR3 |
| 19 | EVQLVESGGDLVQPGGSLRLSCAASGFTFSSYEMNWVRQAPGKGLEWVSFISDSSSNIYY ADSVKGRFTISRDNAKKSLYLQMTSLRAEDTAVYYCAREAIGSTSFDNWGQGTLVTVSSAS TKGPSVFPLAPCSRSTSESTAALGCLVKDYFPEPVTVSWNSGALTSGVHTFPAVLQSSGLYS LSSVVTVPSSSLGTKTYTCNVDHKPSNTKVDKRVESKYGPPCPPCPAPEFLGGPSVFLFPPK PKDTLMISRTPEVTCVVVDVSQEDPEVQFNWYVDGVEVHNAKTKPREEQFNSTYRVVSV LTVLHQDWLNGKEYKCKVSNKGLPSSIEKTISKAKGQPREPQVYTLPPSQEEMTKNQVSLT CLVKGFYPSDIAVEWESNGQPENNYKTTPPVLDSDGSFFLYSRLTVDKSRWQEGNVFSCS VMHEALHNHYTQKSLSLSLGK | REGN5714 heavy chain |
| 20 | EIVMTQSPATLSVSPGERATLSCRASQSVSSSLAWYQQKPGQAPRRLIYSASTRATGIPARF SGSGSGTEFTLTISSLQSEDFAIYYCHQYNNWPLTFGGGTKVEIKRTVAAPSVFIFPPSDEQL KSGTASVVCLLNNFYPREAKVQWKVDNALQSGNSQESVTEQDSKDSTYSLSSTLTLSKADY EKHKVYACEVTHQGLSSPVTKSFNRGEC | REGN5714 light chain |
| 21 | QVQLVQSGAEVKKPGASVKVSCKASGYTFISYNIFWVRQATGQGLDWMGWMNPFRNN AGYAQKFQGRVTVTWDTSISTAYMELSSLSSEDTAIYYCAREHGSSWGFFDYWGQGTLVT VSS | REGN5715 heavy chain variable region |
| 22 | GYTFISYN | REGN5715 HCDR1 |
| 23 | MNPFRNNA | REGN5715 HCDR2 |
| 24 | AREHGSSWGFFDY | REGN5715 HCDR3 |
| 25 | EIVLTQSPGTLSLSPGERATLSCRASQSVSSSYLAWYQQKPGQAPRLLIYGASSRATGIPDRF SGSGSGTDFTLTISRLEPEDFAVYYCQQYGSSPWTFGQGTKVEIK | REGN5715 light chain variable region |

Informal Sequence Listing

| SEQ ID NO | Sequence | Description |
|---|---|---|
| 26 | QSVSSSY | REGN5715 LCDR1 |
| 27 | GAS | REGN5715 LCDR2 |
| 28 | QQYGSSPWT | REGN5715 LCDR3 |
| 29 | QVQLVQSGAEVKKPGASVKVSCKASGYTFISYNIFWVRQATGQGLDWMGWMNPFRNN AGYAQKFQGRVTVTWDTSISTAYMELSSLSSEDTAIYYCAREHGSSWGFFDYWGQGTLVT VSSASTKGPSVFPLAPCSRSTSESTAALGCLVKDYFPEPVTVSWNSGALTSGVHTFPAVLQS SGLYSLSSVVTVPSSSLGTKTYTCNVDHKPSNTKVDKRVESKYGPPCPPCPAPEFLGGPSVF LFPPKPKDTLMISRTPEVTCVVVDVSQEDPEVQFNWYVDGVEVHNAKTKPREEQFNSTYR VVSVLTVLHQDWLNGKEYKCKVSNKGLPSSIEKTISKAKGQPREPQVYTLPPSQEEMTKN QVSLTCLVKGFYPSDIAVEWESNGQPENNYKTTPPVLDSDGSFFLYSRLTVDKSRWQEGN VFSCSVMHEALHNHYTQKSLSLSLGK | REGN5715 heavy chain |
| 30 | EIVLTQSPGTLSLSPGERATLSCRASQSVSSSYLAWYQQKPGQAPRLLIYGASSRATGIPDRF SGSGSGTDFTLTISRLEPEDFAVYYCQQYGSSPWTFGQGTKVEIKRTVAAPSVFIFPPSDEQ LKSGTASVVCLLNNFYPREAKVQWKVDNALQSGNSQESVTEQDSKDSTYSLSSTLTLSKAD YEKHKVYACEVTHQGLSSPVTKSFNRGEC | REGN5715 light chain |
| 31 | MGVFNYETETTSVIPAARLFKAFILDGDNLFPKVAPQAISSVENIEGNGGPGTIKKISFPEGL PFKYVKDRVDEVDHTNFKYNYSVIEGGPIGDTLEKISNEIKIVATPDGGSILKISNKYHTKGD HEVKAEQVKASKEMGETLLRAVESYLLAHSDAYN | Bet v 1 amino acid sequence from CAB02159 |
| 32 | MGVFNYETETTSVIPAARLFKAFILDGDNLFPKVAPQAISSVENIEGNGGPGTIKKISFPEGF PFKYVKDRVDEVDHTNFKYNYSVIEGGPIGDTLEKISNEIKIVATPDGGSILKISNKYHTKGD HEVKAEQVKASKEMGETLLRAVESYLLAHSDAYN | Bet v 1 amino acid sequence from Uniprot P15494 |

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims. The disclosures of all patents and non-patent literature cited herein are expressly incorporated in their entirety by reference.

---

We claim:

1. A method of treating birch allergy in a subject, the method comprising administering to the subject a pharmaceutical composition comprising:
   (a) a first anti-Bet v 1 antibody or antigen-binding fragment thereof, wherein the first anti-Bet v 1 antibody comprises a heavy chain complementarity determining region (HCDR) 1 comprising the amino acid sequence of SEQ ID NO:2, an HCDR2 comprising the amino acid sequence of SEQ ID NO:3, an HCDR3 comprising the amino acid sequence of SEQ ID NO:4, a light chain complementarity determining region (LCDR) 1 comprising the amino acid sequence of SEQ ID NO:6, an LCDR2 comprising the amino acid sequence of SEQ ID NO:7, and an LCDR3 comprising the amino acid sequence of SEQ ID NO:8;
   (b) a second anti-Bet v 1 antibody or antigen-binding fragment thereof, wherein the second anti-Bet v 1 antibody comprises an HCDR1 comprising the amino acid sequence of SEQ ID NO:12, an HCDR2 comprising the amino acid sequence of SEQ ID NO:13, an HCDR3 comprising the amino acid sequence of SEQ ID NO:14, an LCDR1 comprising the amino acid sequence of SEQ ID NO:16, an LCDR2 comprising the amino acid sequence of SEQ ID NO:17, and an LCDR3 comprising the amino acid sequence of SEQ ID NO:18; and
   (c) a third anti-Bet v 1 antibody or antigen-binding fragment thereof, wherein the third anti-Bet v 1 antibody comprises an HCDR1 comprising the amino acid sequence of SEQ ID NO:22, an HCDR2 comprising the amino acid sequence of SEQ ID NO:23, an HCDR3 comprising the amino acid sequence of SEQ ID NO:24, an LCDR1 comprising the amino acid sequence of SEQ ID NO:26, an LCDR2 comprising the amino acid sequence of SEQ ID NO:27, and an LCDR3 comprising the amino acid sequence of SEQ ID NO:28;
   wherein a single dose of the pharmaceutical composition is administered prior to the start of birch pollen season, wherein the pharmaceutical composition comprises each of the first anti-Bet v 1 antibody, the second anti-Bet v 1 antibody, and the third anti-Bet v 1 antibody at a dose of about 300 mg per antibody.

2. The method of claim 1, wherein the pharmaceutical composition is administered subcutaneously.

3. The method of claim 1, wherein the pharmaceutical composition is administered intravenously.

4. The method of claim 1, wherein the first anti-Bet v 1 antibody comprises a heavy chain variable region (HCVR) comprising the amino acid sequence of SEQ ID NO:1 and a light chain variable region (LCVR) comprising the amino acid sequence of SEQ ID NO:5.

5. The method of claim 4, wherein the first anti-Bet v 1 antibody comprises a heavy chain comprising the amino acid sequence of SEQ ID NO:9 and a light chain comprising the amino acid sequence of SEQ ID NO:10.

6. The method of claim 1, wherein the second anti-Bet v 1 antibody comprises an HCVR comprising the amino acid sequence of SEQ ID NO:11 and an LCVR comprising the amino acid sequence of SEQ ID NO:15.

7. The method of claim 6, wherein the second anti-Bet v 1 antibody comprises a heavy chain comprising the amino acid sequence of SEQ ID NO:19 and a light chain comprising the amino acid sequence of SEQ ID NO:20.

8. The method of claim 1, wherein the third anti-Bet v 1 antibody comprises an HCVR comprising the amino acid sequence of SEQ ID NO:21 and an LCVR comprising the amino acid sequence of SEQ ID NO:25.

9. The method of claim 8, wherein the third anti-Bet v 1 antibody comprises a heavy chain comprising the amino acid sequence of SEQ ID NO:29 and a light chain comprising the amino acid sequence of SEQ ID NO:30.

10. The method of claim 1, wherein treatment with the pharmaceutical composition:
reduces a subject's Total Nasal Symptom Score (TNSS);
reduces a subject's Total Ocular Symptom Score (TOSS);
reduces a subject's Total Symptom Score (TSS);
reduces a subject's Daily Medication Score (DMS);
reduces a subject's Combined Symptom and Medication Score (CSMS);
reduces a subject's birch skin prick test (SPT) mean wheal diameter; and/or
increases a subject's number of well days in which rescue medication is not utilized and the subject's TSS is ≤2 of 18.

11. The method of claim 10, wherein treatment with the pharmaceutical composition reduces a subject's TNSS, TOSS, TSS, DMS, and/or CSMS for the duration of birch pollen season.

12. The method of claim 1, wherein treatment with the pharmaceutical composition reduces allergic rhinitis symptoms in the subject.

13. The method of claim 12, wherein treatment with the pharmaceutical composition:
reduces a subject's Total Nasal Symptom Score (TNSS) AUC (0-1 hr) after nasal allergen challenge (NAC) by at least about 20%, relative to a baseline TNSS AUC (0-1 hr) value after NAC for the subject prior to the onset of treatment; and/or
reduces a subject's peak TNSS after NAC by at least about 25%, relative to a baseline peak TNSS value after NAC for the subject prior to the onset of treatment.

14. The method of claim 13, wherein administration of a single dose of the pharmaceutical composition:
reduces a subject's TNSS AUC (0-1 hr) after NAC by at least about 20% for at least two months after the pharmaceutical composition is administered; and/or
reduces a subject's peak TNSS after NAC by at least about 25% for at least two months after the pharmaceutical composition is administered.

15. The method of claim 1, wherein treatment with the pharmaceutical composition reduces allergic conjunctivitis symptoms in the subject.

16. The method of claim 15, wherein treatment with the pharmaceutical composition reduces a subject's TOSS AUC (0-1 hr) after NAC, relative to a baseline TOSS AUC (0-1 hr) value after NAC for the subject prior to the onset of treatment.

17. The method of claim 1, wherein treatment with the pharmaceutical composition improves peak nasal inspiratory flow (PNIF) in the subject by at least about 30%, relative to a baseline PNIF value for the subject prior to the onset of treatment.

18. The method of claim 1, wherein treatment with the pharmaceutical composition reduces birch sensitization in the subject by at least about 50% as measured by a skin prick test (SPT) with a birch allergen extract.

19. The method of claim 18, wherein administration of a single dose of the pharmaceutical composition reduces birch sensitization in the subject by at least about 60% for at least two months after the pharmaceutical composition is administered.

20. The method of claim 1, wherein the subject to be treated has a baseline serum allergen-specific IgE level ≥0.35 kUa/L for birch tree pollen and/or Bet v 1 allergen.

21. The method of claim 1, wherein the subject to be treated has a baseline positive SPT with a birch allergen extract.

22. A method of reducing one or more symptoms of an allergic reaction to a Fagales allergen in a subject, the method comprising administering to the subject a pharmaceutical composition comprising:
(a) a first anti-Bet v 1 antibody or antigen-binding fragment thereof, wherein the first anti-Bet v 1 antibody comprises a heavy chain complementarity determining region (HCDR) 1 comprising the amino acid sequence of SEQ ID NO:2, an HCDR2 comprising the amino acid sequence of SEQ ID NO:3, an HCDR3 comprising the amino acid sequence of SEQ ID NO:4, a light chain complementarity determining region (LCDR) 1 comprising the amino acid sequence of SEQ ID NO:6, an LCDR2 comprising the amino acid sequence of SEQ ID NO:7, and an LCDR3 comprising the amino acid sequence of SEQ ID NO:8;
(b) a second anti-Bet v 1 antibody or antigen-binding fragment thereof, wherein the second anti-Bet v 1 antibody comprises an HCDR1 comprising the amino acid sequence of SEQ ID NO:12, an HCDR2 comprising the amino acid sequence of SEQ ID NO:13, an HCDR3 comprising the amino acid sequence of SEQ ID NO:14, an LCDR1 comprising the amino acid sequence of SEQ ID NO:16, an LCDR2 comprising the amino acid sequence of SEQ ID NO:17, and an LCDR3 comprising the amino acid sequence of SEQ ID NO:18; and
(c) a third anti-Bet v 1 antibody or antigen-binding fragment thereof, wherein the third anti-Bet v 1 antibody comprises an HCDR1 comprising the amino acid sequence of SEQ ID NO:22, an HCDR2 comprising the amino acid sequence of SEQ ID NO:23, an HCDR3 comprising the amino acid sequence of SEQ ID NO:24, an LCDR1 comprising the amino acid sequence of SEQ ID NO:26, an LCDR2 comprising the amino acid sequence of SEQ ID NO:27, and an LCDR3 comprising the amino acid sequence of SEQ ID NO:28;
wherein a single dose of the pharmaceutical composition is administered prior to the start of birch pollen season, wherein the pharmaceutical composition comprises each of the first anti-Bet v 1 antibody, the second anti-Bet v 1 antibody, and the third anti-Bet v 1 antibody at a dose of about 300 mg per antibody.

23. The method of claim 22, wherein the Fagales allergen is Bet v 1.

24. The method of claim 22, wherein the subject is sensitized to Bet v 1 and to at least one other Fagales allergen.

25. The method of claim 22, wherein the pharmaceutical composition is administered subcutaneously.

26. The method of claim 22, wherein the pharmaceutical composition is administered intravenously.

27. The method of claim 22, wherein the first anti-Bet v 1 antibody comprises a heavy chain variable region (HCVR) comprising the amino acid sequence of SEQ ID NO:1 and a light chain variable region (LCVR) comprising the amino acid sequence of SEQ ID NO:5.

28. The method of claim 27, wherein the first anti-Bet v 1 antibody comprises a heavy chain comprising the amino acid sequence of SEQ ID NO:9 and a light chain comprising the amino acid sequence of SEQ ID NO:10.

29. The method of claim 22, wherein the second anti-Bet v 1 antibody comprises an HCVR comprising the amino acid sequence of SEQ ID NO:11 and an LCVR comprising the amino acid sequence of SEQ ID NO:15.

30. The method of claim 29, wherein the second anti-Bet v 1 antibody comprises a heavy chain comprising the amino acid sequence of SEQ ID NO:19 and a light chain comprising the amino acid sequence of SEQ ID NO:20.

31. The method of claim 22, wherein the third anti-Bet v 1 antibody comprises an HCVR comprising the amino acid sequence of SEQ ID NO:21 and an LCVR comprising the amino acid sequence of SEQ ID NO:25.

32. The method of claim 31, wherein the third anti-Bet v 1 antibody comprises a heavy chain comprising the amino acid sequence of SEQ ID NO:29 and a light chain comprising the amino acid sequence of SEQ ID NO:30.

33. The method of claim 22, wherein treatment with the pharmaceutical composition reduces allergic rhinitis symptoms in the subject.

34. The method of claim 22, wherein treatment with the pharmaceutical composition reduces allergic conjunctivitis symptoms in the subject.

35. The method of claim 22, wherein treatment with the pharmaceutical composition reduces sensitization to the Fagales allergen in the subject.

36. The method of claim 22, wherein the subject to be treated has a baseline serum allergen-specific IgE level ≥0.35 kUa/L for the Fagales allergen.

37. The method of claim 22, wherein the subject to be treated has a baseline positive SPT to the Fagales allergen.

* * * * *

SEQUENCE LISTING

<160> NUMBER OF SEQ ID NOS: 32

<210> SEQ ID NO 1
<211> LENGTH: 116
<212> TYPE: PRT
<213> ORGANISM: Artificial Sequence
<220> FEATURE:
<223> OTHER INFORMATION: Synthetic

<400> SEQUENCE: 1

Gln Val Gln Leu Gln Glu Ser Gly Pro Gly Leu Val Lys Pro Ser Glu
1               5                   10                  15

Thr Leu Ser Leu Thr Cys Ser Val Ser Gly Gly Ser Ile Thr Asn Tyr
                20                  25                  30

Phe Trp Thr Trp Ile Arg Gln Ser Pro Gly Lys Gly Leu Glu Trp Ile
            35                  40                  45

Gly Tyr Ile Tyr Tyr Ser Gly Gly Thr Asn Tyr Asn Pro Ser Leu Lys
        50                  55                  60

Ser Arg Val Thr Ile Ser Ile Asp Thr Ser Lys Asn Gln Phe Ser Leu
65                  70                  75                  80

Asn Met Asn Ser Val Thr Ala Ala Asp Thr Ala Val Tyr Tyr Cys Ala
                85                  90                  95

Gly Ser Tyr Tyr Tyr Gly Val Asp Val Trp Gly Gln Gly Thr Thr Val
            100                 105                 110

Thr Val Ser Ser
        115

<210> SEQ ID NO 2
<211> LENGTH: 8
<212> TYPE: PRT
<213> ORGANISM: Artificial Sequence
<220> FEATURE:
<223> OTHER INFORMATION: Synthetic

<400> SEQUENCE: 2

Gly Gly Ser Ile Thr Asn Tyr Phe
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic

<400> SEQUENCE: 3

Ile Tyr Tyr Ser Gly Gly Thr
1               5

<210> SEQ ID NO 4
<211> LENGTH: 10
<212> TYPE: PRT
<213> ORGANISM: Artificial Sequence
<220> FEATURE:
<223> OTHER INFORMATION: Synthetic

<400> SEQUENCE: 4

Ala Gly Ser Tyr Tyr Tyr Gly Val Asp Val
1               5                   10

<210> SEQ ID NO 5
<211> LENGTH: 107
<212> TYPE: PRT
<213> ORGANISM: Artificial Sequence
<220> FEATURE:
<223> OTHER INFORMATION: Synthetic

<400> SEQUENCE: 5

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Lys Ser Phe
            20                  25                  30

Leu Ala Trp Tyr Arg Gln Lys Pro Gly Gln Ala Pro Arg Leu Leu Ile
        35                  40                  45

Tyr Asp Ala Ser Asn Arg Pro Thr Gly Ile Pro Ala Arg Phe Ser Gly
    50                  55                  60

Ser Gly Ser Gly Thr Asp Phe Thr Leu Thr Ile Asn Ser Leu Glu Ser
65                  70                  75                  80

Glu Asp Phe Ala Val Tyr Phe Cys Gln Gln Arg Asn Asn Trp Pro Phe
                85                  90                  95

Thr Phe Gly Pro Gly Thr Lys Val Asp Ile Lys
            100                 105

<210> SEQ ID NO 6

```
<211> LENGTH: 6
<212> TYPE: PRT
<213> ORGANISM: Artificial Sequence
<220> FEATURE:
<223> OTHER INFORMATION: Synthetic

<400> SEQUENCE: 6

Gln Ser Ile Lys Ser Phe
1               5

<210> SEQ ID NO 7
<211> LENGTH: 3
<212> TYPE: PRT
<213> ORGANISM: Artificial Sequence
<220> FEATURE:
<223> OTHER INFORMATION: Synthetic

<400> SEQUENCE: 7

Asp Ala Ser
1

<210> SEQ ID NO 8
<211> LENGTH: 9
<212> TYPE: PRT
<213> ORGANISM: Artificial Sequence
<220> FEATURE:
<223> OTHER INFORMATION: Synthetic

<400> SEQUENCE: 8

Gln Gln Arg Asn Asn Trp Pro Phe Thr
1               5

<210> SEQ ID NO 9
<211> LENGTH: 443
<212> TYPE: PRT
<213> ORGANISM: Artificial Sequence
<220> FEATURE:
<223> OTHER INFORMATION: Synthetic

<400> SEQUENCE: 9

Gln Val Gln Leu Gln Glu Ser Gly Pro Gly Leu Val Lys Pro Ser Glu
1               5                   10                  15

Thr Leu Ser Leu Thr Cys Ser Val Ser Gly Gly Ser Ile Thr Asn Tyr
            20                  25                  30

Phe Trp Thr Trp Ile Arg Gln Ser Pro Gly Lys Gly Leu Glu Trp Ile
        35                  40                  45

Gly Tyr Ile Tyr Tyr Ser Gly Gly Thr Asn Tyr Asn Pro Ser Leu Lys
    50                  55                  60

Ser Arg Val Thr Ile Ser Ile Asp Thr Ser Lys Asn Gln Phe Ser Leu
65                  70                  75                  80

Asn Met Asn Ser Val Thr Ala Ala Asp Thr Ala Val Tyr Tyr Cys Ala
                85                  90                  95

Gly Ser Tyr Tyr Tyr Gly Val Asp Val Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175
```

-continued

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
        195                 200                 205

Lys Val Asp Lys Arg Val Glu Ser Lys Tyr Gly Pro Pro Cys Pro Pro
    210                 215                 220

Cys Pro Ala Pro Glu Phe Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
            420                 425                 430

Thr Gln Lys Ser Leu Ser Leu Ser Leu Gly Lys
        435                 440

<210> SEQ ID NO 10
<211> LENGTH: 214
<212> TYPE: PRT
<213> ORGANISM: Artificial Sequence
<220> FEATURE:
<223> OTHER INFORMATION: Synthetic

<400> SEQUENCE: 10

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Lys Ser Phe
            20                  25                  30

Leu Ala Trp Tyr Arg Gln Lys Pro Gly Gln Ala Pro Arg Leu Leu Ile
        35                  40                  45

Tyr Asp Ala Ser Asn Arg Pro Thr Gly Ile Pro Ala Arg Phe Ser Gly
    50                  55                  60

Ser Gly Ser Gly Thr Asp Phe Thr Leu Thr Ile Asn Ser Leu Glu Ser
65                  70                  75                  80

Glu Asp Phe Ala Val Tyr Phe Cys Gln Gln Arg Asn Asn Trp Pro Phe
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 11
<211> LENGTH: 119
<212> TYPE: PRT
<213> ORGANISM: Artificial Sequence
<220> FEATURE:
<223> OTHER INFORMATION: Synthetic

<400> SEQUENCE: 11

Glu Val Gln Leu Val Glu Ser Gly Gly Asp Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Phe Ile Ser Asp Ser Ser Ser Asn Ile Tyr Tyr Ala Asp Ser Val
    50                  55                  60

Lys Gly Arg Phe Thr Ile Ser Arg Asp Asn Ala Lys Lys Ser Leu Tyr
65                  70                  75                  80

Leu Gln Met Thr Ser Leu Arg Ala Glu Asp Thr Ala Val Tyr Tyr Cys
                85                  90                  95

Ala Arg Glu Ala Ile Gly Ser Thr Ser Phe Asp Asn Trp Gly Gln Gly
            100                 105                 110

Thr Leu Val Thr Val Ser Ser
        115

<210> SEQ ID NO 12
<211> LENGTH: 8
<212> TYPE: PRT
<213> ORGANISM: Artificial Sequence
<220> FEATURE:
<223> OTHER INFORMATION: Synthetic

<400> SEQUENCE: 12

Gly Phe Thr Phe Ser Ser Tyr Glu
1               5

<210> SEQ ID NO 13
<211> LENGTH: 8
<212> TYPE: PRT
<213> ORGANISM: Artificial Sequence
<220> FEATURE:
<223> OTHER INFORMATION: Synthetic

```
<400> SEQUENCE: 13

Ile Ser Asp Ser Ser Asn Ile
1               5

<210> SEQ ID NO 14
<211> LENGTH: 12
<212> TYPE: PRT
<213> ORGANISM: Artificial Sequence
<220> FEATURE:
<223> OTHER INFORMATION: Synthetic

<400> SEQUENCE: 14

Ala Arg Glu Ala Ile Gly Ser Thr Ser Phe Asp Asn
1               5                   10

<210> SEQ ID NO 15
<211> LENGTH: 107
<212> TYPE: PRT
<213> ORGANISM: Artificial Sequence
<220> FEATURE:
<223> OTHER INFORMATION: Synthetic

<400> SEQUENCE: 15

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Ser
            20                  25                  30

Leu Ala Trp Tyr Gln Gln Lys Pro Gly Gln Ala Pro Arg Arg Leu Ile
        35                  40                  45

Tyr Ser Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Ile Tyr Tyr Cys His Gln Tyr Asn Asn Trp Pro Leu
                85                  90                  95

Thr Phe Gly Gly Gly Thr Lys Val Glu Ile Lys
            100                 105

<210> SEQ ID NO 16
<211> LENGTH: 6
<212> TYPE: PRT
<213> ORGANISM: Artificial Sequence
<220> FEATURE:
<223> OTHER INFORMATION: Synthetic

<400> SEQUENCE: 16

Gln Ser Val Ser Ser Ser
1               5

<210> SEQ ID NO 17
<211> LENGTH: 3
<212> TYPE: PRT
<213> ORGANISM: Artificial Sequence
<220> FEATURE:
<223> OTHER INFORMATION: Synthetic

<400> SEQUENCE: 17

Ser Ala Ser
1

<210> SEQ ID NO 18
<211> LENGTH: 9
```

```
<212> TYPE: PRT
<213> ORGANISM: Artificial Sequence
<220> FEATURE:
<223> OTHER INFORMATION: Synthetic

<400> SEQUENCE: 18

His Gln Tyr Asn Asn Trp Pro Leu Thr
1               5

<210> SEQ ID NO 19
<211> LENGTH: 446
<212> TYPE: PRT
<213> ORGANISM: Artificial Sequence
<220> FEATURE:
<223> OTHER INFORMATION: Synthetic

<400> SEQUENCE: 19

Glu Val Gln Leu Val Glu Ser Gly Gly Asp Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Phe Ile Ser Asp Ser Ser Asn Ile Tyr Tyr Ala Asp Ser Val
    50                  55                  60

Lys Gly Arg Phe Thr Ile Ser Arg Asp Asn Ala Lys Lys Ser Leu Tyr
65                  70                  75                  80

Leu Gln Met Thr Ser Leu Arg Ala Glu Asp Thr Ala Val Tyr Tyr Cys
                85                  90                  95

Ala Arg Glu Ala Ile Gly Ser Thr Ser Phe Asp Asn Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320
```

```
Lys Val Ser Asn Lys Gly Leu Pro Ser Ser Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                    405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
            435                 440                 445

<210> SEQ ID NO 20
<211> LENGTH: 214
<212> TYPE: PRT
<213> ORGANISM: Artificial Sequence
<220> FEATURE:
<223> OTHER INFORMATION: Synthetic

<400> SEQUENCE: 20

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Ser
            20                  25                  30

Leu Ala Trp Tyr Gln Gln Lys Pro Gly Gln Ala Pro Arg Arg Leu Ile
            35                  40                  45

Tyr Ser Ala Ser Thr Arg Ala Thr Gly Ile Pro Ala Arg Phe Ser Gly
            50                  55                  60

Ser Gly Ser Gly Thr Glu Phe Thr Leu Thr Ile Ser Ser Leu Gln Ser
65                  70                  75                  80

Glu Asp Phe Ala Ile Tyr Tyr Cys His Gln Tyr Asn Asn Trp Pro Leu
            85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 21
```

<211> LENGTH: 120
<212> TYPE: PRT
<213> ORGANISM: Artificial Sequence
<220> FEATURE:
<223> OTHER INFORMATION: Synthetic

<400> SEQUENCE: 21

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Ile Ser Tyr
            20                  25                  30
Asn Ile Phe Trp Val Arg Gln Ala Thr Gly Gln Gly Leu Asp Trp Met
        35                  40                  45
Gly Trp Met Asn Pro Phe Arg Asn Asn Ala Gly Tyr Ala Gln Lys Phe
    50                  55                  60
Gln Gly Arg Val Thr Val Thr Trp Asp Thr Ser Ile Ser Thr Ala Tyr
65                  70                  75                  80
Met Glu Leu Ser Ser Leu Ser Ser Glu Asp Thr Ala Ile Tyr Tyr Cys
                85                  90                  95
Ala Arg Glu His Gly Ser Ser Trp Gly Phe Phe Asp Tyr Trp Gly Gln
            100                 105                 110
Gly Thr Leu Val Thr Val Ser Ser
        115                 120

<210> SEQ ID NO 22
<211> LENGTH: 8
<212> TYPE: PRT
<213> ORGANISM: Artificial Sequence
<220> FEATURE:
<223> OTHER INFORMATION: Synthetic

<400> SEQUENCE: 22

Gly Tyr Thr Phe Ile Ser Tyr Asn
1               5

<210> SEQ ID NO 23
<211> LENGTH: 8
<212> TYPE: PRT
<213> ORGANISM: Artificial Sequence
<220> FEATURE:
<223> OTHER INFORMATION: Synthetic

<400> SEQUENCE: 23

Met Asn Pro Phe Arg Asn Asn Ala
1               5

<210> SEQ ID NO 24
<211> LENGTH: 13
<212> TYPE: PRT
<213> ORGANISM: Artificial Sequence
<220> FEATURE:
<223> OTHER INFORMATION: Synthetic

<400> SEQUENCE: 24

Ala Arg Glu His Gly Ser Ser Trp Gly Phe Phe Asp Tyr
1               5                   10

<210> SEQ ID NO 25
<211> LENGTH: 108
<212> TYPE: PRT
<213> ORGANISM: Artificial Sequence
<220> FEATURE:
<223> OTHER INFORMATION: Synthetic

```
<400> SEQUENCE: 25

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105

<210> SEQ ID NO 26
<211> LENGTH: 7
<212> TYPE: PRT
<213> ORGANISM: Artificial Sequence
<220> FEATURE:
<223> OTHER INFORMATION: Synthetic

<400> SEQUENCE: 26

Gln Ser Val Ser Ser Ser Tyr
1               5

<210> SEQ ID NO 27
<211> LENGTH: 3
<212> TYPE: PRT
<213> ORGANISM: Artificial Sequence
<220> FEATURE:
<223> OTHER INFORMATION: Synthetic

<400> SEQUENCE: 27

Gly Ala Ser
1

<210> SEQ ID NO 28
<211> LENGTH: 9
<212> TYPE: PRT
<213> ORGANISM: Artificial Sequence
<220> FEATURE:
<223> OTHER INFORMATION: Synthetic

<400> SEQUENCE: 28

Gln Gln Tyr Gly Ser Ser Pro Trp Thr
1               5

<210> SEQ ID NO 29
<211> LENGTH: 447
<212> TYPE: PRT
<213> ORGANISM: Artificial Sequence
<220> FEATURE:
<223> OTHER INFORMATION: Synthetic

<400> SEQUENCE: 29

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ile Ser Tyr
            20                  25                  30

Asn Ile Phe Trp Val Arg Gln Ala Thr Gly Gln Gly Leu Asp Trp Met
```

```
                35                  40                  45
Gly Trp Met Asn Pro Phe Arg Asn Asn Ala Gly Tyr Ala Gln Lys Phe
 50                  55                  60

Gln Gly Arg Val Thr Val Thr Trp Asp Thr Ser Ile Ser Thr Ala Tyr
 65                  70                  75                  80

Met Glu Leu Ser Ser Leu Ser Ser Glu Asp Thr Ala Ile Tyr Tyr Cys
                 85                  90                  95

Ala Arg Glu His Gly Ser Ser Trp Gly Phe Phe Asp Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445
```

<210> SEQ ID NO 30

<211> LENGTH: 215
<212> TYPE: PRT
<213> ORGANISM: Artificial Sequence
<220> FEATURE:
<223> OTHER INFORMATION: Synthetic

<400> SEQUENCE: 30

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 31
<211> LENGTH: 160
<212> TYPE: PRT
<213> ORGANISM: Artificial Sequence
<220> FEATURE:
<223> OTHER INFORMATION: Synthetic

<400> SEQUENCE: 31

Met Gly Val Phe Asn Tyr Glu Thr Glu Thr Thr Ser Val Ile Pro Ala
1               5                   10                  15

Ala Arg Leu Phe Lys Ala Phe Ile Leu Asp Gly Asp Asn Leu Phe Pro
            20                  25                  30

Lys Val Ala Pro Gln Ala Ile Ser Ser Val Glu Asn Ile Glu Gly Asn
        35                  40                  45

Gly Gly Pro Gly Thr Ile Lys Lys Ile Ser Phe Pro Glu Gly Leu Pro
    50                  55                  60

Phe Lys Tyr Val Lys Asp Arg Val Asp Glu Val Asp His Thr Asn Phe
65                  70                  75                  80

Lys Tyr Asn Tyr Ser Val Ile Glu Gly Gly Pro Ile Gly Asp Thr Leu
                85                  90                  95

Glu Lys Ile Ser Asn Glu Ile Lys Ile Val Ala Thr Pro Asp Gly Gly

```
                    100                 105                 110
Ser Ile Leu Lys Ile Ser Asn Lys Tyr His Thr Lys Gly Asp His Glu
            115                 120                 125

Val Lys Ala Glu Gln Val Lys Ala Ser Lys Glu Met Gly Glu Thr Leu
    130                 135                 140

Leu Arg Ala Val Glu Ser Tyr Leu Leu Ala His Ser Asp Ala Tyr Asn
145                 150                 155                 160

<210> SEQ ID NO 32
<211> LENGTH: 160
<212> TYPE: PRT
<213> ORGANISM: Artificial Sequence
<220> FEATURE:
<223> OTHER INFORMATION: Synthetic

<400> SEQUENCE: 32

Met Gly Val Phe Asn Tyr Glu Thr Glu Thr Thr Ser Val Ile Pro Ala
1               5                   10                  15

Ala Arg Leu Phe Lys Ala Phe Ile Leu Asp Gly Asp Asn Leu Phe Pro
            20                  25                  30

Lys Val Ala Pro Gln Ala Ile Ser Ser Val Glu Asn Ile Glu Gly Asn
        35                  40                  45

Gly Gly Pro Gly Thr Ile Lys Lys Ile Ser Phe Pro Glu Gly Phe Pro
    50                  55                  60

Phe Lys Tyr Val Lys Asp Arg Val Asp Glu Val Asp His Thr Asn Phe
65                  70                  75                  80

Lys Tyr Asn Tyr Ser Val Ile Glu Gly Gly Pro Ile Gly Asp Thr Leu
                85                  90                  95

Glu Lys Ile Ser Asn Glu Ile Lys Ile Val Ala Thr Pro Asp Gly Gly
            100                 105                 110

Ser Ile Leu Lys Ile Ser Asn Lys Tyr His Thr Lys Gly Asp His Glu
            115                 120                 125

Val Lys Ala Glu Gln Val Lys Ala Ser Lys Glu Met Gly Glu Thr Leu
    130                 135                 140

Leu Arg Ala Val Glu Ser Tyr Leu Leu Ala His Ser Asp Ala Tyr Asn
145                 150                 155                 160
```